US011282588B2

(12) United States Patent
Ciesla et al.

(10) Patent No.: US 11,282,588 B2
(45) Date of Patent: Mar. 22, 2022

(54) STORAGE DEVICE, SYSTEM, AND METHOD

(71) Applicant: ILLUMINA, INC., San Diego, CA (US)

(72) Inventors: Craig Ciesla, Mountain View, CA (US); Ali Agah, Menlo Park, CA (US); Stanley Hong, Palo Alto, CA (US); Tarun Khurana, Freemont, CA (US); Aathavan Karunakaran, Berkeley, CA (US); Arvin Emadi, San Jose, CA (US); Merek Siu, Alameda, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 17/254,459

(22) PCT Filed: May 26, 2020

(86) PCT No.: PCT/US2020/034515
§ 371 (c)(1),
(2) Date: Dec. 21, 2020

(87) PCT Pub. No.: WO2020/243075
PCT Pub. Date: Dec. 3, 2020

(65) Prior Publication Data
US 2021/0151129 A1    May 20, 2021

Related U.S. Application Data

(60) Provisional application No. 62/855,690, filed on May 31, 2019, provisional application No. 62/855,616, filed on May 31, 2019.

(51) Int. Cl.
G16B 50/30    (2019.01)
G06F 3/06    (2006.01)
(Continued)

(52) U.S. Cl.
CPC ............ *G16B 50/30* (2019.02); *B01L 3/5027* (2013.01); *G11C 13/02* (2013.01); *G16B 30/10* (2019.02); *C12Q 1/6874* (2013.01)

(58) Field of Classification Search
CPC ....... G16B 50/30; G16B 30/10; B01L 3/5027; G11C 13/02
See application file for complete search history.

(56) References Cited

U.S. PATENT DOCUMENTS

| 5,787,032 A | 7/1998 | Heller et al. |
| 7,414,116 B2 | 8/2008 | Milton et al. |
| (Continued) | | |

FOREIGN PATENT DOCUMENTS

| WO | WO 2014/150522 A1 | 9/2014 | |
| WO | WO-2017015018 A1 * | 1/2017 | ........... C12Q 1/6837 |

OTHER PUBLICATIONS

International Search Report and Written Opinion dated Jul. 14, 2020 for International Application No. PCT/US2020/034515, 6 pages.

*Primary Examiner* — Benjamin R Whatley
(74) *Attorney, Agent, or Firm* — Frost Brown Todd LLC

(57) ABSTRACT

A system writes input data to a storage device as machine-written polynucleotides; and reads machine written polynucleotides from the storage device as output data. The storage device includes a flow cell including a plurality of storage wells in which machine written polynucleotides may be stored. The storage device may include a set of electrodes corresponding to the storage wells that allow for selective interactions with wells across the surface of a flow cell. Operation of the storage device may include receiving a read request associated with a particular location in the storage device, creating a copy of a nucleotide sequence located at the particular location in the storage device, transferring the copy of the nucleotide sequence to a read location, and (Continued)

reading the copy of the nucleotide sequence at the read location.

9 Claims, 17 Drawing Sheets

(51) Int. Cl.
*G16B 30/10* (2019.01)
*C12Q 1/6869* (2018.01)
*G11C 13/02* (2006.01)
*B01L 3/00* (2006.01)
*C12Q 1/6874* (2018.01)

(56) References Cited

U.S. PATENT DOCUMENTS

| | | |
|---|---|---|
| 8,906,320 B1 | 12/2014 | Eltoukhy et al. |
| 9,012,022 B2 | 4/2015 | George et al. |
| 9,453,258 B2 | 9/2016 | Kain et al. |
| 9,512,422 B2 | 12/2016 | Barnard et al. |
| 10,254,225 B2 | 4/2019 | Zhong et al. |
| 2008/0311122 A1* | 12/2008 | Wu .................. A61P 43/00 424/135.1 |
| 2015/0209786 A1* | 7/2015 | Hage ................ B01L 3/527 435/6.12 |
| 2015/0261664 A1 | 9/2015 | Goldman et al. |
| 2016/0356715 A1* | 12/2016 | Zhong ............... G01N 21/6454 |
| 2018/0117587 A1 | 5/2018 | Lemoine et al. |
| 2018/0207920 A1* | 7/2018 | Venkatesan .......... B01L 3/505 |

* cited by examiner

STORAGE DEVICE, SYSTEM, AND METHOD

RELATED APPLICATIONS

This application is a national stage entry of International Patent Application No. PCT/US2020/034515, entitled "Storage Device, System, and Method," filed on May 26, 2020, which claims priority to U.S. Provisional Patent App. No. 62/855,616, entitled "Non-Volatile Polynucleotide Storage Device, System, and Method," filed on May 31, 2019, which is incorporated by reference herein in its entirety. International Patent Application No. PCT/US2020/034515 also claims priority to U.S. Provisional Patent App. No. 62/855,690, entitled "DNA Storage Device with Separate Reading and Writing Locations," filed on May 31, 2019, which is incorporated by reference herein in its entirety.

BACKGROUND

Computer systems have used various different mechanisms to store data, including magnetic storage, optical storage, and solid-state storage. Such forms of data storage may present drawbacks in the form of read-write speed, duration of data retention, power usage, or data density.

Just as naturally occurring DNA may be read, machine-written DNA may also be read. Pre-existing DNA reading techniques may include an array-based, cyclic sequencing assay (e.g., sequencing-by-synthesis (SBS)), where a dense array of DNA features (e.g., template nucleic acids) are sequenced through iterative cycles of enzymatic manipulation. After each cycle, an image may be captured and subsequently analyzed with other images to determine a sequence of the machine-written DNA features. In another biochemical assay, an unknown analyte having an identifiable label (e.g., fluorescent label) may be exposed to an array of known probes that have predetermined addresses within the array. Observing chemical reactions that occur between the probes and the unknown analyte may help identify or reveal properties of the analyte.

SUMMARY

Described herein are devices, systems, and methods for DNA storage of data including features for per-well activation, simultaneous read-write caching, and multi-volume management for simultaneous read-write capabilities.

An implementation relates to a system for non-volatile storage comprising: a processor and a memory; a module interface; a removable storage device for receipt in the module interface, the removable storage device comprising: a case adapted to couple with the module interface and fix the removable storage device at a static position, and a flow cell positioned within the case, the flow cell comprising a plurality of wells with open sides accessible from a first surface of the flow cell, wherein the wells are adapted to contain polynucleotides storing machine written data; a fluidics device to provide one or more reagents to the removable storage device; and a sequencing device to analyze polynucleotides within the removable storage device and determine nucleotides; wherein the processor is to perform a data read process to: determine a set of sequencing data indicative of nucleotides of a polynucleotide in a well of the plurality of wells, and determine a set of machine written binary data based upon the set of sequencing data.

Variations on any one or more of the above implementations exist, wherein the processor, when performing the data read process: identifies the well of the plurality of wells from which data is to be read, operates the fluidics device and the sequencing device to perform sequencing-by-synthesis on the polynucleotide in the well, captures the set of sequencing data from the sequencing device during sequencing-by-synthesis, and converts the set of sequencing data into the set of binary data based upon an encoding scheme.

Variations on any one or more of the above implementations exist, wherein the encoding scheme comprises a set of encoding rules usable by the processor to convert data between a binary format having base 2, and a polynucleotide format having a base of greater than 2.

Variations on any one or more of the above implementations exist, Wherein the base of the polynucleotide format is base 4.

Variations on any one or more of the above implementations exist, wherein the flow cell is sealed within the case, the removable storage device further comprising: a sequencing interface positioned on the case and to transmit light from the sequencing device to the well when the removable storage device is at the static position, and a fluidic interface positioned on the case and to transmit fluid from the fluidic device to the well when the removable storage device is at the static position.

Variations on any one or more of the above implementations exist, wherein the sequencing interface comprises a glass substrate, and wherein the fluidic interface comprises a passive manifold.

Variations on any one or more of the above implementations exist, further comprising a synthesis device to provide nucleotides and create polynucleotides within the removable storage device, wherein the processor further, when performing a data write process: receives a set of input data, determines a set of input sequencing data based upon the set of input data, and operates the synthesis device to create an input polynucleotide in a target well of the plurality of wells based on the set of input sequencing data.

Variations on any one or more of the above implementations exist, wherein the processor further: stores a set of index data describing the contents of each well of the plurality of wells, identifies the well of the plurality of wells from which data is to be read based upon the set of index data, determines the target well based upon the set of index data, and updates the set of index data after creating the input polynucleotide in the target well.

Variations on any one or more of the above implementations exist, the removable storage device further comprising a device memory, wherein the processor further stores the set of index data for the removable storage device on the device memory for that removable storage device.

Variations on any one or more of the above implementations exist, wherein the device memory is to receive the set of index data wirelessly.

Variations on any one or more of the above implementations exist, the removable storage device further comprising an electrical interface positioned on the case and to exchange electrical signals with the sequencing device when the removable storage device is at the static position.

Variations on any one or more of the above implementations exist, the removable storage device further comprising an integrated circuit positioned on a second surface of the flow cell, wherein the electrical interface is to provide power and instructions to operate the integrated circuit, wherein the second surface is opposite the first surface.

Variations on any one or more of the above implementations exist, wherein the integrated circuit is to selectively, based on signals received from the sequencing device: emit light into each well of the plurality of wells, detect fluorescence of the light emitted from a label associated with a nucleotide in each well of the plurality of wells, and provide a set of fluorescence data to the sequencing device, wherein the set of fluorescence data is usable to determine the set of sequencing data.

Variations on any one or more of the above implementations exist, the system further comprising a conditioning device, wherein the processor further: receives a signal indicating that the removable storage device has been coupled with the module interface, operates the fluidics device to provide a preparation fluid to the flow cell, wherein the preparation fluid is adapted to remove a preservative coating on the flow cell to enable the flow cell for read and write operations, and operates the conditioning device to bring the flow cell to a predetermined temperature.

Variations on any one or more of the above implementations exist, the system further comprising a conditioning device, wherein the conditioning device is to effect preservation of polynucleotides in the plurality of wells.

Variations on any one or more of the above implementations exist, wherein the conditioning device is to freeze dry the flow cell to preserve polynucleotides in the plurality of wells.

Variations on any one or more of the above implementations exist, wherein the conditioning device comprises a feature of the fluidics device that dispenses a preservative fluid to the flow cell to thereby apply a preservative coating on the flow cell to preserve and protect polynucleotides in the plurality of wells.

Variations on any one or more of the above implementations exist, wherein the processor further: receives a signal indicating that the removable storage device is to be dismounted from the module interface, and activate the conditioning device in response to the signal indicating that the removable storage device is to be dismounted from the module interface.

Variations on any one or more of the above implementations exist, wherein the processor further: receives a signal indicating that the removable storage device has been dismounted from the module interface, and provide a notification to a user that the removable storage device is dismounted in response to the signal indicating that the removable storage device has been dismounted from the module interface.

Another implementation relates to a method for non-volatile storage comprising: placing a removable storage device in a module interface of a storage instrument, the removable storage device comprising a flow cell, wherein the module interface is adapted to fix the removable storage device in a static position; operating a sequencing device to perform sequencing-by-synthesis on a polynucleotide within a well of a plurality of wells of the flow cell to determine a set of sequencing data that describes nucleotides of the polynucleotide; operating a fluidics device to provide one or more fluid types to the flow cell for sequencing-by-synthesis with the sequencing device; and determine a set of binary data based upon the set of sequencing data and an encoding scheme, wherein the encoding scheme describes a set of rules to convert information from a binary format to a non-binary format associated with the set of sequencing data.

Variations on any one or more of the above implementations exist, further comprising: receiving a set of input data; determining a set of input sequencing data based upon the set of input data and the encoding scheme; and operating a synthesis device to create an input polynucleotide in a target well of the plurality of wells based on the set of input sequencing data.

Variations on any one or more of the above implementations exist, further comprising receiving a signal indicating that the removable storage device has been coupled with the module interface.

Variations on any one or more of the above implementations exist, further comprising operating the fluidics device to provide a preparation fluid to the flow cell in response to the signal indicating that the removable storage device has been coupled with the module interface, wherein the preparation fluid is adapted to remove a preservative coating on the flow cell to enable the flow cell for read and write operations.

Variations on any one or more of the above implementations exist, further comprising operating a conditioning device in response to the signal indicating that the removable storage device has been coupled with the module interface, wherein the conditioning device brings the flow cell to a predetermined temperature required for read and write operations.

Variations on any one or more of the above implementations exist, further comprising receiving a signal indicating that the removable storage device is to be dismounted from the module interface.

Variations on any one or more of the above implementations exist, further comprising activating a conditioning device in response to the signal indicating that the removable storage device is to be dismounted from the module interface.

Variations on any one or more of the above implementations exist, wherein the activated conditioning device dispenses a preservative fluid to the flow cell to thereby apply a preservative coating on the flow cell to preserve and protect polynucleotides in the plurality of wells.

Variations on any one or more of the above implementations exist, Wherein the activated conditioning device freeze dries the flow cell to preserve polynucleotides in the plurality of wells.

Variations on any one or more of the above implementations exist, further comprising: receiving a signal indicating that the removable storage device has been dismounted from the module interface; and providing a notification to a user that the removable storage device is dismounted in response to the signal indicating that the removable storage device has been dismounted from the module interface.

Another implementation relates to a removable storage device for non-volatile storage comprising: a case adapted to couple with a module interface of a storage instrument and fix the removable storage device at a static position; a flow cell sealed within the case, the flow cell comprising a plurality of wells with open sides accessible from a first surface of the flow cell, the wells being adapted to contain polynucleotides storing machine-written data; a sequencing interface positioned proximately to the flow cell and adapted to transmit light to the well when the removable storage device is at the static position; and a fluidic interface positioned on the case and adapted to transmit fluid from a fluidic device of the storage instrument to the well when the removable storage device is at the static position.

Variations on any one or more of the above implementations exist, further comprising an electrical interface positioned on the case to exchange electrical signals with the storage instrument when the removable storage device is at the static position.

Variations on any one or more of the above implementations exist, further comprising an integrated circuit positioned on a second surface of the flow cell, the electrical interface to provide power and instructions to operate an integrated circuit.

Variations on any one or more of the above implementations exist, wherein the second surface is opposite the first surface, and wherein the integrated circuit selectively, based on signals received from the storage instrument: emits light into each well of the plurality of wells via the sequencing interface, detect fluorescence of light emitted from a label associated with a nucleotide in each well of the plurality of wells, and provide a set of fluorescence data to the storage instrument, wherein the set of fluorescence data is usable to determine a set of sequencing data that describes the nucleotides of a polynucleotide in each well of the plurality of wells.

Variations on any one or more of the above implementations exist, wherein the removable storage device comprises: a power connection to couple the removable storage device with a power source, and a set of sensors to detect one or more characteristics of the flow cell and provide an indication when a detected characteristic exceeds a predetermined threshold, wherein the set of sensors comprises one or more sensors selected from the group consisting of a temperature sensor, a humidity sensor, a light sensor, and a radiation sensor.

Variations on any one or more of the above implementations exist, further comprising at least one sensor, the at least one sensor to indicate whether one or more environmental conditions fall outside a predetermined range, the one or more environmental conditions including one or more of humidity, temperature, light, or radiation.

Variations on any one or more of the above implementations exist, the flow cell comprising a substrate with a plurality of openings formed through bottom regions of the wells.

Variations on any one or more of the above implementations exist, the flow cell further comprising an electrically conductive material in the openings formed through the bottom regions of the wells.

Variations on any one or more of the above implementations exist, the electrically conductive material comprising indium tin oxide.

Variations on any one or more of the above implementations exist, further comprising transparent anisotropic material in the openings formed through the bottom regions of the wells.

Variations on any one or more of the above implementations exist, the flow cell including an underside with one or more pads to contact an integrated circuit chip positioned under the flow cell.

Variations on any one or more of the above implementations exist, the flow cell comprising glass.

Variations on any one or more of the above implementations exist, further comprising a thin film medium to transfer polynucleotides to a corresponding sequencing surface in the flow cell.

Variations on any one or more of the above implementations exist, wherein the polynucleotides are transferred to the corresponding sequencing surface in the flow cell electrophoretically.

Variations on any one or more of the above implementations exist, wherein the polynucleotides are transferred to the corresponding sequencing surface in the flow cell via blotting.

An implementation relates to a method comprising receiving a read request, wherein the read request is associated with a particular location in a storage device; creating a copy of a polynucleotide located at the particular location in the storage device; transferring the copy of the polynucleotide to a read location; and reading the copy of the polynucleotide at the read location.

Variations on any one or more of the above implementations exist, wherein the storage device comprises a set of one or more write locations; the particular location is comprised by the set of one or more write locations; the read location is not comprised by the set of one or more write locations; and the storage device is to, whenever it receives a write request, only write data to locations comprised by the set of one or more write locations.

Variations on any one or more of the above implementations exist, wherein the storage device comprises a flow cell; each write location from the one or more write locations is disposed on a first surface of the flow cell; and the read location is disposed on a second surface of the flow cell.

Variations on any one or more of the above implementations exist, wherein the first surface and the second surface are opposed to each other.

Variations on any one or more of the above implementations exist, wherein the first surface is a bottom surface of the flow cell; and the second surface is a top surface of the flow cell.

Variations on any one or more of the above implementations exist, wherein each write location from the set of one or more write locations has a corresponding set of electrodes to encode data using nucleotides in that write location.

Variations on any one or more of the above implementations exist, wherein: the storage device comprises a dedicated integrated circuit; and the dedicated integrated circuit is to, for each write location from the set of one or more write locations, drive the set of electrodes corresponding to that location to thereby encode data using nucleotides in that write location.

Variations on any one or more of the above implementations exist, wherein the storage device comprises a second integrated circuit, wherein the second integrated circuit is to read data from nucleotides at the read location.

Variations on any one or more of the above implementations exist, wherein the dedicated integrated circuit and the second integrated circuit are both complementary-metal-oxide semiconductor (CMOS) chips.

Variations on any one or more of the above implementations exist, wherein: each write location from the set of one or more write locations is addressable; and the storage device does not comprise any addressable locations to store data in the form of polynucleotides other than the set of one or more write locations.

Variations on any one or more of the above implementations exist, wherein: the storage device stores a set of one or more logical data groupings; the method comprises creating an index specifying, for each logical data grouping from the set of one or more logical data groupings, an associated set of one or more locations; and for each logical data grouping from the set of one or more logical data groupings, each location from that logical data grouping's associated set of one or more locations is a write location comprised by the set of one or more write locations.

Variations on any one or more of the above implementations exist, wherein the method comprises receiving a request to retrieve a particular logical data grouping from the set of one or more logical data groupings; retrieving, from the index, the particular logical data grouping's associated set of one or more locations; and determining the particular location in the storage device based on the particular logical data grouping's associated set of one or more locations.

Variations on any one or more of the above implementations exist, wherein, for each logical data grouping from the set of one or more logical data groupings, that logical data grouping's associated set of one or more locations comprises a starting location and an ending location.

Variations on any one or more of the above implementations exist, wherein, for each logical data grouping from the set of one or more logical data groupings, each location from that logical data grouping's associated set of one or more locations is a location in a two-dimensional grid.

Variations on any one or more of the above implementations exist, wherein the method comprises storing the index in a non-nucleotide memory; and storing the index using nucleotides on a bead.

Variations on any one or more of the above implementations exist, wherein transferring the copy of the polynucleotide to the read location comprises fixing the copy of the polynucleotide to a bead at the particular location; and transferring the bead from the particular location to the read location.

Variations on any one or more of the above implementations exist, Wherein the particular location is on the surface of a bead.

Variations on any one or more of the above implementations exist, wherein transferring the copy of the polynucleotide to the read location is performed using a technique selected from the group consisting of: electrophoresis; dielectrophoresis; and laminar fluid flow.

Another implementation relates to a system comprising one or more non-transitory computer readable media storing instructions to perform a method comprising receiving a read request, wherein the read request is associated with a particular location in a storage device; creating a copy of a polynucleotide located at the particular location in the storage device; transferring the copy of the polynucleotide to a read location; and reading the copy of the polynucleotide at the read location.

Variations on any one or more of the above implementations exist, wherein the storage device comprises a set of one or more write locations; the particular location is comprised by the set of one or more write locations; the read location is not comprised by the set of one or more write locations; and the storage device is to, whenever it receives a write request, only write data to locations comprised by the set of one or more write locations.

Variations on any one or more of the above implementations exist, wherein the storage device comprises a flow cell; each write location from the one or more write locations is disposed on a first surface of the flow cell; and the read location is disposed on a second surface of the flow cell.

Variations on any one or more of the above implementations exist, wherein the first surface and the second surface are opposed to each other.

Variations on any one or more of the above implementations exist, wherein the first surface is a bottom surface of the flow cell; and the second surface is a top surface of the flow cell.

Variations on any one or more of the above implementations exist, wherein each write location from the set of one or more write locations has a corresponding set of electrodes to encode data using nucleotides in that write location.

Variations on any one or more of the above implementations exist, wherein the storage device comprises a dedicated integrated circuit; and the dedicated integrated circuit is to, for each write location from the set of one or more write locations, drive the set of electrodes corresponding to that location to thereby encode data using nucleotides in that write location.

Variations on any one or more of the above implementations exist, wherein the storage device comprises a second integrated circuit, wherein the second integrated circuit is to read data from nucleotides at the read location.

Variations on any one or more of the above implementations exist, wherein the dedicated integrated circuit and the second integrated circuit are both CMOS chips.

Variations on any one or more of the above implementations exist, wherein each write location from the set of one or more write locations is addressable; and the storage device does not comprise any addressable locations to store data in the form of polynucleotides other than the set of one or more write locations.

Variations on any one or more of the above implementations exist, wherein the storage device stores a set of one or more logical data groupings; the method comprises creating an index specifying, for each logical data grouping from the set of one or more logical data groupings, an associated set of one or more locations; and for each logical data grouping from the set of one or more logical data groupings, each location from that logical data grouping's associated set of one or more location is a write location comprised by the set of one or more write locations.

Variations on any one or more of the above implementations exist, wherein the method comprises: receiving a request to retrieve a particular logical data grouping from the set of one or more logical data groupings; retrieving, from the index, the particular logical data grouping's associated set of one or more locations; and determining the particular location in the storage device based on the particular logical data grouping's associated set of one or more locations.

Variations on any one or more of the above implementations exist, wherein, for each logical data grouping from the set of one or more logical data groupings, that logical data grouping's associated set of one or more locations comprises a starting location and an ending location.

Variations on any one or more of the above implementations exist, wherein, for each logical data grouping from the set of one or more logical data groupings, each location from that logical data grouping's associated set of one or more locations is a location in a two-dimensional grid.

Variations on any one or more of the above implementations exist, wherein the method comprises: storing the index in a non-nucleotide memory; and storing the index using nucleotides on a bead.

Variations on any one or more of the above implementations exist, wherein transferring the copy of the polynucleotide to the read location comprises fixing the copy of the polynucleotide to a bead at the particular location; and transferring the bead from the particular location to the read location.

Variations on any one or more of the above implementations exist, wherein the particular location is on the surface of a bead.

Variations on any one or more of the above implementations exist, wherein transferring the copy of the polynucleotide to the read location is performed using a technique selected from the group consisting of: electrophoresis; dielectrophoresis; and laminar fluid flow.

An implementation relates to one or more non-transitory computer readable media storing instructions for performing a method comprising: receiving a read request, wherein the read request is associated with a particular location in a storage device; creating a copy of a polynucleotide located at the particular location in the storage device; transferring the copy of the polynucleotide to a read location; and reading the copy of the polynucleotide at the read location.

Variations on any one or more of the above implementations exist, wherein: the storage device comprises a set of one or more write locations; the particular location is comprised by the set of one or more write locations; the read location is not comprised by the set of one or more write locations; and the storage device is to, whenever it receives a write request, only write data to locations comprised by the set of one or more write locations.

Variations on any one or more of the above implementations exist, wherein: the storage device comprises a flow cell; each write location from the one or more write locations is disposed on a first surface of the flow cell; and the read location is disposed on a second surface of the flow cell.

Variations on any one or more of the above implementations exist, wherein the first surface and the second surface are opposed to each other.

Variations on any one or more of the above implementations exist, wherein: the first surface is a bottom surface of the flow cell; and the second surface is a top surface of the flow cell.

Variations on any one or more of the above implementations exist, wherein each write location from the set of one or more write locations has a corresponding set of electrodes to encode data using nucleotides in that write location.

Variations on any one or more of the above implementations exist, wherein: the storage device comprises a dedicated integrated circuit; and the dedicated integrated circuit is to, for each write location from the set of one or more write locations, drive the set of electrodes corresponding to that location to thereby encode data using nucleotides in that write location.

Variations on any one or more of the above implementations exist, wherein the storage device comprises a second integrated circuit, wherein the second integrated circuit is to read data from nucleotides at the read location.

Variations on any one or more of the above implementations exist, wherein the dedicated integrated circuit and the second integrated circuit are both CMOS chips.

Variations on any one or more of the above implementations exist, wherein: each write location from the set of one or more write locations is addressable; and the storage device does not comprise any addressable locations to store data in the form of polynucleotides other than the set of one or more write locations.

Variations on any one or more of the above implementations exist, wherein: the storage device stores a set of one or more logical data groupings; the method comprises creating an index specifying, for each logical data grouping from the set of one or more logical data groupings, an associated set of one or more locations; and for each logical data grouping from the set of one or more logical data groupings, each location from that logical data grouping's associated set of one or more location is a write location comprised by the set of one or more write locations.

Variations on any one or more of the above implementations exist, wherein the method comprises: receiving a request to retrieve a particular logical data grouping from the set of one or more logical data groupings; retrieving, from the index, the particular logical data grouping's associated set of one or more locations; and determining the particular location in the storage device based on the particular logical data grouping's associated set of one or more locations.

Variations on any one or more of the above implementations exist, wherein, for each logical data grouping from the set of one or more logical data groupings, that logical data grouping's associated set of one or more locations comprises a starting location and an ending location.

Variations on any one or more of the above implementations exist, wherein, for each logical data grouping from the set of one or more logical data groupings, each location from that logical data grouping's associated set of one or more locations is a location in a two-dimensional grid.

Variations on any one or more of the above implementations exist, wherein the method comprises: storing the index in a non-nucleotide memory; and storing the index using nucleotides on a bead.

Variations on any one or more of the above implementations exist, wherein transferring the copy of the polynucleotide to the read location comprises: fixing the copy of the polynucleotide to a bead at the particular location; and transferring the bead from the particular location to the read location.

Variations on any one or more of the above implementations exist, wherein the particular location is on the surface of a bead.

Variations on any one or more of the above implementations exist, wherein transferring the copy of the polynucleotide to the read location is performed using a technique selected from the group consisting of: electrophoresis; dielectrophoresis; and laminar fluid flow.

It should be appreciated that all combinations of the foregoing concepts and additional concepts discussed in greater detail below (provided such concepts are not mutually inconsistent) are contemplated as being part of the inventive subject matter disclosed herein and to achieve the benefits/advantages as described herein. In particular, all combinations of claimed subject matter appearing at the end of this disclosure are contemplated as being part of the inventive subject matter disclosed herein.

BRIEF DESCRIPTION OF THE DRAWINGS

The details of one or more implementations are set forth in the accompanying drawings and the description below. Other features, aspects, and advantages will become apparent from the description, the drawings, and the claims, in which:

Figure 1:
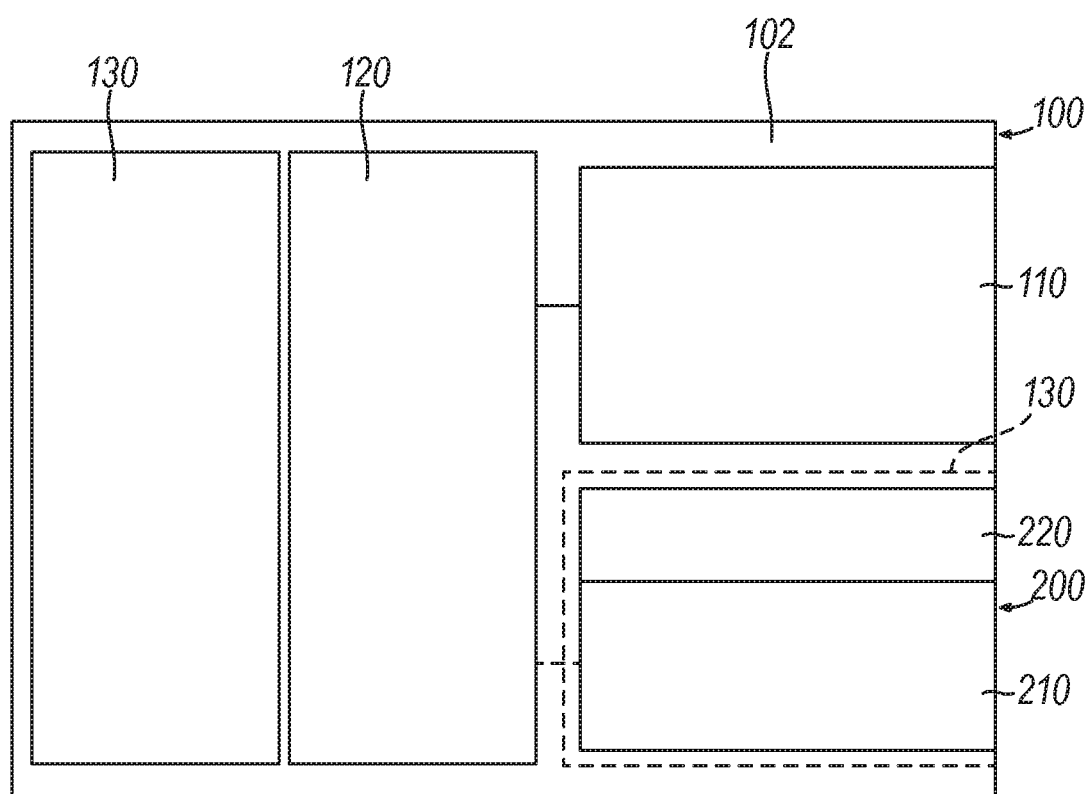
FIG. 1 depicts a block schematic view of an example of a system that may be used to conduct biochemical processes.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

In some aspects, methods and systems are disclosed herein for a DNA storage device that may be removable and portable, and that may be usable as a DNA hard drive device for archival purposes on large and small scales. In some further aspects, methods and systems are disclosed herein for mitigating the risk of data errors in a DNA storage device containing machine-written DNA. Machine-written DNA may provide an alternative to traditional forms of data storage (e.g., magnetic storage, optical storage, and solid-state storage). Machine-written DNA may provide faster read-write speeds, longer data retention, reduced power usage, and higher data density. While examples described herein refer to a "DNA storage system" or a "DNA storage device," it should be understood that this is only one example of polynucleotide storage. The teachings herein may be readily applied to storage systems and devices that utilize polynucleotides that are not necessarily in the form of DNA. The invention is thus not limited to using DNA as the only kind of polynucleotides for storage as described herein. Moreover, polynucleotides are only one example of biological material that may be used for storage as described herein.

Examples of how digital information may be stored in DNA are disclosed in U.S. Pub. No. 2015/0261664, entitled "High-Capacity of Storage of Digital Information in DNA," published Sep. 17, 2015, which is incorporated by reference herein in its entirety. For example, methods from code theory to enhance the recoverability of the encoded messages from the DNA segment, including forbidding DNA homopolymers (i.e. runs of more than one identical base) that are known to be associated with higher error rates in existing high throughput technologies may be used. Further, an error-detecting component, analogous to a parity-check bit, may be integrated into the indexing information in the code. More complex schemes, including but not limited to error-correcting codes and, indeed, substantially any form of digital data security (e.g., RAID-based schemes) currently employed in informatics, may be implemented in future developments of the DNA storage scheme. The DNA encoding of information may be computed using software. The bytes comprising each computer file may be represented by a DNA sequence with no homopolymers by an encoding scheme to produce an encoded file that replaces each byte by five or six bases forming the DNA sequence.

The code used in the encoding scheme may be constructed to permit a straightforward encoding that is close to the optimum information capacity for a run length-limited channel (e.g., no repeated nucleotides), though other encoding schemes may be used. The resulting in silico DNA sequences may be too long to be readily produced by standard oligonucleotide synthesis and may be split into overlapping segments of a length of 100 bases with an overlap of 75 bases. To reduce the risk of systematic synthesis errors introduced to any particular run of bases, alternate ones of the segments may be converted to their reverse complement, meaning that each base may be "written" four times, twice in each direction. Each segment may then be augmented with an indexing information that permits determination of the computer file from which the segment originated and its location within that computer file, plus simple error-detection information. This indexing information may also be encoded in as non-repeating DNA nucleotides and appended to the information storage bases of the DNA segments. The division of the DNA segments into lengths of 100 bases with an overlap of 75 bases is purely arbitrary and illustrative, and it is understood that other lengths and overlaps may be used and is not limiting.

Other encoding schemes for the DNA segments may be used, for example to provide enhanced error-correcting properties. The amount of indexing information may be increased in order to allow more or larger files to be encoded. One extension to the coding scheme in order to avoid systematic patterns in the DNA segments may to add change the information. One way may use the "shuffling" of information in the DNA segments, where the information may be retrieved if one knows the pattern of shuffling. Different patterns of shuffles may be used for different ones of the DNA segments. A further way is to add a degree of randomness into the information in each one of the DNA segments. A series of random digits may be used for this, using modular addition of the series of random digits and the digits comprising the information encoded in the DNA segments. The information may be retrieved by modular subtraction during decoding if one knows the series of random digits used. Different series of random digits may be used for different ones of the DNA segments The data-encoding component of each string may contain Shannon information at 5.07 bits per DNA base, which is close to the theoretical optimum of 5.05 bits per DNA base for base-4 channels with run length limited to one. The indexing implementation may permit $3^{14}=4782969$ unique data locations. Increasing the number of indexing trits (and therefore bases) used to specify file and intra-file location by just two, to 16, gives $3^{16}=43046721$ unique locations, in excess of the 16.8M that is the practical maximum for the Nested Primer Molecular Memory (NPMM) scheme.

The DNA segment designs may be synthesized in three distinct runs (with the DNA segments randomly assigned to runs) to create approx. $1.2\times10^7$ copies of each DNA segment design. Phosphoramidite chemistry may be used, and inkjet printing and flow cell reactor technologies in an in-situ microarray synthesis platform may be employed. The inkjet printing within an anhydrous chamber may allow the delivery of very small volumes of phosphoramidites to a confined coupling area on a 2D planar surface, resulting in the addition of hundreds of thousands of bases in parallel. Subsequent oxidation and detritylation may be carried out in a flow cell reactor. Once DNA synthesis is completed, the oligonucleotides may then be cleaved from the surface and deprotected.

Adapters may then be added to the DNA segments to enable a plurality of copies of the DNA segments to be made. A DNA segment with no adapter may require additional chemical processes to "kick start" the chemistry for the synthesis of the multiple copies by adding additional groups onto the ends of the DNA segments. Oligonucleotides may be amplified using polymerase chain reaction (PCR) methods and paired-end PCR primers, followed by bead purification and quantification. Oligonucleotides may then be sequenced to produce reads of 104 bases. The digital information decoding may then be carried out via sequencing of the central bases of each oligo from both ends and rapid computation of full-length oligos and removal of sequence reads inconsistent with the designs. Sequence reads may be decoded using computer software that exactly reverses the encoding process. Sequence reads for which the parity-check trit indicates an error or that may be unambiguously decoded or assigned to a reconstructed computer file may be discarded. Locations within every decoded file may be detected in multiple different sequenced DNA oligos, and simple majority voting may be used to resolve any discrepancies caused by the DNA synthesis or the sequencing errors.

While several examples herein are provided in the context of machine-written DNA, it is contemplated that the principles described herein may be applied to other kinds of machine-written biological material.

As used herein, the term "machine-written DNA" shall be read to include one or more strands of polynucleotides that are generated by a machine, or otherwise modified by a machine, to store data or other information. One example of the polynucleotide herein is a DNA. It is noted that while the term "DNA" in the context of DNA being read or written is used throughout this disclosure, the term is used only as a representative example of a polynucleotide and may encompass the concept of a polynucleotide. "Machine," as used herein in reference to "machine-written," may include an instrument or system specially designed for writing DNA as described in greater detail herein. The system may be non-biological or biological. In one example, the biological system may comprise, or is, a polymerase. For example, the polymerase may be terminal deoxynucleotidyl transferase (TdT). In a biological system, the process may be additionally controlled by a machine hardware (e.g., processor) or an algorithm. "Machine-written DNA" may include any polynucleotide having one or more base sequences written by a machine. While machine-written DNA is used herein as an example, other polynucleotide strands may be substituted for machine-written DNA described herein. "Machine-written DNA" may include natural bases and modifications of natural bases, including but not limited to bases modified with methylation or other chemical tags; an artificially synthesized polymer that is similar to DNA, such as peptide nucleic acid (PNA); or Morpholino DNA. "Machine-written DNA" may also include DNA strands or other polynucleotides that are formed by at least one strand of bases originating from nature (e.g., extracted from a naturally occurring organism), with a machine-written strand of bases secured thereto either in a parallel fashion or in an end-to-end fashion. In other implementations, "machine-written DNA" may be written by a biological system (e.g., enzyme) in lieu of, or in addition to, a non-biological system (e.g., the electrode machine) writing of DNA described herein. In other words, "machine-written DNA" may be written directly by a machine; or by an enzyme (e.g., polymerase) that is controlled by an algorithm and/or machine.

"Machine-written DNA" may include data that have been converted from a raw form (e.g., a photograph, a text document, etc.) into a binary code sequence using known techniques, with that binary code sequence then being converted to a DNA base sequence using known techniques, and with that DNA base sequence then being generated by a machine in the form of one or more DNA strands or other polynucleotides. Alternatively, "machine-written DNA" may be generated to index or otherwise track pre-existing DNA, to store data or information from any other source and for any suitable purpose, without necessarily requiring an intermediate step of converting raw data to a binary code.

As described in greater detail below, machine-written DNA may be written to and/or read from a reaction site. As used herein, the term "reaction site" is a localized region where at least one designated reaction may occur. A reaction site may include support surfaces of a reaction structure or substrate where a substance may be immobilized thereon. For instance, the reaction site may be a discrete region of space where a discrete group of DNA strands or other polynucleotides are written. The reaction site may permit chemical reactions that are isolated from reactions that are in adjacent reaction sites. Devices that provide machine-writing of DNA may include flow cells with wells having writing features (e.g., electrodes) and/or reading features. In some instances, the reaction site may include a surface of a reaction structure (which may be positioned in a channel of a flow cell) that already has a reaction component thereon, such as a colony of polynucleotides thereon. In some flow cells, the polynucleotides in the colony have the same sequence, being for example, clonal copies of a single stranded or double stranded template. However, in some flow cells a reaction site may contain only a single polynucleotide molecule, for example, in a single stranded or double stranded form.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

To read the machine-written DNA, one or more discrete detectable regions of reaction sites may be defined. Such detectable regions may be imageable regions, electrical detection regions, or other types of regions that may have a measurable change in a property (or absence of change in the property) based on the type of nucleotide present during the reading process.

As used herein, the term "pixel" refers to a discrete imageable region. Each imageable region may include a compartment or discrete region of space where a polynucleotide is present. In some instances, a pixel may include two or more reaction sites (e.g., two or more reaction chambers, two or more reaction recesses, two or more wells, etc.). In some other instances, a pixel may include just one reaction site. Each pixel is detected using a corresponding detection device, such as an image sensor or other light detection device. The light detection device may be manufactured using integrated circuit manufacturing processes, such as processes used to manufacture charged-coupled devices circuits (CCD) or complementary-metal-oxide semiconductor (CMOS) devices or circuits. The light detection device may thereby include, for example, one or more semiconductor materials, and may take the form of, for example, a CMOS light detection device (e.g., a CMOS image sensor) or a CCD image sensor, another type of image sensor. A CMOS image sensor may include an array of light sensors (e.g. photodiodes). In one implementation, a single image sensor may be used with an objective lens to capture several "pixels," during an imaging event. In some other implementations, each discrete photodiode or light sensor may capture a corresponding pixel. In some implementations, light sensors (e.g., photodiodes) of one or more detection devices may be associated with corresponding reaction sites. A light sensor that is associated with a reaction site may detect light emissions from the associated reaction site. In some implementations, the detection of light emissions may be done via at least one light guide when a designated reaction has occurred at the associated reaction site. In some implementations, a plurality of light sensors (several pixels of a light detection or camera device) may be associated with a single reaction site. In some implementations, a single light sensor (e.g. a single pixel) may be associated with a single reaction site or with a group of reaction sites.

As used herein, the term "synthesis" shall be read to include processes where DNA is generated by a machine to store data or other information. Thus, machine-written DNA may constitute synthesized DNA. As used herein, the terms "consumable cartridge," "reagent cartridge," "removeable cartridge," and/or "cartridge" refer to the same cartridge and/or a combination of components making an assembly for a cartridge or cartridge system. The cartridges described herein may be independent of the element with the reaction sites, such as a flow cell having a plurality of wells. In some instances, a flow cell may be removably inserted into a cartridge, which is then inserted into an instrument. In some other implementations, the flow cell may be removably inserted into the instrument without a cartridge. As used herein, the term "biochemical analysis" may include at least one of biological analysis or chemical analysis.

The term "based on" should be understood to mean that something is determined at least in part by the thing it is indicated as being "based on." To indicate that something must necessarily be completely determined by something else, it is described as being based exclusively on Whatever it is completely determined by.

The term "non-nucleotide memory" should be understood to refer to an object, device or combination of devices capable of storing data or instructions in a form other than nucleotides that may be retrieved and/or processed by a device. Examples of "non-nucleotide memory" include solid state memory, magnetic memory, hard drives, optical drives and combinations of the foregoing (e.g., magneto-optical storage elements).

The term "DNA storage device" should be understood to refer to an object, device, or combination of devices configured to store data or instructions in the form of sequences of polynucleotides such as machine-written DNA. Examples of "DNA storage devices" include flow cells having addressable wells as described herein, systems comprising multiple such flow cells, and tubes or other containers storing nucleotide sequences that have been cleaved from the surface on which they were synthesized. As used herein, the term "nucleotide sequence" or "polynucleotide sequence" should be read to include a polynucleotide molecule, as well as the underlying sequence of the molecule, depending on context. A sequence of a polynucleotide may contain (or encode) information indicative of certain physical characteristics.

Implementations set forth herein may be used to perform designated reactions for consumable cartridge preparation and/or biochemical analysis and/or synthesis of machine-written DNA.

I. System Overview

FIG. 1 is a schematic diagram of a system 100 that is configured to conduct biochemical analysis and/or synthesis. The system 100 may include a base instrument 102 that is configured to receive and separably engage a removable cartridge 200 and/or a component with one or more reaction sites. The base instrument 102 and the removable cartridge 200 may be configured to interact with each other to transport a biological material to different locations within the system 100 and/or to conduct designated reactions that include the biological material in order to prepare the biological material for subsequent analysis (e.g., by synthesizing the biological material), and, optionally, to detect one or more events with the biological material. In some implementations, the base instrument 102 may be configured to detect one or more events with the biological material directly on the removable cartridge 200. The events may be indicative of a designated reaction with the biological material. The removable cartridge 200 may be constructed according to any of the cartridges described herein.

Although the following is with reference to the base instrument 102 and the removable cartridge 200 as shown in FIG. 1, it is understood that the base instrument 102 and the removable cartridge 200 illustrate only one implementation of the system 100 and that other implementations exist. For example, the base instrument 102 and the removable cartridge 200 include various components and features that, collectively, execute several operations for preparing the biological material and/or analyzing the biological material. Moreover, although the removable cartridge 200 described herein includes an element with the reaction sites, such as a flow cell having a plurality of wells, other cartridges may be independent of the element with the reaction sites and the element with the reaction sites may be separately insertable into the base instrument 102. That is, in some instances a flow cell may be removably inserted into the removable cartridge 200, which is then inserted into the base instrument 102. In some other implementations, the flow cell may be removably inserted directly into the base instrument 102 without the removable cartridge 200. In still further implementations, the flow cell may be integrated into the removable cartridge 200 that is inserted into the base instrument 102.

In the illustrated implementation, each of the base instrument 102 and the removable cartridge 200 are capable of performing certain functions. It is understood, however, that the base instrument 102 and the removable cartridge 200 may perform different functions and/or may share such functions. For example, the base instrument 102 is shown to include a detection assembly 110 (e.g., an imaging device) that is configured to detect the designated reactions at the removable cartridge 200. In alternative implementations, the removable cartridge 200 may include the detection assembly and may be communicatively coupled to one or more components of the base instrument 102. As another example, the base instrument 102 is a "dry" instrument that does not provide, receive, or exchange liquids with the removable cartridge 200. That is, as shown, the removable cartridge 200 includes a consumable reagent portion 210 and a flow cell receiving portion 220. The consumable reagent portion 210 may contain reagents used during biochemical analysis and/or synthesis. The flow cell receiving portion 220 may include an optically transparent region or other detectable region for the detection assembly 110 to perform detection of one or more events occurring within the flow cell receiving portion 220. In alternative implementations, the base instrument 102 may provide, for example, reagents or other liquids to the removable cartridge 200 that are subsequently consumed (e.g., used in designated reactions or synthesis procedures) by the removable cartridge 200.

As used herein, the biological material may include one or more biological or chemical substances, such as nucleosides, nucleotides, nucleic acids, polynucleotides, oligonucleotides, proteins, enzymes, peptides, oligopeptides, polypeptides, antibodies, antigens, ligands, receptors, polysaccharides, carbohydrates, polyphosphates, nanopores, organelles, lipid layers, cells, tissues, organisms, and/or biologically active chemical compound(s), such as analogs or mimetics of the aforementioned species. In some instances, the biological material may include whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, viruses including viral pathogens, liquids containing multi-celled organisms, biological swabs and biological washes. In some instances, the biological material may include a set of synthetic sequences, including but not limited to machine-written DNA, which may be fixed (e.g., attached in specific wells in a cartridge) or unfixed (e.g., stored in a tube).

In some implementations, the biological material may include an added material, such as water, deionized water, saline solutions, acidic solutions, basic solutions, detergent solutions and/or pH buffers. The added material may also include reagents that will be used during the designated assay protocol to conduct the biochemical reactions. For example, added liquids may include material to conduct multiple polymerase-chain-reaction (PCR) cycles with the biological material. In other aspects, the added material may be a carrier for the biological material such as cell culture media or other buffered and/or pH adjusted and/or isotonic carrier that may allow for or preserve the biological function of the biological material.

It should be understood, however, that the biological material that is analyzed may be in a different form or state than the biological material loaded into or created by the system 100. For example, a biological material loaded into the system 100 may include whole blood or saliva or cell population that is subsequently treated (e.g., via separation or amplification procedures) to provide prepared nucleic acids. The prepared nucleic acids may then be analyzed (e.g., quantified by PCR or sequenced by SBS) by the system 100. Accordingly, when the term "biological material" is used while describing a first operation, such as PCR, and used again while describing a subsequent second operation, such as sequencing, it is understood that the biological material in the second operation may be modified with respect to the biological material prior to or during the first operation. For example, sequencing (e.g. SBS) may be carried out on amplicon nucleic acids that are produced from template nucleic acids that are amplified in a prior amplification (e.g. PCR). In this case the amplicons are copies of the templates and the amplicons are present in higher quantity compared to the quantity of the templates.

In some implementations, the system 100 may automatically prepare a sample for biochemical analysis based on a substance provided by the user (e.g., whole blood or saliva or a population of cells). However, in other implementations, the system 100 may analyze biological materials that are partially or preliminarily prepared for analysis by the user. For example, the user may provide a solution including nucleic acids that were already isolated and/or amplified from whole blood; or may provide a virus sample in which the RNA or DNA sequence is partially or wholly exposed for processing.

As used herein, a "designated reaction" includes a change in at least one of a chemical, electrical, physical, or optical property (or quality) of an analyte-of-interest. In particular implementations, the designated reaction is an associative binding event (e.g., incorporation of a fluorescently labeled biomolecule with the analyte-of-interest). The designated reaction may be a dissociative binding event (e.g., release of a fluorescently labeled biomolecule from an analyte-of-interest). The designated reaction may be a chemical transformation, chemical change, or chemical interaction. The designated reaction may also be a change in electrical properties. For example, the designated reaction may be a change in ion concentration within a solution. Some reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction may also be addition or removal of a proton, for example, detectable as a change in pH of a surrounding solution or environment. An additional designated reaction may be detecting the flow of ions across a membrane e.g., natural or synthetic bilayer membrane). For example, as ions flow through a membrane, the current is disrupted, and the disruption may be detected. Field sensing of charged tags may also be used; as may thermal sensing and other suitable analytical sensing techniques.

In particular implementations, the designated reaction includes the incorporation of a fluorescently labeled molecule to an analyte. The analyte may be an oligonucleotide and the fluorescently labeled molecule may be a nucleotide. The designated reaction may be detected when an excitation light is directed toward the oligonucleotide having the labeled nucleotide, and the fluorophore emits a detectable fluorescent signal. In alternative implementations, the detected fluorescence is a result of chemiluminescence and/ or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" includes any substance that may be used to obtain a designated reaction. For example, reaction components include reagents, catalysts such as enzymes, reactants for the reaction, samples, products of the reaction, other biomolecules, salts, metal cofactors, chelating agents, and buffer solutions (e.g., hydrogenation buffer). The reaction components may be delivered, individually in solutions or combined in one or more mixture, to various locations in a fluidic network. For instance, a reaction component may be delivered to a reaction chamber where the biological material is immobilized. The reaction components may interact directly or indirectly with the biological material. In some implementations, the removable cartridge 200 is preloaded with one or more of the reaction components involved in carrying out a designated assay protocol. Preloading may occur at one location (e.g. a manufacturing facility) prior to receipt of the cartridge 200 by a user (e.g. at a customer's facility). For example, the one or more reaction components or reagents may be preloaded into the consumable reagent portion 210. In some implementations, the removable cartridge 200 may also be preloaded with a flow cell in the flow cell receiving portion 220.

In some implementations, the base instrument 102 may be configured to interact with one removable cartridge 200 per session. After the session, the removable cartridge 200 may be replaced with another removable cartridge 200. In other implementations, the base instrument 102 may be configured to interact with more than one removable cartridge 200 per session. As used herein, the term "session" includes performing at least one of sample preparation and/or biochemical analysis protocol. Sample preparation may include synthesizing the biological material; and/or separating, isolating, modifying, and/or amplifying one or more components of the biological material so that the prepared biological material is suitable for analysis. In some implementations, a session may include continuous activity in which a number of controlled reactions are conducted until (a) a designated number of reactions have been conducted, (b) a designated number of events have been detected, (c) a designated period of system time has elapsed, (d) signal-to-noise has dropped to a designated threshold; (e) a target component has been identified; (f) system failure or malfunction has been detected; and/or (g) one or more of the resources for conducting the reactions has depleted. Alternatively, a session may include pausing system activity for a period of time (e.g., minutes, hours, days, weeks) and later completing the session until at least one of (a)-(g) occurs.

An assay protocol may include a sequence of operations for conducting the designated reactions, detecting the designated reactions, and/or analyzing the designated reactions. Collectively, the removable cartridge 200 and the base instrument 102 may include the components for executing the different operations. The operations of an assay protocol may include fluidic operations, thermal-control operations, detection operations, and/or mechanical operations.

A fluidic operation includes controlling the flow of fluid (e.g., liquid or gas) through the system 100, which may be actuated by the base instrument 102 and/or by the removable cartridge 200. In one example, the fluid is in liquid form. For example, a fluidic operation may include controlling a pump to induce flow of the biological material or a reaction component into a reaction chamber.

A thermal-control operation may include controlling a temperature of a designated portion of the system 100, such as one or more portions of the removable cartridge 200. By way of example, a thermal-control operation may include raising or lowering a temperature of a polymerase chain reaction (PCR) zone where a liquid that includes the biological material is stored.

A detection operation may include controlling activation of a detector or monitoring activity of the detector to detect predetermined properties, qualities, or characteristics of the biological material. As one example, the detection operation may include capturing images of a designated area that includes the biological material to detect fluorescent emissions from the designated area. The detection operation may include controlling a light source to illuminate the biological material or controlling a detector to observe the biological material.

A mechanical operation may include controlling a movement or position of a designated component. For example, a mechanical operation may include controlling a motor to move a valve-control component in the base instrument 102 that operably engages a movable valve in the removable cartridge 200. In some cases, a combination of different operations may occur concurrently. For example, the detector may capture images of the reaction chamber as the pump controls the flow of fluid through the reaction chamber. In some cases, different operations directed toward different biological materials may occur concurrently. For instance, a first biological material may be undergoing amplification (e.g., PCR) while a second biological material may be undergoing detection.

Similar or identical fluidic elements (e.g., channels, ports, reservoirs, etc.) may be labeled differently to more readily distinguish the fluidic elements. For example, ports may be referred to as reservoir ports, supply ports, network ports, feed port, etc. It is understood that two or more fluidic elements that are labeled differently (e.g., reservoir channel, sample channel, flow channel, bridge channel) do not require that the fluidic elements be structurally different. Moreover, the claims may be amended to add such labels to more readily distinguish such fluidic elements in the claims.

A "liquid," as used herein, is a substance that is relatively incompressible and has a capacity to flow and to conform to a shape of a container or a channel that holds the substance. A liquid may be aqueous-based and include polar molecules exhibiting surface tension that holds the liquid together. A liquid may also include non-polar molecules, such as in an oil-based or non-aqueous substance. It is understood that references to a liquid in the present application may include a liquid comprising the combination of two or more liquids. For example, separate reagent solutions may be later combined to conduct designated reactions.

One or more implementations may include retaining the biological material (e.g., template nucleic acid) at a designated location where the biological material is analyzed. As used herein, the term "retained," when used with respect to a biological material, includes attaching the biological material to a surface or confining the biological material within a designated space. As used herein, the term "immobilized," when used with respect to a biological material, includes attaching the biological material to a surface in or on a solid support. Immobilization may include attaching the biological material at a molecular level to the surface. For example, a biological material may be immobilized to a surface of a substrate using adsorption techniques including non-covalent interactions (e.g., electrostatic forces, van der Waals, and dehydration of hydrophobic interfaces) and covalent binding techniques where functional groups or linkers facilitate attaching the biological material to the surface. Immobilizing a biological material to a surface of a substrate may be based upon the properties of the surface of the substrate, the liquid medium carrying the biological material, and the properties of the biological material itself. In some cases, a substrate surface may be functionalized (e.g., chemically or physically modified) to facilitate immobilizing the biological material to the substrate surface. The substrate surface may be first modified to have functional groups bound to the surface. The functional groups may then bind to the biological material to immobilize the biological material thereon. In some cases, a biological material may be immobilized to a surface via a gel.

In some implementations, nucleic acids may be immobilized to a surface and amplified using bridge amplification. Another useful method for amplifying nucleic acids on a surface is rolling circle amplification (RCA), for example, using methods set forth in further detail below. In some implementations, the nucleic acids may be attached to a surface and amplified using one or more primer pairs. For example, one of the primers may be in solution and the other primer may be immobilized on the surface (e.g., 5'-attached). By way of example, a nucleic acid molecule may hybridize to one of the primers on the surface followed by extension of the immobilized primer to produce a first copy of the nucleic acid. The primer in solution then hybridizes to the first copy of the nucleic acid which may be extended using the first copy of the nucleic acid as a template. Optionally, after the first copy of the nucleic acid is produced, the original nucleic acid molecule may hybridize to a second immobilized primer on the surface and may be extended at the same time or after the primer in solution is extended. In any implementation, repeated rounds of extension (e.g., amplification) using the immobilized primer and primer in solution may be used to provide multiple copies of the nucleic acid. In some implementations, the biological material may be confined within a predetermined space with reaction components that are configured to be used during amplification of the biological material (e.g., PCR).

One or more implementations set forth herein may be configured to execute an assay protocol that is or includes an amplification (e.g., PCR) protocol. During the amplification protocol, a temperature of the biological material within a reservoir or channel may be changed in order to amplify a target sequence or the biological material (e.g., DNA of the biological material). By way of example, the biological material may experience (1) a pre-heating stage of about 95° C. for about 75 seconds; (2) a denaturing stage of about 95° C. for about 15 seconds; (3) an annealing-extension stage of about of about 59° C. for about 45 seconds; and (4) a temperature holding stage of about 72° C. for about 60 seconds. Implementations may execute multiple amplification cycles. It is noted that the above cycle describes only one particular implementation and that alternative implementations may include modifications to the amplification protocol.

The methods and systems set forth herein may use arrays having features at any of a variety of densities including, for example, at least about 10 features/cm$^2$, about 100 features/cm$^2$, about 500 features/cm$^2$, about 1,000 features/cm$^2$, about 5,000 features/cm$^2$, about 10,000 features/cm$^2$, about 50,000 features/cm$^2$, about 100,000 features/cm$^2$, about 1,000,000 features/cm$^2$, about 5,000,000 features/cm$^2$, or higher. The methods and apparatus set forth herein may include detection components or devices having a resolution that is at least sufficient to resolve individual features at one or more of these densities.

The base instrument 102 may include a user interface 130 that is configured to receive user inputs for conducting a designated assay protocol and/or configured to communicate information to the user regarding the assay. The user interface 130 may be incorporated with the base instrument 102. For example, the user interface 130 may include a touchscreen that is attached to a housing of the base instrument 102 and configured to identify a touch from the user and a location of the touch relative to information displayed on the touchscreen. Alternatively, the user interface 130 may be located remotely with respect to the base instrument 102.

II. Cartridge

The removable cartridge 200 is configured to separably engage or removably couple to the base instrument 102 at a cartridge chamber 140. As used herein, when the terms "separably engaged" or "removably coupled" (or the like) are used to describe a relationship between a removable cartridge 200 and a base instrument 102. The term is intended to mean that a connection between the removable cartridge 200 and the base instrument 102 are separable without destroying the base instrument 102. Accordingly, the removable cartridge 200 may be separably engaged to the base instrument 102. In an electrical manner such that the electrical contacts of the base instrument 102 are not destroyed. The removable cartridge 200 may be separably engaged to the base instrument 102 in a mechanical manner such that features of the base instrument 102 that hold the removable cartridge 200, such as the cartridge chamber 140, are not destroyed. The removable cartridge 200 may be separably engaged to the base instrument 102 in a fluidic manner such that the ports of the base instrument 102 are not destroyed. The base instrument 102 is not considered to be "destroyed," for example, if only a simple adjustment to the component (e.g., realigning) or a simple replacement (e.g., replacing a nozzle) is required. Components (e.g., the removable cartridge 200 and the base instrument 102) may be readily separable when the components may be separated from each other without undue effort or a significant amount of time spent in separating the components. In some implementations, the removable cartridge 200 and the base instrument 102 may be readily separable without destroying either the removable cartridge 200 or the base instrument 102.

In some implementations, the removable cartridge 200 may be permanently modified or partially damaged during a session with the base instrument 102. For instance, containers holding liquids may include foil covers that are pierced to permit the liquid to flow through the system 100. In such implementations, the foil covers may be damaged such that the damaged container is to be replaced with another container. In particular implementations, the removable cartridge 200 is a disposable cartridge such that the removable cartridge 200 may be replaced and optionally disposed after a single use. Similarly, a flow cell of the removable cartridge 200 may be separately disposable such that the flow cell may be replaced and optionally disposed after a single use.

In other implementations, the removable cartridge 200 may be used for more than one session while engaged with the base instrument 102 and/or may be removed from the base instrument 102, reloaded with reagents, and re-engaged to the base instrument 102 to conduct additional designated reactions. Accordingly, the removable cartridge 200 may be refurbished in some cases such that the same removable cartridge 200 may be used with different consumables (e.g., reaction components and biological materials). Refurbishing may be carried out at a manufacturing facility after the cartridge 200 has been removed from a base instrument 102 located at a customer's facility.

The cartridge chamber 140 may include a slot, mount, connector interface, and/or any other feature to receive the removable cartridge 200 or a portion thereof to interact with the base instrument 102.

The removable cartridge 200 may include a fluidic network that may hold and direct fluids (e.g., liquids or gases) therethrough. The fluidic network may include a plurality of interconnected fluidic elements that are capable of storing a fluid and/or permitting a fluid to flow therethrough. Non-limiting examples of fluidic elements include channels, ports of the channels, cavities, storage devices, reservoirs of the storage devices, reaction chambers, waste reservoirs, detection chambers, multipurpose chambers for reaction and detection, and the like. For example, the consumable reagent portion 210 may include one or more reagent wells or chambers storing reagents and may be part of or coupled to the fluidic network. The fluidic elements may be fluidically coupled to one another in a designated manner so that the system 100 is capable of performing sample preparation and/or analysis.

As used herein, the term "fluidically coupled" (or like term) refers to two spatial regions being connected together such that a liquid or gas may be directed between the two spatial regions. In some cases, the fluidic coupling permits a fluid to be directed back and forth between the two spatial regions. In other cases, the fluidic coupling is uni-directional such that there is only one direction of flow between the two spatial regions. For example, an assay reservoir may be fluidically coupled with a channel such that a liquid may be transported into the channel from the assay reservoir. However, in some implementations, it may not be possible to direct the fluid in the channel back to the assay reservoir. In particular implementations, the fluidic network may be configured to receive a biological material and direct the biological material through sample preparation and/or sample analysis. The fluidic network may direct the biological material and other reaction components to a waste reservoir.

Figure 2:
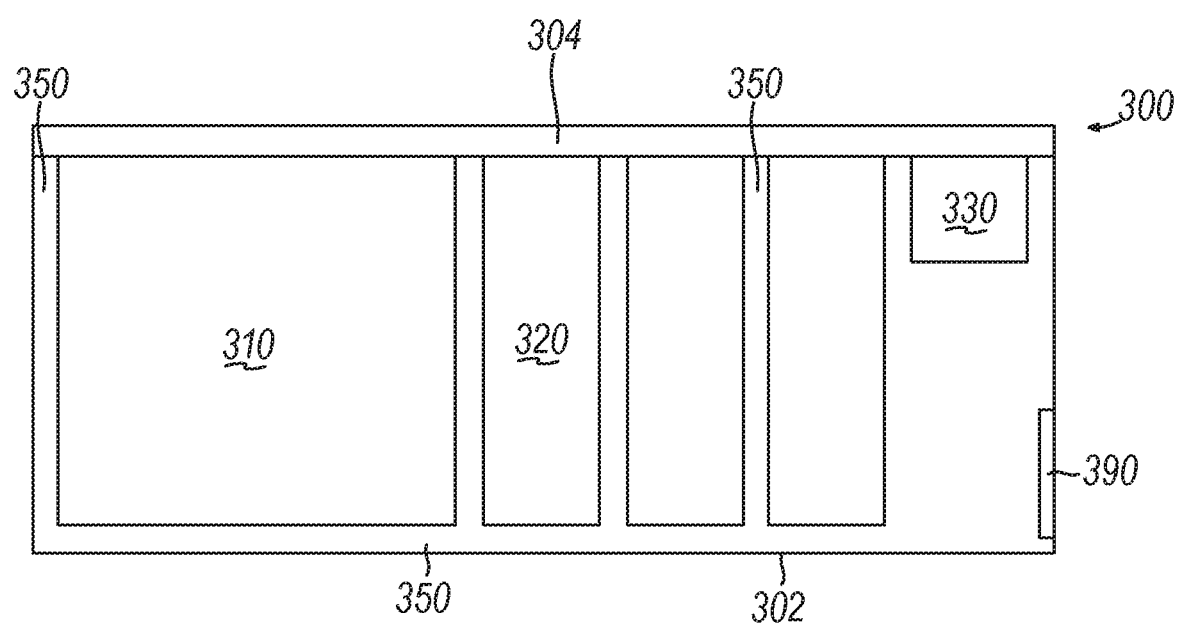
FIG. 2 depicts a block schematic cross-sectional view of an example of a consumable cartridge that may be utilized with the system of FIG. 1.

FIG. 2 depicts an implementation of a consumable cartridge 300. The consumable cartridge may be part of a combined removable cartridge, such as consumable reagent portion 210 of removable cartridge 200 of FIG. 1; or may be a separate reagent cartridge. The consumable cartridge 300 may include a housing 302 and a top 304. The housing 302 may comprise a non-conductive polymer or other material and be formed to make one or more reagent chambers 310, 320, 330. The reagent chambers 310, 320, 330 may be varying in size to accommodate varying volumes of reagents to be stored therein. For instance, a first chamber 310 may be larger than a second chamber 320, and the second chamber 320 may be larger than a third chamber 330. The first chamber 310 is sized to accommodate a larger volume of a particular reagent, such as a buffer reagent. The second chamber 320 may be sized to accommodate a smaller volume of reagent than the first chamber 310, such as a reagent chamber holding a cleaving reagent. The third chamber 330 may be sized to accommodate an even smaller volume of reagent than the first chamber 310 and the second chamber 320, such as a reagent chamber holding a fully functional nucleotide containing reagent.

In the illustrated implementation, the housing 302 has a plurality of housing walls or sides 350 forming the chambers 310, 320, 330 therein. In the illustrated implementation, the housing 302 forms a structure that is at least substantially unitary or monolithic. In alternative implementations, the housing 302 may be constructed by one or more sub-components that are combined to form the housing 302, such as independently formed compartments for chambers 310, 320, and 330.

The housing 302 may be sealed by the top 304 once reagents are provided into the respective chambers 310, 320, 330, The top 304 may comprise a conductive or non-conductive material. For instance, the top 304 may be an aluminum foil seal that is adhesively coupled to top surfaces of the housing 302 to seal the reagents within their respective chambers 310, 320, 330. In other implementations, the top 304 may be a plastic seal that is adhesively coupled to top surfaces of the housing 302 to seal the reagents within their respective chambers 310, 320, 330.

In some implementations, the housing 302 may also include an identifier 390. The identifier 390 may be a radio-frequency identification (RFID) transponder, a bar-code, an identification chip, and/or other identifier. In some implementations, the identifier 390 may be embedded in the housing 302 or attached to an exterior surface. The identifier 390 may include data for a unique identifier for the consumable cartridge 300 and/or data for a type of the consumable cartridge 300. The data of the identifier 390 may be read by the base instrument 102 or a separate device configured for warming the consumable cartridge 300, as described herein.

In some implementations, the consumable cartridge 300 may include other components, such as valves, pumps, fluidic lines, ports, etc. In some implementations, the consumable cartridge 300 may be contained within a further exterior housing.

III. System Controller

The base instrument 102 may also include a system controller 120 that is configured to control operation of at least one of the removable cartridge 200 and/or the detection assembly 110. The system controller 120 may be implemented utilizing any combination of dedicated hardware circuitry, boards, DSPs, processors, etc. Alternatively, the system controller 120 may be implemented utilizing an off-the-shelf PC with a single processor or multiple processors, with the functional operations distributed between the processors. As a further option, the system controller 120 may be implemented utilizing a hybrid configuration in which certain modular functions are performed utilizing dedicated hardware, while the remaining modular functions are performed utilizing an off-the-shelf PC and the like.

The system controller 120 may include a plurality of circuitry modules that are configured to control operation of certain components of the base instrument 102 and/or the removable cartridge 200. The term "module" herein may refer to a hardware device configured to perform specific task(s). For instance, the circuitry modules may include a flow-control module that is configured to control flow of fluids through the fluidic network of the removable cartridge 200. The flow-control module may be operably coupled to valve actuators and/or s system pump. The flow-control module may selectively activate the valve actuators and/or the system pump to induce flow of fluid through one or more paths and/or to block flow of fluid through one or more paths.

The system controller 120 may also include a thermal-control module. The thermal-control module may control a thermocycler or other thermal component to provide and/or remove thermal energy from a sample-preparation region of the removable cartridge 200 and/or any other region of the removeable cartridge 200. In one particular example, a thermocycler may increase and/or decrease a temperature that is experienced by the biological material in accordance with a PCR protocol.

The system controller 120 may also include a detection module that is configured to control the detection assembly 110 to obtain data regarding the biological material. The detection module may control operation of the detection assembly 110 either through a direct wired connection or through the contact array if the detection assembly 110 is part of the removable cartridge 200. The detection module may control the detection assembly 110 to obtain data at predetermined times or for predetermined time periods. By way of example, the detection module may control the detection assembly 110 to capture an image of a reaction chamber of the flow cell receiving portion 220 of the removable cartridge when the biological material has a fluorophore attached thereto. In some implementations, a plurality of images may be obtained.

Optionally, the system controller 120 may include an analysis module that is configured to analyze the data to provide at least partial results to a user of the system 100. For example, the analysis module may analyze the imaging data provided by the detection assembly 110. The analysis may include identifying a sequence of nucleic acids of the biological material.

The system controller 120 and/or the circuitry modules described above may include one or more logic-based devices, including one or more microcontrollers, processors, reduced instruction set computers (RISC), application specific integrated circuits (ASICs), field programmable gate array (FPGAs), logic circuits, and any other circuitry capable of executing functions described herein. In an implementation, the system controller 120 and/or the circuitry modules execute a set of instructions that are stored in a computer- or machine-readable medium therein in order to perform one or more assay protocols and/or other operations. The set of instructions may be stored in the form of information sources or physical memory elements within the base instrument 102 and/or the removable cartridge 200. The protocols performed by the system 100 may be used to carry out, for example, machine-writing DNA or otherwise synthesizing DNA (e.g., converting binary data into a DNA sequence and then synthesizing DNA strands or other polynucleotides representing the binary data), quantitative analysis of DNA or RNA, protein analysis, DNA sequencing (e.g., sequencing-by-synthesis (SBS)), sample preparation, and/or preparation of fragment libraries for sequencing.

The set of instructions may include various commands that instruct the system 100 to perform specific operations such as the methods and processes of the various implementations described herein. The set of instructions may be in the form of a software program. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are only examples and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the system 100, processed in response to user inputs, or processed in response to a request made by another processing machine (e.g., a remote request through a communication link).

The system controller 120 may be connected to the other components or sub-systems of the system 100 via communication links, which may be hardwired or wireless. The system controller 120 may also be communicatively connected to off-site systems or servers. The system controller 120 may receive user inputs or commands, from a user interface 130. The user interface 130 may include a keyboard, mouse, a touch-screen panel, and/or a voice recognition system, and the like.

The system controller 120 may serve to provide processing capabilities, such as storing, interpreting, and/or executing software instructions, as well as controlling the overall operation of the system 100. The system controller 120 may be configured and programmed to control data and/or power aspects of the various components. Although the system controller 120 is represented as a single structure in FIG. 1, it is understood that the system controller 120 may include multiple separate components (e.g., processors) that are distributed throughout the system 100 at different locations. In some implementations, one or more components may be integrated with the base instrument 102 and one or more components may be located remotely with respect to the base instrument 102.

IV. Flow Cell

Figure 3:
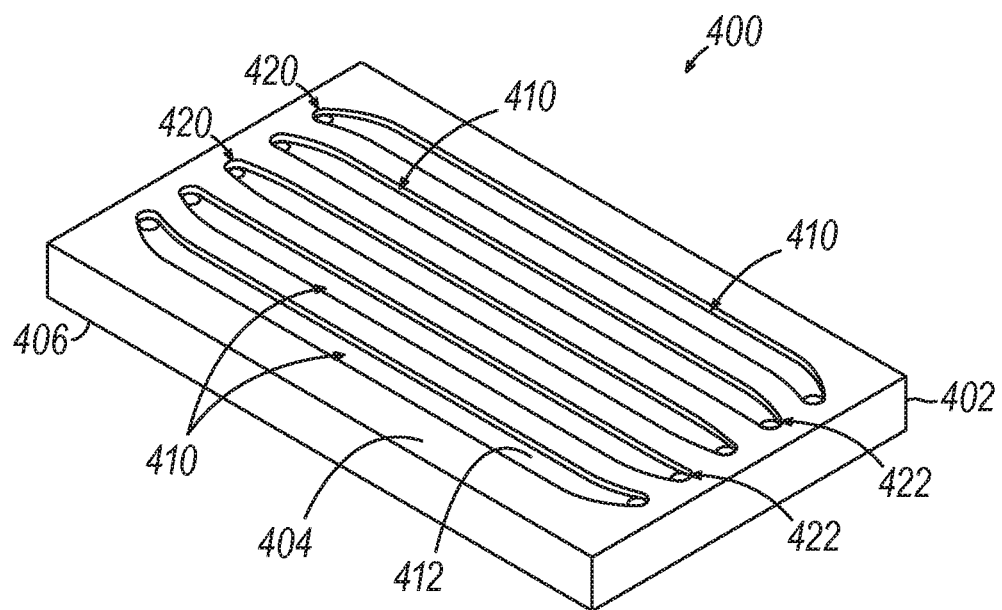
FIG. 3 depicts a perspective view of an example of a flow cell that may be utilized with the system of FIG. 1.
Figure 4:
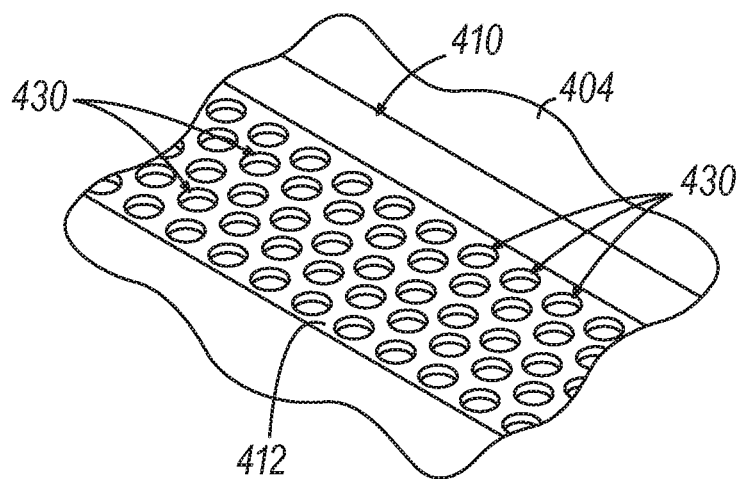
FIG. 4 depicts an enlarged perspective view of a channel of the flow cell of FIG. 3.

FIGS. 3-4 depict an example of a flow cell 400 that may be used with system 100. Flow cell of this example includes a body defining a plurality of elongate flow channels 410, which are recessed below an upper surface 404 of the body 402. The flow channels 410 are generally parallel with each other and extend along substantially the entire length of body 402. While five flow channels 410 are shown, a flow cell 400 may include any other suitable number of flow channels 410, including more or fewer than five flow channels 410. The flow cell 400 of this example also includes a set of inlet ports 420 and a set of outlet ports 422, with each port 420, 422 being associated with a corresponding flow channel 410. Thus, each inlet port 420 may be utilized to communicate fluids (e.g., reagents, etc.) to the corresponding channel 410; while each outlet port 422 may be utilized to communicate fluids from the corresponding flow channel 410.

In some versions, the flow cell 400 is directly integrated into the flow cell receiving portion 220 of the removable cartridge 200. In some other versions, the flow cell 400 is removably coupled with the flow cell receiving portion 220 of the removable cartridge 200. In versions where the flow cell 400 is either directly integrated into the flow cell receiving portion 220 or removably coupled with the flow cell receiving portion 220, the flow channels 410 of the flow cell 400 may receive fluids from the consumable reagent portion 210 via the inlet ports 420, which may be fluidly coupled with reagents stored in the consumable reagent portion 210. Of course, the flow channels 410 may be coupled with various other fluid sources or reservoirs, etc., via the ports 420, 422, As another illustrative variation, some versions of consumable cartridge 300 may be configured to removably receive or otherwise integrate the flow cell 400. In such versions, the flow channels 410 of the flow cell 400 may receive fluids from the reagent chambers 310, 320, 330 via the inlet ports 420. Other suitable ways in which the flow cell 400 may be incorporated into the system 100 will be apparent to those skilled in the art in view of the teachings herein.

FIG. 4 shows a flow channel 410 of the flow cell 400 in greater detail. As shown, the flow channel 410 includes a plurality of wells 430 formed in a base surface 412 of the flow channel 410. As will be described in greater detail below each well 430 is configured to contain DNA strands or other polynucleotides, such as machine-written polynucleotides. In some versions, each well 430 has a cylindraceous configuration, with a generally circular cross-sectional profile. In some other versions, each well 430 has a polygonal (e.g., hexagonal, octagonal, etc.) cross-sectional profile. Alternatively, wells 430 may have any other suitable configuration. It should also be understood that wells 430 may be arranged in any suitable pattern, including but not limited to a grid pattern.

Figure 5:
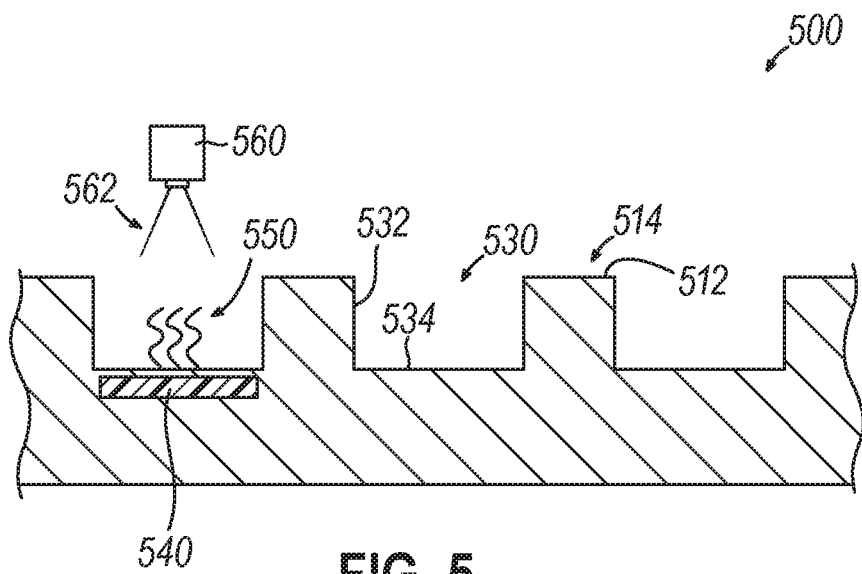
FIG. 5 depicts a block schematic cross-sectional view of an example of wells that may be incorporated into the channel of FIG. 4.

FIG. 5 shows a portion of a channel within a flow cell 500 that is an example of a variation of the flow cell 400. In other words, the channel depicted in FIG. 5 is a variation of the flow channel 410 of the flow cell 400. This flow cell 500 is operable to read polynucleotide strands 550 that are secured to the floor 534 of wells 530 in the flow cell 500. By way of example only, the floor 534 where polynucleotide strands 550 are secured may include a co-block polymer capped with azido. By way of further example only, such a polymer may comprise a poly(N-(5-azidoacetamidylpentyl)acrylamide-co-acrylamide) (PAZAM) coating provided in accordance with at least some of the teachings of U.S. Pat. No. 9,012,022, entitled "Polymer Coatings," issued Apr. 21, 2015, which is incorporated by reference herein in its entirety. Such a polymer may be incorporated into any of the various flow cells described herein.

In the present example, the wells 530 are separated by interstitial spaces 514 provided by the base surface 512 of the flow cell 500. Each well 530 has a sidewall 532 and a floor 534. The flow cell 500 in this example is operable to provide an image sensor 540 under each well 530. In some versions, each well 530 has at least one corresponding image sensor 540, with the image sensors 540 being fixed in position relative to the wells 530. Each image sensor 540 may comprise a CMOS image sensor, a CCD image sensor, or any other suitable kind of image sensor. By way of example only, each well 530 may have one associated image sensor 540 or a plurality of associated image sensors 540. As another variation, a single image sensor 540 may be associated with two or more wells 530. In some versions, one or more image sensors 540 move relative to the wells 530, such that a single image sensor 540 or single group of image sensors 540 may be moved relative to the wells 530. As yet another variation, the flow cell 500 may be movable in relation to the single image sensor 540 or single group of image sensors 540, which may be at least substantially fixed in position.

Each image sensor 540 may be directly incorporated into the flow cell 500. Alternatively, each image sensor 540 may be directly incorporated into a cartridge such as the removable cartridge 200, with the flow cell 500 being integrated into or otherwise coupled with the cartridge. As yet another illustrative variation, each image sensor 540 may be directly incorporated into the base instrument 102 (e.g., as part of the detection assembly 110 noted above) Regardless of where the image sensor(s) 540 is/are located, the image sensor(s) 540 may be integrated into a printed circuit that includes other components (e.g., control circuitry, etc.). In versions where the one or more image sensors 540 are not directly incorporated into the flow cell 500, the flow cell 500 may include optically transmissive features (e.g., windows, etc.) that allow the one or more image sensors 540 to capture fluorescence emitted by the one or more fluorophores associated with the polynucleotide strands 550 that are secured to the floors 534 of the wells 530 in the flow cell 500 as described in greater detail below. It should also be understood that various kinds of optical elements (e.g., lenses, optical waveguides, etc.) may be interposed between the floors 534 of the wells 530 and the corresponding image sensor(s) 540.

As also shown in FIG. 5, a light source 560 is operable to project light 562 into the well 530. In some versions, each well 530 has at least one corresponding light source 560, with the light sources 560 being fixed in position relative to the wells 530. By way of example only, each well 530 may have one associated light source 560 or a plurality of associated light sources 560. As another variation, a single light source 560 may be associated with two or more wells 530. In some other versions, one or more light sources 560 move relative to the wells 530, such that a single light source 560 or single group of light sources 560 may be moved relative to the wells 530. As yet another variation, the flow cell 500 may be movable in relation to the single light source 560 or single group of light sources 560, which may be substantially fixed in position. By way of example only, each light source 560 may include one or more lasers. In another example, the light source 560 may include one or more diodes.

Each light source 560 may be directly incorporated into the flow cell 500. Alternatively, each light source 560 may be directly incorporated into a cartridge such as the removable cartridge 200, with the flow cell 500 being integrated into or otherwise coupled with the cartridge. As yet another illustrative variation, each light source 560 may be directly incorporated into the base instrument 102 (e.g., as part of the detection assembly 110 noted above). In versions where the one or more light sources 560 are not directly incorporated into the flow cell 500, the flow cell 500 may include optically transmissive features (e.g., windows, etc.) that allow the wells 530 to receive the light emitted by the one or more light source 560, to thereby enable the light to reach the polynucleotide strands 550 that are secured to the floor 534 of the wells 530. It should also be understood that various kinds of optical elements (e.g., lenses, optical waveguides, etc.) may be interposed between the wells 530 and the corresponding light source(s) 560.

Figure 6:
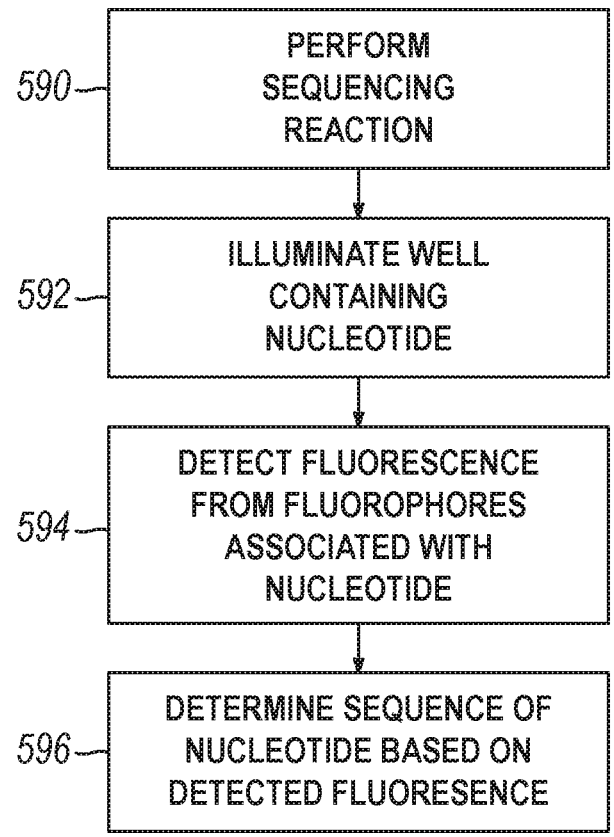
FIG. 6 depicts a flow chart of an example of a process for reading polynucleotides.

As described elsewhere herein and as is shown in block 590 of FIG. 6, a DNA reading process may begin with performing a sequencing reaction in the targeted well(s) 530 (e.g., in accordance with at least some of the teachings of U.S. Pat. No. 9,453,258, entitled "Methods and Compositions for Nucleic Acid Sequencing," issued Sep. 27, 2016, which is incorporated by reference herein in its entirety). Next, as shown in block 592 of FIG. 6, the light source(s) 560 is/are activated over the targeted well(s) 530 to thereby illuminate the targeted well(s) 530. The projected light 562 may cause a fluorophore associated with the polynucleotide strands 550 to fluoresce. Accordingly, as shown in block 594 of FIG. 6, the corresponding image sensor(s) 540 may detect the fluorescence emitted from the one or more fluorophores associated with the polynucleotide strands 550. The system controller 120 of the base instrument 102 may drive the light source(s) 560 to emit the light. The system controller 120 of the base instrument 102 may also process the image data obtained from the image sensor(s) 540, representing the fluorescent emission profiles from the polynucleotide strands 550 in the wells 530. Using this image data from the image sensor(s) 540, and as shown in block 596 of FIG. 6, the system controller 120 may determine the sequence of bases in each polynucleotide strand 550. By way of example only, this process and equipment may be utilized to map a genome or otherwise determine biological information associated with a naturally occurring organism, where DNA strands or other polynucleotides are obtained from or otherwise based on a naturally occurring organism. Alternatively, the above-described process and equipment may be utilized to obtain data stored in machine-written DNA as will be described in greater detail below.

By way of further example only, when carrying out the above-described procedure shown in FIG. 6, time space sequencing reactions may utilize one or more chemistries and imaging events or steps to differentiate between a plurality of analytes (e.g., four nucleotides) that are incorporated into a growing nucleic acid strand during a sequencing reaction; or alternatively, fewer than four different colors may be detected in a mixture having four different nucleotides while still resulting in the determination of the four different nucleotides (e.g., in a sequencing reaction). A pair of nucleotide types may be detected at the same wavelength, but distinguished based on a difference in intensity for one member of the pair compared to the other, or based on a change to one member of the pair (e.g., via chemical modification, photochemical modification, or physical modification) that causes apparent signal to appear or disappear compared to the signal detected for the other member of the pair.

V. Machine-Writing Biological Material

In some implementations, a system 100 such as the system 100 shown in FIG. 1 may be configured to synthesize biological materials (e.g. polynucleotide, such as DNA) to encode data that may later be retrieved through the performance of assays such as those described above. In some implementations, this type of encoding may be performed by assigning values to nucleotide bases (e.g., binary values, such as 0 or 1, ternary values such as 0, 1 or 2, etc.), converting the data to be encoded into a string of the relevant values (e.g., converting a textual message into a binary string using the ASCII encoding scheme), and then creating one or more polynucleotides made up of nucleotides having bases in a sequence corresponding to the string obtained by converting the data.

Figure 7:
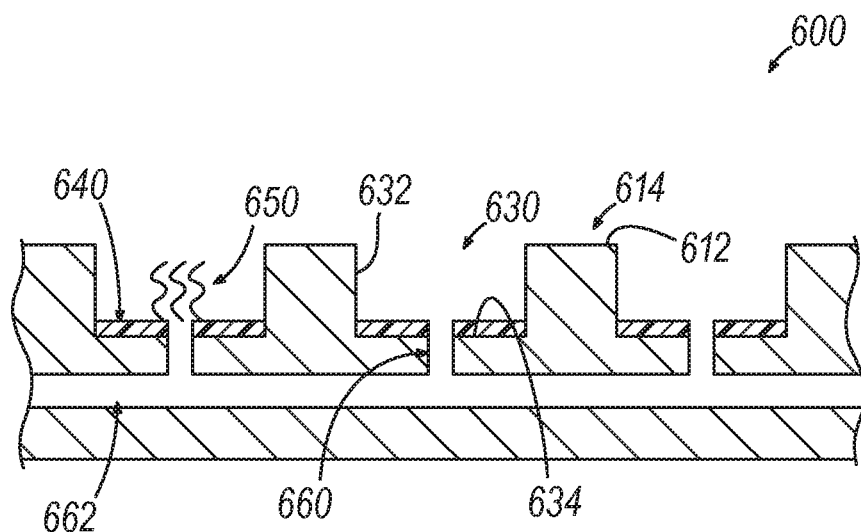
FIG. 7 depicts a block schematic cross-sectional view of another example of wells that may be incorporated into the channel of FIG. 4.

In some implementations, the creation of such polynucleotides may be performed using a version of the flow cell 400 having an array of wells 630 that are configured as shown in FIG. 7. FIG. 7 shows a portion of a channel within a flow cell 600 that is an example of a variation of the flow cell 400. In other words, the channel depicted in FIG. 7 is a variation of the flow channel 410 of the flow cell 400. In this example, each well 630 is recessed below a base surface 612 of the flow cell 600. The wells 630 are thus spaced apart from each other by interstitial spaces 614. By way of example only, the wells 630 may be arranged in a grid or any other suitable pattern along the base surface 612 of the flow cell 600. Each well 630 of this example includes a sidewall 632 and a floor 634. Each well 630 of this example further includes a respective electrode assembly 640 positioned on the floor 634 of the well 630. In some versions, each electrode assembly 640 includes just a single electrode element. In some other versions, each electrode assembly 640 includes a plurality of electrode elements or segments. The terms "electrode" and "electrode assembly" should be read herein as being interchangeable.

Base instrument 102 is operable to independently activate electrode assemblies 640, such that one or more electrode assemblies 640 may be in an activated state while one or more other electrode assemblies 640 are not in an activated state. In some versions, a CMOS device or other device is used to control electrode assemblies 640. Such a CMOS device may be integrated directly into the flow cell 600, may be integrated into a cartridge (e.g., cartridge 200) in which the flow cell 600 is incorporated, or may be integrated directly into the base instrument 102. As shown in FIG. 7, each electrode assembly 640 extends along the full width of floor 634, terminating at the sidewall 632 of the corresponding well 630. In other versions, each electrode assembly 640 may extend along only a portion of the floor 634. For instance, some versions of electrode assembly 640 may terminate interiorly relative to the sidewall 632. While each electrode assembly 540 is schematically depicted as a single element in FIG. 5, it should be understood that each electrode assembly 540 may in fact be formed by a plurality of discrete electrodes rather than just consisting of one single electrode.

As shown in FIG. 7, specific polynucleotide strands 650 may be created in individual wells 630 by activating the electrode assembly 640 of the relevant wells 630 to electrochemically generate acid that may deprotect the end group of the polynucleotide strand 650 in the well 630. By way of example only, polynucleotide strands 650 may be chemically attached to the surface at the bottom of the well 630 using linkers having chemistries such as silane chemistry on one end and DNA synthesis compatible chemistry (e.g., a short oligo for enzyme to bind to) on the other end.

To facilitate reagent exchange (e.g., transmission of a deblocking agent), each electrode assembly 640 and the floor 634 of each well 630 may include at least one opening 660 in this example. The openings 660 may be fluidly coupled with a flow channel 662 that extends underneath the wells 630, below the floors 634. To provide such an opening 660 through the electrode assembly 640, the electrode assembly 640 may be annular in shape, may be placed in quadrants, may be placed on the perimeter or sidewall 632 of the well 630, or may be placed or shaped in other suitable manners to avoid interference with reagent exchange and/or passage of light (e.g., as may be used in a sequencing process that involved detection of fluorescent emissions). In other implementations, reagents may be provided into the flow channel of the flow cell 600 without the openings 660. It should be understood that the openings 660 may be optional and may be omitted in some versions. Similarly, the flow channel 662 may be optional and may be omitted in some versions.

Figure 9:
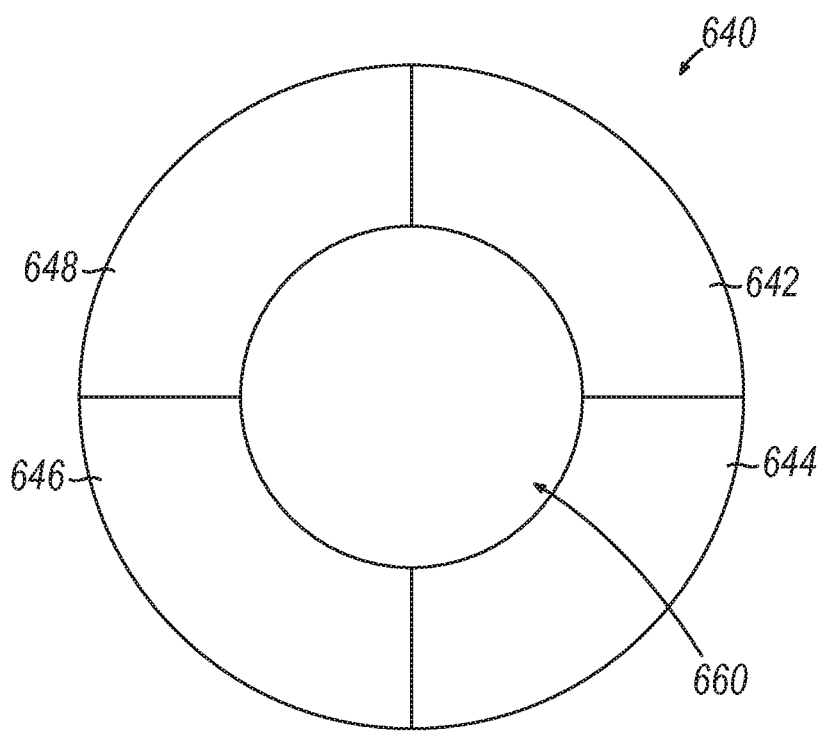
FIG. 9 depicts a top plan view of an example of an electrode assembly.

FIG. 9 shows an example of a form that electrode assembly 640 may take. In this example, electrode assembly 640 includes four discrete electrode segments 642, 644, 646, 648 that together define an annular shape. The electrode segments 642, 644, 646, 648 are thus configured as discrete yet adjacent quadrants of a ring. Each electrode segment 642, 644, 646, 648 may be configured to provide a predetermined charge that is uniquely associated with a particular nucleotide. For instance, electrode segment 642 may be configured to provide a charge that is uniquely associated with adenine; electrode segment 644 may be configured to provide a charge that is uniquely associated with cytosine; electrode segment 646 may be configured to provide a charge that is uniquely associated with guanine; and electrode segment 648 may be configured to provide a charge that is uniquely associated with thymine. When a mixture of those four nucleotides are flowed through the flow channel above the wells 630, activation of electrode segments 642, 644, 646, 648 may cause the corresponding nucleotides from that flow to adhere to the strand 650. Thus, when electrode segment 642 is activated, it may effect writing of adenine to the strand 650; when electrode segment 644 is activated, it may effect writing of cytosine to the strand 650; When electrode segment 646 is activated, it may effect writing of guanine to the strand 650; and when electrode segment 648 is activated, it may effect writing of thymine to the strand 650. This writing may be provided by the activated electrode segment 642, 644, 646, 648 hybridizing the inhibitor of the enzyme for the pixel associated with the activated electrode segment 642, 644, 646, 648. While electrode segments 642, 644, 646, 648 are shown as forming an annular shape in FIG. 9, it should be understood that any other suitable shape or shapes may be formed by electrode segments 642, 644, 646, 648. In still other implementations, a single electrode may be utilized for the electrode assembly 640 and the charge may be modulated to incorporate various nucleotides to be written to the DNA strand or other polynucleotide.

As another example, the electrode assembly 640 may be activated to provide a localized (e.g., localized within the well 630 in which the electrode assembly 640 is disposed), electrochemically generated change in pH; and/or electrochemically generate a moiety (e.g., a reducing or oxidizing reagent) locally to remove a block from a nucleotide. As yet another variation, different nucleotides may have different blocks; and those blocks may be photocleaved based on a wavelength of light communicated to the well 630 (e.g., light 562 projected from the light source 560). As still another variation, different nucleotides may have different blocks; and those blocks may be cleaved based on certain other conditions. For instance, one of the four blocks may be removed based on a combination of a reducing condition plus either high local pH or low local pH; another of the four blocks may be removed based on a combination of an oxidative condition plus either high local pH or low local pH; another of the four blocks may be removed based on a combination of light and a high local pH; and another of the four blocks may be removed based on a combination of light and a low local pH. Thus, four nucleotides may be incorporated at the same time, but with selective unblocking occurring in response to four different sets of conditions.

The electrode assembly 640 further defines the opening 660 at the center of the arrangement of the electrode segments 642, 644, 646, 648. As noted above, this opening 660 may provide a path for fluid communication between the flow channel 662 and the wells 630, thereby allowing reagents, etc. that are flowed through the flow channel 662 to reach the wells 630. As also noted above, some variations may omit the flow channel 662 and provide communication of reagents, etc. to the wells 630 in some other fashion (e.g., through passive diffusion, etc.), Regardless of whether fluid is communicated through the opening 660, the opening 660 may provide a path for optical transmission through the bottom of the well 630 during a read cycle, as described herein. In some versions, the opening 660 may be optional and may thus be omitted. In versions where the opening 660 is omitted, fluids may be communicated to the wells 630 via one or more flow channels that are above the wells 630 or otherwise positioned in relation to the wells 630. Moreover, the opening 660 may not be needed for providing a path for optical transmission through the bottom of the well 630 during a read cycle. For instance, as described below in relation to the flow cell 601, the electrode assembly 640 may comprise an optically transparent material (e.g., optically transparent conducting film (TCF), etc.), and the flow cell 600 itself may comprise an optically transparent material (e.g., glass), such that the electrode assembly 640 and the material forming the flow cell 600 may allow the fluorescence emitted from the one or more fluorophores associated with the machine-written polynucleotide strands 650 to reach an image sensor 540 that is under the well 630.

Figure 8:
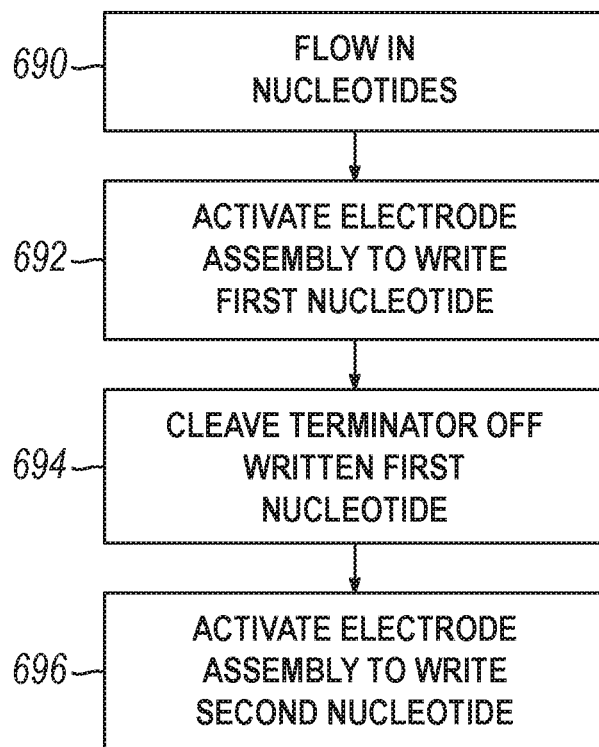
FIG. 8 depicts a flow chart of an example of a process for writing polynucleotides.

FIG. 8 shows an example of a process that may be utilized in the flow cell 600 to machine-write polynucleotides or other nucleotide sequences. At the beginning of the process, as shown in the first block 690 of FIG. 8, nucleotides may be flowed into the flow cell 600, over the wells 630. As shown in the next block 692 in FIG. 8, the electrode assembly 640 may then be activated to write a first nucleotide to a primer at the bottom of a targeted well 630. As shown in the next block 694 of FIG. 8, a terminator may then be cleaved off the first nucleotide that was just written in the targeted well 630. Various suitable ways in which a terminator may be cleaved off the first nucleotide will be apparent to those skilled in the art in view of the teachings herein. Once the terminator is cleaved off the first nucleotide, as shown in the next block 696 of FIG. 8, the electrode assembly 640 may be activated to write a second nucleotide to the first nucleotide. While not shown in FIG. 8, a terminator may be cleaved off the second nucleotide, then a third nucleotide may be written to the second nucleotide, and so on until the desired sequence of nucleotides has been written.

In some implementations, encoding of data via synthesis of biological materials such as DNA may be performed in other manners. For example, in some implementations, the flow cell 600 may lack the electrode assembly 640 altogether. For instance, deblock reagents may be selectively communicated from the flow channel 662 to the wells 630 through the openings 660. This may eliminate the need for electrode assemblies 640 to selectively activate nucleotides. As another example, an array of wells 630 may be exposed to a solution containing all nucleotide bases that may be used in encoding the data, and then individual nucleotides may be selectively activated for individual wells 630 by using light from a spatial light modulator (SLIM). As another example, in some implementations individual bases may be assigned combined values (e.g., adenine may be used to encode the binary couplet 00, guanine may be used to encode the binary couplet 01, cytosine may be used to encode the binary couplet 10, and thymine may be used to encode the binary couplet 11) to increase the storage density of the polynucleotides being created. Other examples are also possible and will be immediately apparent to those skilled in the art in light of this disclosure. Accordingly, the above description of synthesizing biological materials such as DNA to encode data should be understood as being illustrative only: and should not be treated as limiting.

VI. Reading Machine-Written Biological Material

After polynucleotide strands 650 have been machine-written in one or more wells 630 of a flow cell 600, the polynucleotide strands 650 may be subsequently read to extract whatever data or other information was stored in the machine-written polynucleotide strands 650. Such a reading process may be carried out using an arrangement such as that shown in FIG. 5 and described above. In other words, one or more light sources 560 may be used to illuminate one or more fluorophores associated with the machine-written polynucleotide strands 650; and one or more image sensors 540 may be used to detect the fluorescent light emitted by the illuminated one or more fluorophores associated with the machine-written polynucleotide strands 650. The fluorescence profile of the light emitted by the illuminated one or more fluorophores associated with the machine-written polynucleotide strands 650 may be processed to determine the sequence of bases in the machine-written polynucleotide strands 650. This determined sequence of bases in the machine-written polynucleotide strands 650 may be processed to determine the data or other information that was stored in the machine-written polynucleotide strands 650.

In some versions, the machine-written polynucleotide strands 650 remain in the flow cell 600 containing wells 630 for a storage period. When it is desired to read the machine-written polynucleotide strands 650, the flow cell 600 may permit the machine-written polynucleotide strands 650 to be read directly from the flow cell. By way of example only, the flow cell 600 containing wells 630 may be received in a cartridge (e.g., cartridge 200) or base instrument 102 containing light sources 560 and/or image sensors 540, such that the machine-written polynucleotide strands 650 are read directly from the wells 630.

Figure 10:
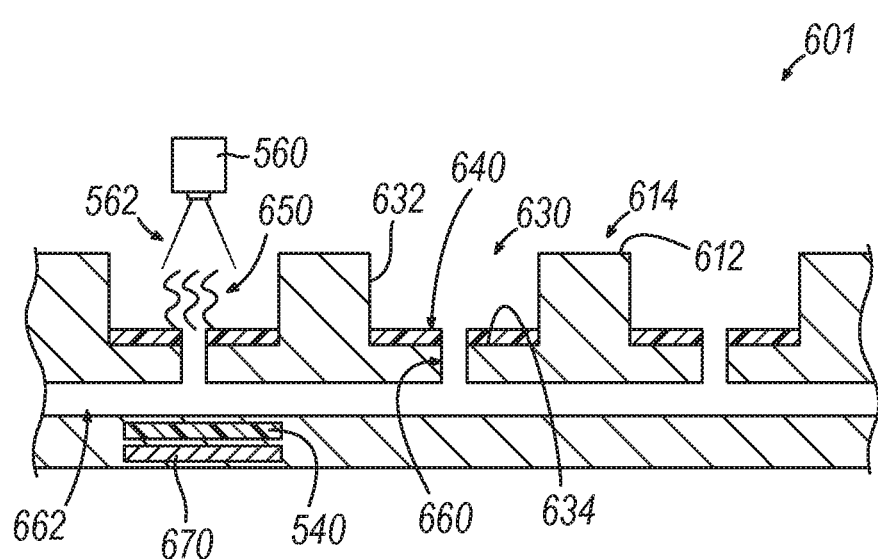
FIG. 10 depicts a block schematic cross-sectional view of another example of wells that may be incorporated into the channel of FIG. 4.

As another illustrative example, the flow cell containing wells 630 may directly incorporate one or both of light source(s) 560 or image sensor(s) 540. FIG. 10 shows an example of a flow cell 601 that includes wells 630 with electrode assemblies 640, one or more image sensors 540, and a control circuit 670. Like in the flow cell 500 depicted in FIG. 5, the flow cell 601 of this example is operable to receive light 562 projected from a light source 560. This projected light 562 may cause one or more fluorophores associated with the machine-written polynucleotide strands 650 to fluoresce; and the corresponding image sensor(s) 540 may capture the fluorescence emitted from the one or more fluorophores associated with the machine-written polynucleotide strands 650.

As noted above in the context of the flow cell 500, each well 650 of the flow cell 601 may include its own image sensor 540 and/or its own light source 560; or these components may be otherwise configured and arranged as described above. In the present example, the fluorescence emitted from the one or more fluorophores associated with the machine-written polynucleotide strands 650 may reach the image sensor 540 via the opening 660. In addition, or in the alternative, the electrode assembly 640 may comprise an optically transparent material (e.g., optically transparent conducting film (TCF), etc.), and the flow cell 601 itself may comprise an optically transparent material (e.g., glass), such that the electrode assembly 640 and the material forming the flow cell 601 may allow the fluorescence emitted from the one or more fluorophores associated with machine-written polynucleotide strands 650 to reach the image sensor 540. Moreover, various kinds of optical elements (e.g., lenses, optical waveguides, etc.) may be interposed between the wells 650 and the corresponding image sensor(s) to ensure that the image sensor 540 is only receiving fluorescence emitted from the one or more fluorophores associated with the machine-written polynucleotide strands 650 of the desired well(s) 630.

In the present example, the control circuit 670 is integrated directly into the flow cell 601. By way of example only, the control circuit 670 may comprise a CMOS chip and/or other printed circuit configurations/components. The control circuit 670 may be in communication with the image sensor(s) 540, the electrode assembly(ies) 640, and/or the light source 560. In this context, "in communication" means that the control circuit 670 is in electrical communication with image sensor(s) 540, the electrode assembly(ies) 640, and/or the light source 560. For instance, the control circuit 670 may be operable to receive and process signals from the image sensor(s) 540, with the signals representing images that are picked up by the image sensor(s) 540. "In communication" in this context may also include the control circuit 670 providing electrical power to the image sensor(s) 540, the electrode assembly(ies) 640, and/or the light source 560.

In some versions, each image sensor 540 has a corresponding control circuit 670. In some other versions, a control circuit 670 is coupled with several, if not all, of the image sensors in the flow cell 601. Various suitable components and configurations that may be used to achieve this will be apparent to those skilled in the art in view of the teachings herein. It should also be understood that the control circuit 670 may be integrated, in whole or in part, in a cartridge e.g., removable cartridge 200) and/or in the base instrument 102, in addition to or in lieu of being integrated into the flow cell 601.

As still another illustrative example, regardless of whether a write-only flow cell like the flow cell 600 of FIG. 7 or a read-write flow cell like the flow cell 601 of FIG. 10 is used, the machine-written polynucleotide strands 650 may be transferred from wells 630 after being synthesized. This may occur shortly after the synthesis is complete, right before the machine-written polynucleotide strands 650 are to be read, or at any other suitable time. In such versions, the machine-written polynucleotide strands 650 may be transferred to a read-only flow cell like the flow cell 500 depicted in FIG. 5; and then be read in that read-only flow cell 500. Alternatively, any other suitable devices or processes may be used.

In some implementations, reading data encoded through the synthesis of biological materials may be achieved by determining the well(s) 630 storing the synthesized strand(s) 650 of interest and then sequencing those strands 650 using techniques such as those described previously (e.g., sequencing-by-synthesis). In some implementations, to facilitate reading data stored in nucleotide sequences, when data is stored, an index may be updated with information showing the well(s) 630 where the strand(s) 650 encoding that data was/were synthesized. For example, when an implementation of a system 100 configured to synthesize strands 650 capable of storing up to 256 bits of data is used to store a one megabit (1,048,576 bit) file, the system controller 120 may perform steps such as: 1) break the file into 4,096 256 bit segments; 2) identify a sequence of 4,096 wells 630 in the flow cell 600, 601 that were not currently being used to store data; 3) write the 4,096 segments to the 4,096 wells 430, 530; 4) update an index to indicate that the sequence starting with the first identified well 630 and ending at the last identified well 630 was being used to store the file. Subsequently, when a request to read the file was made, the index may be used to identify the well(s) 630 containing the relevant strand(s) 650, the strand(s) 650 from those wells 630 may be sequenced, and the sequences may be combined and converted into the appropriate encoding format (e.g., binary), and that combined and converted data may then be returned as a response to the read request.

In some implementations, reading of data previously encoded via synthesis of biological materials may be performed in other manners. For example, in some implementations, if a file corresponding to 4,096 wells 630 was to be written, rather than identifying 4,096 sequential wells 630 to write it to, a controller may identify 4,096 wells 630 and then update the index with multiple locations corresponding to the file in the event that those wells 630 did not form a continuous sequence. As another example, in some implementations, rather than identifying individual wells 630, a system controller 120 may group wells 630 together (e.g., into groups of 128 wells 630), thereby reducing the overhead associated with storing location data (i.e., by reducing the addressing requirements from one address per well 630 to one address per group of wells 630). As another example, in implementations that store data reflecting the location of wells 630 where DNA strands or other polynucleotides have been synthesized, that data may be stored in various ways, such as sequence identifiers (e.g., well 1, well 2, well 3, etc.) or coordinates (e.g., X and Y coordinates of a well's location in an array).

As another example, in some implementations, rather than reading strands 650 from the wells 630 in which they were synthesized, strands 650 may be read from other locations. For instance, strands 650 may be synthesized to include addresses, and then cleaved from the wells 630 and stored in a tube for later retrieval, during which the included address information may be used to identify the strands 650 corresponding to particular files. As another illustrative example, the strands 650 may be copied off the surface using polymerase and then eluted & stored in tube. Alternatively, the strands 650 may be copied on to a bead using biotinylated oligos hybridized to DNA strands or other polynucleotides and capturing extended products on streptavidin beads that are dispensed in the wells 630. Other examples are also possible and will be immediately apparent to those of skill in the art in light of this disclosure. Accordingly, the above description of retrieving data encoded through the synthesis of biological materials should be understood as being illustrative only; and should not be treated as limiting.

Implementations described herein may utilize a polymer coating for a surface of a flow cell, such as that described in U.S. Pat. No. 9,012,022, entitled "Polymer Coatings," issued Apr. 21, 2015, which is incorporated by reference herein in its entirety. Implementations described herein may utilize one or more labelled nucleotides having a detectable label and a cleavable linker, such as those described in U.S. Pat. No. 7,414,116, entitled "Labelled Nucleotide Strands," issued Aug. 19, 2008, which is incorporated by reference herein in its entirety. For instance, implementations described herein may utilize a cleavable linker that is cleavable with by contact with water-soluble phosphines or water-soluble transition metal-containing catalysts having a fluorophore as a detectable label. Implementations described herein may detect nucleotides of a polynucleotide using a two-channel detection method, such as that described in U.S. Pat. No. 9,453,258, entitled "Methods and Compositions for Nucleic Acid Sequencing," issued Sep. 27, 2016, which is incorporated by reference herein in its entirety. For instance, implementations described herein may utilize a fluorescent-based SBS method having a first nucleotide type detected in a first channel (e.g., dATP having a label that is detected in the first channel when excited by a first excitation wavelength), a second nucleotide type detected in a second channel (e.g., dCTP having a label that is detected in a second channel when excited by a second excitation wavelength), a third nucleotide type detected in both the first and second channel (e.g., dTTP having at least one label that is detected in both channels when excited by the first and/or second excitation wavelength), and a fourth nucleotide type that lacks a label that is not, or that is minimally, detected in either channel (e.g., dGTP having no label). Implementations of the cartridges and/or flow cells described herein may be constructed in accordance with one or more teachings described in U.S. Pat. No. 8,906,320, entitled "Biosensors for Biological or Chemical Analysis and Systems and Methods for Same," issued Dec. 9, 2014, which is incorporated by reference herein in its entirety; U.S. Pat. No. 9,512,422, entitled "Gel Patterned Surfaces," issued Dec. 6, 2016, which is incorporated by reference herein in its entirety; U.S. Pat. No. 10,254,225, entitled "Biosensors for Biological or Chemical Analysis and Methods of Manufacturing the Same," issued Apr. 9, 2019, which is incorporated by reference herein in its entirety; and/or U.S. Pub. No. 2018/0117587, entitled "Cartridge Assembly," published May 3, 2018, which is incorporated by reference herein in its entirety.

VII. Systems and Methods for Polynucleotide Hard Drive Device

As the cost, speed, and availability of devices and materials used during the writing (e.g., synthesis) and reading (e.g., sequencing) of data to and from polynucleotide storage devices improves, a point may be reached in various settings where DNA based storage is a viable, if not preferable, addition or alternative to storage based on conventional methods (e.g., magnetic, electronic). For example, in datacenter scale, long term archival scenarios, DNA based storage may offer a number of advantages such as stability, data density, and durability. These advantages may offset the relative cost and complexity of systems and instrumentation needed for DNA based storage, as several such DNA storage systems may service a single datacenter.

For such scenarios, providing a cartridge or module that may be coupled or mounted with a DNA storage system for writing and reading, and then dismounted from the DNA storage system and relocated to a long-term archival area for storage, may provide a number of advantages. For example, providing a purpose-built module allows for additional features to be included in the module to improve both the reading and writing process, as well as to improve the long-term stability of machine-written DNA that stores data within the module. As another example, providing a single module that, from the perspective of users, appears to be a durable, closed system, similar in appearance and function to many conventional portable storage drives and devices, may improve the acceptability and usability of the DNA storage device for users. As an example, some users may otherwise mistakenly assume that the machine-written DNA is fragile or unreliable as compared to conventional storage methods, especially where the DNA storage device appears overly complex or flow cell surfaces and storage wells are outwardly visible.

A real-world example of the above advantages may be seen in the case of magnetic platter storage drives, which contain a magnetic platter that rotates at speeds of seven thousand RPM or more, while a reading/writing head floats above the platter at a "flying height" of just a few nanometers. With such devices, an obstruction on the platter as thin as a fingerprint or even a particle of smoke may result in a catastrophic collision with the read head and a complete or partial loss of stored data. However, since such complexities are protected within specially developed enclosures and not generally visible to users, magnetic platter hard drives are still a popular option for storage and are perceived as providing robust, dependable storage, despite their complexities.

A. Example DNA Storage System

When described herein, a system operable to read digital data encoded as a polynucleotide, such as DNA, encode and write digital data to DNA, or both may be referred to as a system for DNA storage, or a "DNA storage system." It should be understood that such a system may include various components and devices that may be assembled into a single piece of equipment (e.g., may be assembled and communicatively coupled within a case) or may be separate pieces of equipment that may be connected, arranged, or both in order to provide the described features.

Figure 11:
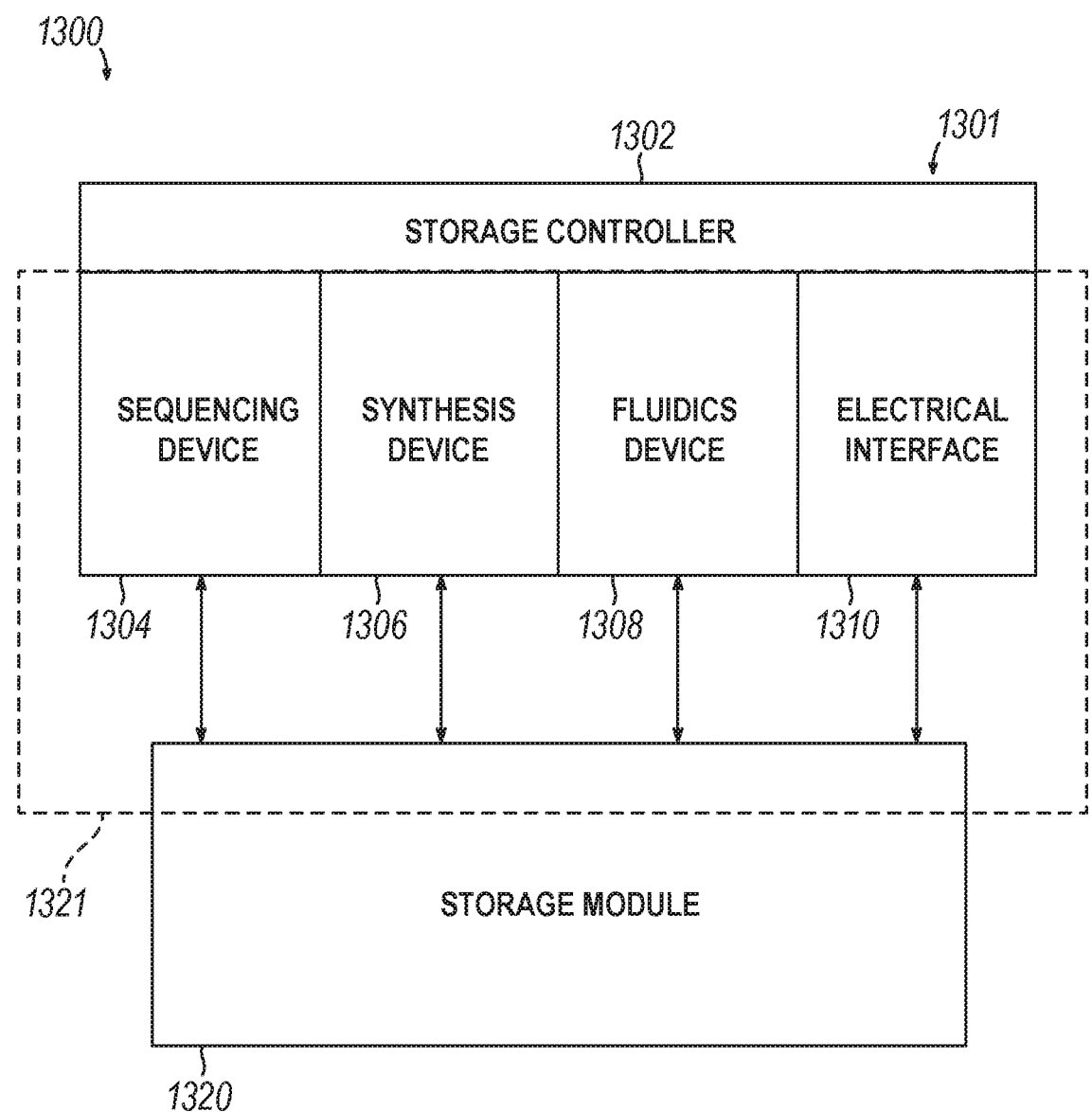
FIG. 11 depicts a schematic diagram of an example of a polynucleotide storage system.

As an example, FIG. 11 shows a schematic diagram of an example of a DNA storage system 1300. The DNA storage system 1300 includes a set of instrumentation 1301 and a storage device or module 1320, which may be integrated with the DNA storage system 1300 or, in some implementations, removably coupled with the DNA storage system 1300 via a module interface such as a module receiver 1321. The set of instrumentation 1301 may correspond to the base instrument 102 described above. The set of instrumentation 1301 may be assembled within a single piece of equipment or may be one or more separate pieces of equipment arranged, connected, or both in order to provide the described functionality. The set of instrumentation 1301 includes a storage controller 1302 that may include one or more processors and memories configured to store and execute instructions to operate the set of instrumentation 1301. The set of instrumentation 1301 also includes a sequencing device 1304, a synthesis device 1306, a fluidics device 1308, and an electrical interface 1310.

In some implementations, the storage controller 1302, the sequencing device 1304, the synthesis device 1306, the fluidics device 1308, and the electrical interface 1310 may be separate devices with one or more fluidic, electric, or mechanical interfaces therebetween. In other implementations, the storage controller 1302, the sequencing device 1304, the synthesis device 1306, the fluidics device 1308, and the electrical interface 1310 may be integrated into a single device with each of the sequencing device 1304, the synthesis device 1306, the fluidics device 1308, and the electrical interface 1310 forming a sub-component thereof.

The sequencing device 1304 is operable to read data encoded and stored as a polynucleotide, such as DNA, in one or more wells of the storage device 1320, and may include features such as imaging devices, optical sensors, lighting devices (e.g., LEDs, other illuminators), and other devices that are usable to detect characteristics of DNA stored within a well (e.g., such as the process and devices described above in relation to SBS, where fluorescent labels or tags associated with individual nucleotides are detectable by an optical sensor).

The synthesis device 1306 is operable to synthesize polynucleotides having a particular arrangement of nucleotides within one or more wells of the storage device 1320. The synthesis device 1306 includes or is coupled with a store of individual nucleotides or other biological material and an input delivery device operable to communicate input biological material to one or more wells. In some implementations this may include a set of electrodes positioned proximately to the wells and operable to attract a particular nucleotide to a particular well, while the input delivery device provides a nucleotide carrier fluid, or a nucleotide writing reagent, to the flow channel 410 via the inlet port 420. In some implementations, this may include a nucleotide injection head that may be positioned proximately to a desired well so that one or more nucleotides may be released in a desired order.

The fluidics device 1308 may include any of the devices or features described herein in relation to fluidics, such as a fluidics network, pumps, valves, and other components operable to provide a desired fluid type, at a desired volume and pressure, and to one or more of the flow channels 410 or particular locations on the one or more flow channels 410. In some implementations, the fluidics device 1308 may include electro-wetting features operable to precisely direct desired volumes of fluid to desired locations, rather than flooding the flow channels 410 with fluid. In some implementations the fluidics device 1308 may be used to provide thermal control or conditioning for one or more components of the DNA storage system 1300. As an example, where fluid being transferred by the fluidics device 1308 needs to be heated prior to use with the storage device 1320, the fluid may be routed through portions of the storage controller 1302 (e.g., proximate to processors, memories, and heat-sinks) in order to draw heat from those components into the fluid. Where the fluid being transferred needs to be cooled prior to use, the fluid may be routed through a cooling system of the DNA storage device 1300. Other similar features that may be included in the DNA storage system 1300 include thermal control devices that may be positioned to heat or cool fluid, or heat or cool the storage device 1320 itself, and may include air blown temperature control devices, solid-state thermoelectric plates, and other devices.

Fluids provided with the fluidics device 1308 may include fluid reagents that are created and used in various processes performed with the sequencing device 1304 and the synthesis device 1306, and may also include non-functional fluids such as distilled water used to flush and clean one or more components of the DNA storage system 1300. Reagents used by the sequencing device 1304 may vary from those used by the synthesis device 1306, and each device may itself use one or more different reagents during different parts of synthesis and sequencing. When used herein, any of the varying reagents that may be supplied during sequencing operations may be referred to collectively as nucleotide reading reagents, while any of the varying reagents that may be supplied during synthesis operations may be referred to collectively as nucleotide writing reagents.

In some implementations, such as where the storage device 1320 includes features requiring power or data transfer, the electrical interface 1310 may include wired, conductive connections, may include wireless transceiver devices (e.g., RFID, NFC, Bluetooth, optical transmitters, inductive charging devices) that are capable of exchanging power, data, or both with the storage device 1320, where the storage device 1320 includes features requiring power or data transfer.

Where the storage device 1320 is removable, the DNA storage system 1300 may also include one or more features to couple and statically position the storage device 1320 relative to the set of instrumentation 1301 during use. Such features may include the module receiver 1321, which may be a slot in which the storage device 1320 may be seated, as well as guiding features (e.g., rails) and locking features to position the storage device 1320 with a high degree of precision and immobilization so that one or more of the set of instrumentation 1301 are repeatably and automatically positioned to interact with their corresponding interfaces. In other implementations, the storage device 1320 may comprise a flow cell 1322 that interfaces with the components of the set of instrumentation 1301.

It should be understood that the DNA storage system 1300 is only an example, and that many variations are possible and will be apparent to those skilled in the art in light of this disclosure. As an example, the set of instrumentation 1301 and the storage device 1320 may have fewer components or more components than shown. As another example, some implementations of the storage device 1320 may include components of the set of instrumentation 1301, such as where a plurality of electrodes of the sequencing device 1304 are integrated on or within an internal flow cell of the storage device 1320 itself. In such cases, the portion of the sequencing device 1304 paired with the set of instrumentation 1301 may include conductive switching networks that allow electrical signals to be produced and transmitted to a desired electrode mounted within or on the flow cell, as will be described in more detail below.

B. Example DNA Hard Drive Device

Figure 12A:
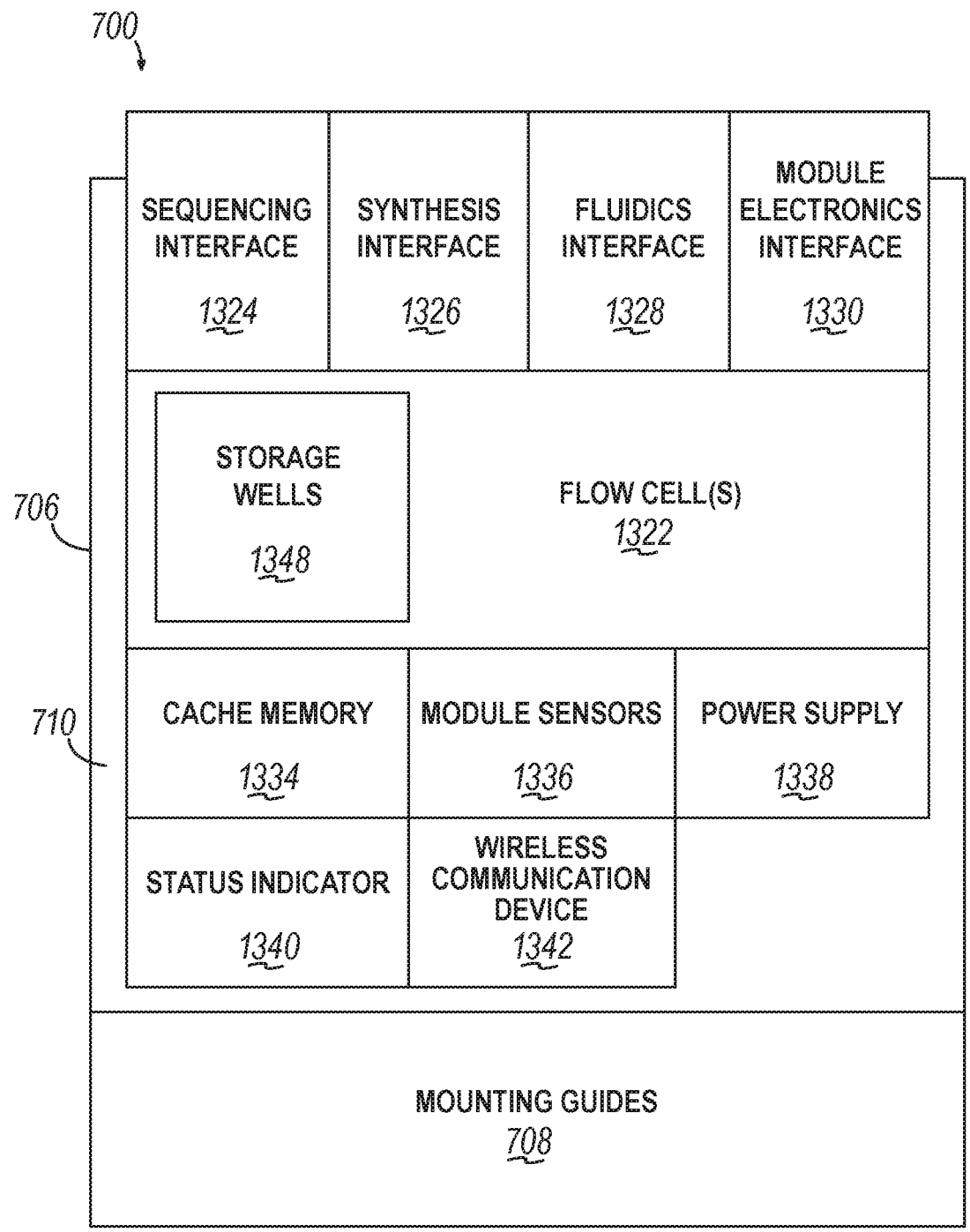
FIG. 12A depicts a schematic diagram illustrating an example of a storage device usable with the polynucleotide storage system of FIG. 11.
Figure 12B:
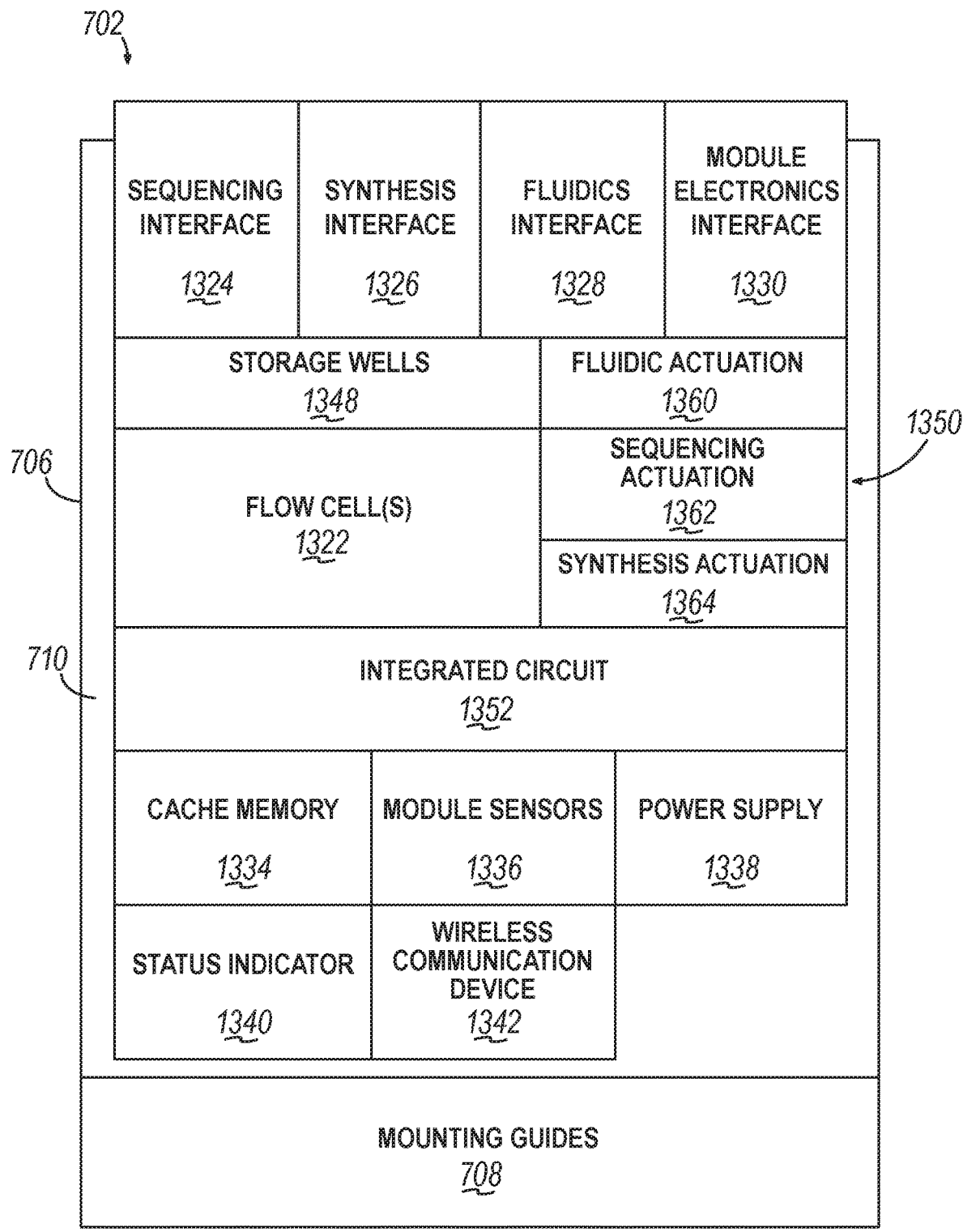
FIG. 12B depicts a schematic diagram illustrating an alternative example of a storage device usable with the polynucleotide storage system of FIG. 11.

FIGS. 12A-12B each show examples of a DNA storage device or module 700, 702, such as the storage device 1320, that may be used as a DNA hard drive module with a DNA storage system such as the DNA storage system 1300. FIG. 12A shows a DNA storage device 700 that includes a case 706, on which one or more mounting guides 708 are positioned and adapted to aid in coupling the storage device 700 with the DNA storage system 1300 to precisely position and immobilize the storage device 700 with respect to the set of instrument 1301. The mounting guides 708 may include one or more of rails to aid in sliding a controlled direction and distance, active lock-key mechanisms that displace or are displaced by a corresponding portion of a receiver portion (e.g., the module receiver 1321) during coupling to allow a complete coupling only when inserted with the correct orientation, passive lock-key mechanisms that fit against or receive a static portion of the DNA storage system 1300 during coupling to ensure proper orientation, and latching or locking mechanisms to immobilize the storage device 700 when proper orientation and positioning is achieved with respect to the DNA storage system 1300.

The case 706 may include an interior 710 that may be sealed or shielded against ambient environments when the storage device 700 is not coupled with the DNA storage system 1300 or may be sealed against ambient environments at all times. In some implementations, the case 706 may be sealed to prevent easy access or visibility of components in the interior 710, but not sealed against air, humidity, or other aspects of the ambient environment. In some implementations, the case 706 may include doors or covers that slide, rotate, or otherwise move when the storage device 700 is coupled with the DNA storage system 1300 to allow a complete coupling. In some implementations, devices or components within the interior 710 may be themselves individually sealed against the environment of the interior 710 and the ambient environments external to the case 706, whether or not the case 706 itself is sealed in any way. Sealing and shielding features may include, for example, air-tight seals and couplings of components, insulation materials to reduce the effect of ambient temperatures on the interior 710, shock absorptive materials to reduce the impact of motion, vibration, or other physical impacts on components within the interior 710, radiation shielding materials to prevent external sources of radiation from affecting the interior 710, and other features.

The storage device 700 includes one or more flow cells 1322, which themselves include a plurality of storage wells 1348. The flow cells 1322 and their corresponding storage wells 1348 may include one or more of the features described in relation to the flow cell 400 described in FIG. 3, the flow cell 500 described in FIG. 5, the flow cell 600 described in FIG. 6, the flow cell 601 described in FIG. 8, or other flow cells described herein.

The storage device 700 includes a number of interfaces that may be partially within the interior 710 and partially exposed by the case 706 (e.g., visible upon the face of the case or exposed when a cover, door, or other device is displaced during coupling). The shown interfaces include a sequencing interface 1324, a synthesis interface 1326, a fluidics interface 1328, and a module electronics interface 1330.

In some implementations, the flow cell 1322, the sequencing interface 1324, the synthesis interface 1326, the fluidics interface 1328, and the set of module electronics 1330 may be separate devices with one or more fluidic, electric, or mechanical interfaces therebetween. In other implementations, the flow cell 1322, the sequencing interface 1324, the synthesis interface 1326, the fluidics interface 1328, and the set of module electronics 1330 may be integrated into a single device with each of the flow cell 1322, the sequencing interface 1324, the synthesis interface 1326, the fluidics interface 1328, and the set of module electronics 1330 forming a sub-component thereof.

When coupled with the DNA storage system 1300, the sequencing device 1304 interacts with the flow cell 1322 via the sequencing interface 1324. The sequencing interface 1324 may include a glass cover, a glass substrate, or other interface surface configured to allow the sequencing device 1304 to interact with the flow cells 1322 and the storage wells 1348. In an example where the sequencing device 1304 includes an optical sensor and light source usable to detect tagged or labelled nucleotides or other substances within a well, the sequencing interface 1324 may include a transparent glass cover that covers the flow cells 1322 (e.g., such as described in the context of the flow channels 410) and prevents leakage of fluids transported within, while also transmitting light in each direction to and from the storage wells 1348. In some implementations, the sequencing interface 1324 may include one or more waveguides to selectively illuminate one or more portions of the flow cell 1322.

The synthesis interface 1326 is configured to allow the synthesis device 1306 to interact with one or more wells of the flow cell 1322, and so will vary depending upon the particular synthesis device 1306. In other implementations, the synthesis device 1306 may synthesize DNA nucleotides on a particular surface of the flow cell 1322 without wells. In some implementations, the synthesis interface may include a conductive layer or coupling that receives electrical characteristics from an electrode and conducts them to an area proximate to a well of the flow cell 1322. In some implementations, the synthesis interface 1326 may include or may interact with some or all of the fluidics interface 1328, such as where the synthesis device 1306 provides a nucleotide carrier fluid during synthesis. In some implementations, the synthesis interface 1326 may include a porous membrane that seals the flow cell 1322, while allowing nucleotides to pass into the flow cell 1322 or into a particular storage well 1348 when injected by a nucleotide injection head or port at a desired location. In some implementations, the synthesis interface 1326 may be formed from a flexible material, may include a plurality of small valves, or may include other features that are configured to self-seal after a nucleotide injection head or port provides nucleotides.

The fluidics interface 1328 will vary based on a particular implementation of the fluidics device 1308 and may include one or more features of the fluidics networks described herein, such as the inlet ports 420, the outlet ports 422, and other components. The fluidics interface 1328 may be passive, such as a manifold network that provides an equal flow of supplied fluid to one or more of the storage wells 1348 or a set of inlets that may provide fluid to a particular set of the storage wells 1348 (e.g., such as the wells of a single channel of the flow channels 410). In some implementations, the fluidics interface 1328 may also include or operate with one or more active features, such as the fluidic actuation 1360, which may include valves, diverters, pumps, or other features to provide more control over the application of fluid to the flow cell 1322 surface. Valves may be electronically controlled or may be activated as a result of a certain pressure of input fluid from the fluidics device 1308. Pumps or electro-wetting surfaces may be electronically controlled using power and control signals provided by the electrical interface 1310 and may be used to provide fluid to a particular set of storage wells 1348, rather than providing fluid to the entire flow cell 1322.

The storage device 700 may also include one or more components that are operated by electrical power or control signals from an external source or that require the exchange of data with an external source. Such components may be coupled with a module electronics interface 1330 of the storage device 700, which itself couples with the electrical interface 1310 of the DNA storage system 1300 when the storage device 700 is coupled with the DNA storage system 1300. Components of the storage device 700 may, through the module electronics interface 1330, receive power from the DNA storage system 1300, exchange data with the storage controller 1302, or exchange data with other devices that are communicatively coupled with the storage controller 1302.

The storage device 700 may also include a cache memory 1334. The cache memory may include a non-volatile, electronic memory that may receive and store data from other devices, such as the storage controller 1302, another device that is communicatively coupled with the storage controller 1302, or another device of the storage device 700 itself. The cache memory 1334 may receive and store indexing data that describes the status and contents of the storage wells 1348, the locations of particular files or data stored in the storage wells 1348, encoding or decryption information usable with corresponding information on the DNA storage system 1300 to read data from the storage wells 1348. Such information may be provided and modified by the storage controller 1302 during read and write operations involving the storage device 700. The cache memory 1334 may also be used to store portions of data that is written to the storage wells 1348, as will be described in more detail below, in order to allow for simultaneous reading and writing of data to the storage device 700 in some scenarios.

The storage device 700 may also include a set of module sensors 1336. The module sensors may include, for example, temperature or humidity sensors at various locations (e.g., on a wall of the interior 710, on a surface of the flow cell 1322), vibration or shock sensors, radiation sensors, light sensors, and other environmental sensors. The set of module sensors 1336 may generate signals and data based upon sensed conditions, that may be stored on the cache memory 1334, provided to the storage controller 1302 when coupled with the DNA storage system 1300; or provided to another device or component of the DNA storage system 1300 or the storage device 700.

The storage device 700 may also include a power supply 1338, such as a battery, solar cell, inductive charging receiver, directed energy receiver, or other device that may produce or receive power instead of or in addition to the module electronics interface 1330. In some implementations, the power supply 1338 may power some or all of the components of the storage device 700, even when not coupled to the DNA storage system 1300. As an example, a battery of the power supply 1338 may be charged via the module electronics interface 1330 in order to power the module sensors 1336 when the storage device 700 is dismounted from the DNA storage system 700, such as during long term storage or transit to long term storage. As another example, an inductive charging receiver may power the storage device 700 when in storage, such a where the storage rack or shelf system that the storage device 700 is placed in for archival storage includes an inductive charging surface that aligns with the inductive charging receiver.

The storage device 700 may also include a status indicator 1340, which may include a light indicator, audio indicator, display screen, or other device operable to provide information to a user. The status indicator 1340 may be interacted with by a user to review information provided by the module sensors 1336 or the power supply 1338 or may be activated by such devices to provide warnings relating to the storage device 700. For example, where the module sensors 1336 detect temperature, humidity, motion, radiation, or other characteristics that may damage the machine written DNA stored within the storage device 700, the status indicator 1340 may be activated to illuminate a red flashing light emitting diode (LED), to emit a warning sound from a speaker or to provide another indication of warning.

The storage device 700 may also include a wireless communication device 1342, which may include Wi-Fi transceiver, a Bluetooth or NEC transceiver, an RFID emitter, or another device capable of wireless transmission of data, receipt of data, or both. In some implementations, the wireless communication device 1342 may generate electronic communications to other devices within range of such transmissions based upon data from the module sensors 1336 (e.g., such as a temperature or radiation alert warning provided via a low energy Bluetooth transceiver to a base station near an archival storage rack, which may then generate various types of alarms). In some implementations, an RFID of the wireless communication device 1342 may store a unique identifier for the storage device 700, which may be provided to the DNA storage device 1300 when the storage device 700 is inserted. In some implementations, such an RFID may receive and store information from the module sensors 1336, which may be read by a handheld RFID reader placed near the storage device 700 in order to wirelessly receive temperature data or other sensor-acquired data recently generated by the storage device 700. In some implementations, a transceiver of the wireless communication device 1342 may connect to a locally available network and provide network access to the contents of the cache memory 1334, to aid in remotely determining the locations and contents of particular storage devices or particular files or data stored on flow cells 1322 of storage device.

It should be understood that the storage device 700 may be implemented in various ways and that not all features shown in FIG. 12A are required or will be present in every storage device. As an example, some storage devices that are intended to provide very simple, low cost storage may only include a few simple interfaces (e.g., such as a glass cover that provides optical access to the flow cell 1322), a flow cell, and a case including one or more mounting guides to aid in orienting and inserting the module into the DNA storage system 1300. Even high-end storage devices may not include all of the features of the storage device 700, and so it should be understood that the features shown are examples only, and that varying implementations of storage devices based on the storage device 700 will include varying combinations or omissions of those features.

Further, some storage devices may include additional features not explicitly shown in FIG. 12A. As an example, some implementations of storage devices such as the storage device 700 may include a fluid reservoir that contains one or more reagents used in writing data, reading data, or both, such that the storage device 700 is paired with and carries reagents during transit. In such implementations, the fluidics device 1308 may include a pump or provide pressurized liquid or gas via the fluidics network to move required reagents from such an internal reservoir to the flow cell 1322, instead of or in addition to providing reagent itself.

As an example, FIG. 12B shows an alternate example of a storage device 702, usable with a DNA storage system such as the DNA storage system 1300. The storage device 702 includes many of the features of the storage device 700 of FIG. 12A, having similar functions as described in the context of storage device 700. The storage device 702 of this example also includes a set of flow cell tools 1350, which may include one or more features operable to aid in synthesis, sequencing, and other operations affecting the flow cell 1322. The set of flow cell tools 1350 for the storage device 702 includes fluidic actuation device 1360, sequencing actuation device 1362, and synthesis actuation device 1364. The set of flow cell tools may be operated by an integrated circuit 1352, as will be described in more detail below, or may be operated via control signals received via the module electronics interface 1330, or both.

The fluidic actuation device 1360 may include active fluidics features that are operable to control the delivery of various fluids to the storage wells 1348 or other areas of the flow cell 1322. As an example, the fluidic actuation device 1360 may include an electro-wetting surface configured to receive electrical signals and produce corresponding electrical characteristics in order to transport controlled quantities of fluid to particular locations on the electro-wetting surface. The fluidic actuation device 1360 may also include electrically actuated valving, pumps, nozzles, and other features of an active fluidics network that are operable to provide controlled delivery of fluid to surfaces of the flow cell 1322.

The sequencing actuation device 1362 may include active fluidic features similar to those of the fluidic actuation device 1360, and may be separate components, or may be shared with the fluidic actuation device 1360 in varying implementations. The sequencing actuation device 1362 may also include active optical features that are usable to limit optical crosstalk between nearby storage wells 1348 during illumination and imaging processes that may occur during sequencing, or that are usable to provide illumination, or other features. As an example, the sequencing actuation device 1362 may include electrochromic materials and components operable to alter the light transmission properties of the storage wells 1348 to allow sequencing, or to reduce the possibility of crosstalk to nearby wells. As another example, the sequencing actuation device 1362 may include a plurality of illuminators (e.g., LEDs), with each illuminator corresponding to and operable to illuminate one or more of the storage wells 1348.

The synthesis actuation device 1364 may include active features usable during synthesis, such as active fluidic features that are similar to or shared with those of the fluidic actuation device 1360; and may also include active features operable to promote or suppress synthesis activity. As an example, the synthesis actuation device 1364 may include a plurality of well electrodes that correspond to the storage wells 1348 on a one-to-one, many-to-one, one-to-many, or many-to-many basis. The well electrodes may be individually or collectively operated to produce electrical characteristics proximate to the storage wells 1348 that may promote or suppress certain events related to synthesizing and sequencing (e.g., such as in the case of SBS, where a sequencing process may include one or more sub-processes similar to those performed during synthesis) of machine written DNA within the storage well 1348, as described in relation to FIGS. 6-8 and the electrode assembly 640.

The well electrodes of the synthesis actuation device 1364 may be implemented as the electrode assembly 640, may be mounted on a sidewall of the storage well 1348, may be mounted on a surface of the flow cell 1322 at a perimeter of the storage well 1348, or may be mounted elsewhere. The well electrodes may be mounted on the top side of the flow cell 1322 (e.g., the surface having well openings) or within the storage well 1348, with the electrical circuitry that provides power to each electrode running from that electrode to an underside of the flow cell 1322, opposite the top side.

The well electrodes of the synthesis actuation device 1364 may have a one-to-one or many-to-one correspondence with the storage wells 1348, such that one or more of the well electrodes may be activated to produce desired electrical characteristics at a single storage well 1348. In implementations having a different correspondence, a single well electrode may be activated to produce desired electrical characteristics at several storage wells 1348 (e.g., such that activation of the single well electrode may enable synthesis (block 1224) in a first well and synthesis (block 1228) in a second well, or sequencing of a first well and a second well, where those wells are proximate to each other and spatially associated with the single well electrode).

The storage device 702 also includes an integrated circuit 1352 which may include, for example, a complementary metal-oxide-semiconductor (CMOS). The integrated circuit 1352 may be configured to receive control signals via the module electronics interface 1330, from the storage controller 1302, or from another device and selectively activate one or more of the flow cell tools 1350. In this manner, the integrated circuit 1352 may operate the fluidic actuation device 1360 (e.g., by activating the electro-wetting surface to transport fluid), the sequencing actuation device 1362 (e.g., by activating electrochromic features to reduce crosstalk), or the synthesis actuation device 1364.

As an example, the integrated circuit 1352 may operate the well electrodes of the synthesis actuation device 1364 to produce desired electrical characteristics at one or more of the storage wells 1348. Electrical characteristics may include the presence or absence of current or voltage, as well as varying a magnitude, frequency, sequence, or other characteristics of current or voltage. The integrated circuit 1352 may be statically coupled with the underside of the flow cell 1322 and assembled within the case 706, and may additionally include illuminators, photodiodes, and/or other devices that are similarly operable by the storage controller 1302 or another device to aid in sequencing and synthesis within the storage wells 1348, such as described in relation to the electrode assembly 640.

When coupled to the flow cell 1322, a plurality of electrical connections of the integrated circuit 1352 will be aligned with and conductively coupled to the electrical circuitry of each electrode of the synthesis actuation device 1364, or similarly coupled with other features of the set of flow cell tools 1350. In some implementations, the electrical connections between the integrated circuit 1352 and the well electrodes may include a transparent conductive material, such as an indium tin oxide material to aid in durability and conductivity, while not obstructing illumination and optical imaging of the storage wells 1348 from the underside of the flow cell 1322. In some implementations, the transparent conductive material, as well as the structure of the well that the conductive material passes through, may be anisotropic in order to further control or confine the transmission of light into the wells. In some implementations, the conductive couplings between the well electrodes and the integrated circuit 1352 may include a plurality of conductive pads, positioned to contact each other and conduct electrical signals.

Figure 12C:
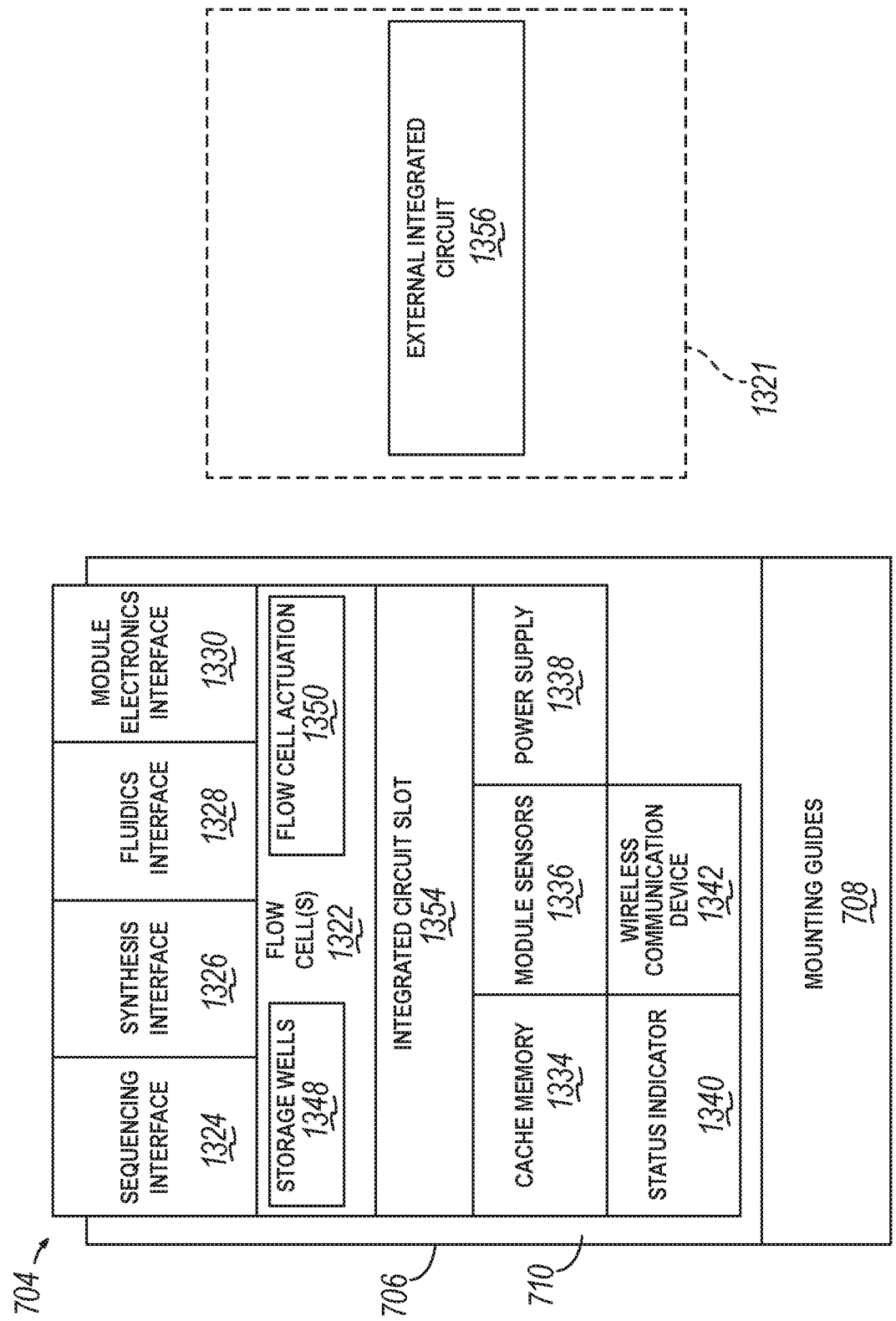
FIG. 12C depicts a schematic diagram illustrating yet another alternative example of a storage device usable with the polynucleotide storage system of FIG. 11.

FIG. 12C shows an alternate example of a storage device 704, usable with a DNA storage system such as the DNA storage system 1300. The storage device 704 includes several of the features of the storage device 702 of FIG. 12B. However, rather than including the integrated circuit 1352, the storage device 704 includes an integrated circuit slot 1354. The integrated circuit slot 1354 is positioned beneath and proximate to the flow cell 1322; and is shaped and adapted to receive an external integrated circuit 1356 of the DNA storage system 1300 and place that integrated circuit into contact with the flow cell 1322 when the storage device 704 is coupled with the DNA storage system 1300. This may include an external integrated circuit 1356 being statically positioned within or proximate to the module receiver 1321 of the DNA storage system 1300 such that it is horizontally inserted into the integrated circuit slot 1354 as the storage device 704 is inserted; or may include an external integrated circuit 1356 that is mechanically positionable in the receiver, such that it is first horizontally inserted into the integrated circuit slot 1354 to achieve alignment with the flow cell 1322 and then vertically positioned into contact with the flow cell 1322. This may also include an external integrated circuit 1356 that is electronically positionable by the DNA storage system 1300 and may be freely inserted and removed from the integrated circuit slot 1354 by electronically operating a corresponding assembly of the set of instrumentation 1301.

The integrated circuit slot 1354 and corresponding external integrated circuit 1356 may be shaped and adapted to provide a repeatable, precise, temporary coupling of the external integrated circuit 1356 to the flow cell 1322. This precise coupling allows a plurality of electrical contacts of the external integrated circuit 1356 to align with and conductively couple with electrical contacts of the set of flow cell tools 1350 to allow for control and operation of those features. As an example, in the case of the sequencing actuation device 1364 including a plurality of well electrodes, the integrated circuit 1356 may align and couple with each well electrode of the synthesis actuation device 1364. Such an alignment may also align and allow any illuminating or optical sensing features of the external integrated circuit 1356 to align with a corresponding storage well 1348. The storage device 704 may be advantageous for some applications in that it allows for the external integrated circuit 1356 or CMOS, which may be associated with a relatively high level of complexity and cost, to be implemented as part of the set of instrumentation 1301 and used with a plurality of storage devices, rather than requiring each storage device to include its own integrated circuit.

Figure 17A:
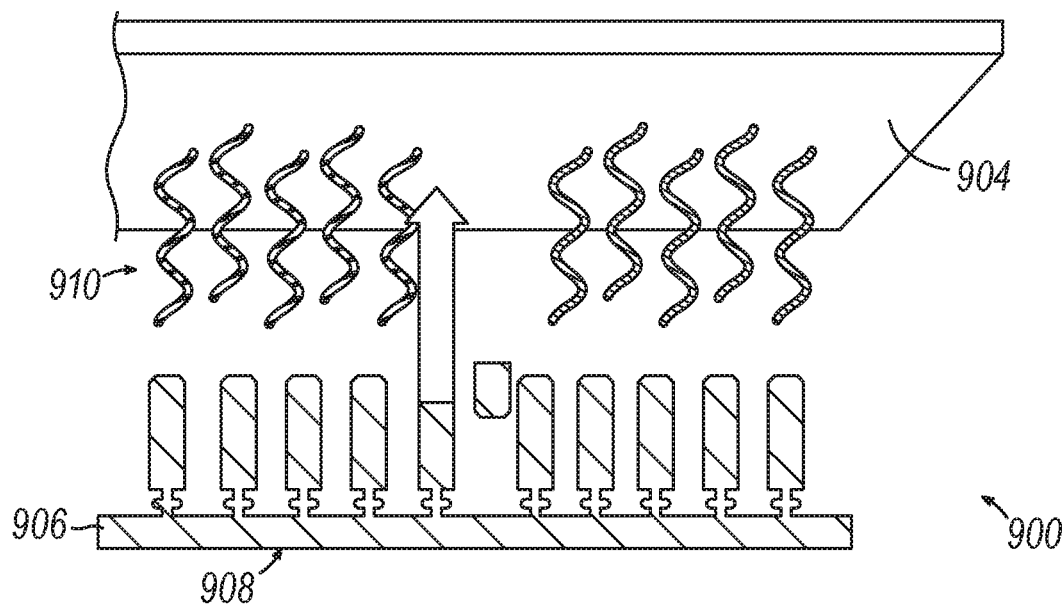
FIG. 17A depicts a schematic diagram illustrating a first aspect of a film replication process.

Some implementations of the above storage devices may include fewer components and features or additional components and features beyond those described above. As an example, FIGS. 15A and 15B shows an illustration of a process of copying DNA between a surface 906 and a film 904. With reference to an illustration 900 of FIG. 17A, the film 904 may be a thin film medium that may be inserted and removed from a storage device such as the storage device 700. The film 904 may be contained within a case or cartridge to aid in insertion to the storage device 700 and protect the film 904 during transport. The film 904 may contain a plurality of wells or designated areas that correspond to the storage wells 1348. The surface 906 may be a surface of the flow cell 1322 from which the storage wells 1348 are accessible.

In the shown example, the surface 906 includes a plurality of primers 908 (e.g., oligos), which may be positioned within each of the storage wells 1348 on a one-to-one basis. The film 904 includes a plurality of machine-written polynucleotides 910 that are positioned within the wells of the film 904 or at designated areas of the film that correspond to the storage wells 1348. The illustration 900 shows the film 904 being positioned proximately above the surface 906 such that the primers 908 may interact with the machine-written polynucleotides 910. During such interactions, the primers 908 are triggered by the machine-written polynucleotides 910, resulting in replication of each machine-written polynucleotides 910 that is in a well or area of the film 904 to a corresponding well of the surface 906.

Figure 17B:
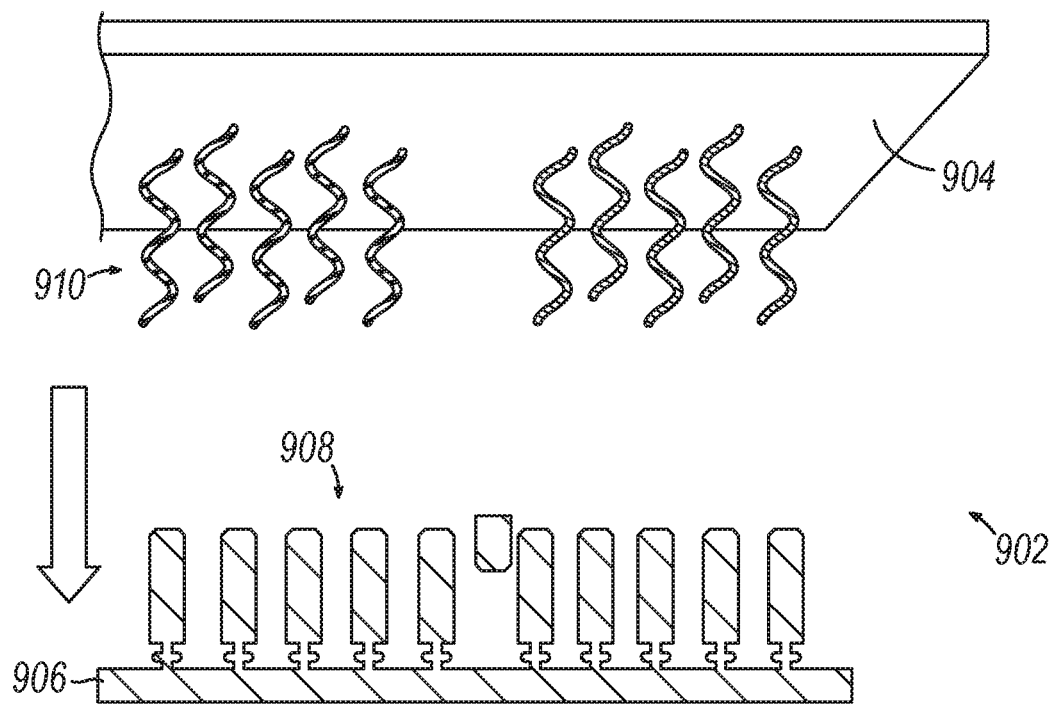
FIG. 17B depicts a schematic diagram illustrating a second aspect of the film replication process of FIG. 17A.

With reference to an illustration 902 of FIG. 17B, when the film 904 is then removed, the replica of machine-written DNA remains stored within the wells of the surface 906. As may be seen, machine-written DNA may be replicated into one or more wells of the surface 906 by insertion of the film 904. This may be useful to prepare and write machine-written DNA to the film 904 at a first location, using the DNA storage system 1300 or a similar device, and then replicate the machine-written DNA from the film 904 to the storage well 1348 of the storage device 700 in a second location. Transport of primers between the film 904 and the surface 906 may be performed by the set of instrumentation 1301, the set of flow cell tools 1350 or both. As an example, electrodes of the synthesis actuation device 1364 may be operated to attract or repel replicated machine-written DNA to a destination surface, or a flow of controlled fluid from the fluidic actuation device 1360 may transport the replicated machine written DNA to a destination surface.

The above process may also be used to copy machine-written DNA from the storage device 700 to the film 904, which may then be transported and sequenced or read elsewhere. For example, the film 904 may be prepared with the plurality of primers 908 corresponding to wells of the surface 906, while the wells of the surface 906 contain a plurality of machine-written polynucleotides 910. The film 904 may be inserted into the storage device 700 and positioned proximately to the surface 906 so that the machine-written polynucleotides 910 are replicated from the surface 906 onto the film 904. The film 904 may then be transported to and read by the DNA storage system 1300 or a similar device. Each of the above may also be performed by creating the replicate strand of DNA in place (e.g., within a well of the surface 906 from a strand within the well or on the film 904 from a strand present on the film 904), and then transferring and binding the replicate strands electrophoretically to their corresponding destination. Such transfer may also be performed by blotting the replicate surface to the destination surface through physical contact or by using the fluidics device 1308 or another device.

C. Methods for Managing DNA Hard Drive Module

As described in relation to the cache memory 1334, it may be advantageous to use caching strategies to manage writing and reading of data with storage devices, such as the storage device 700 and others. As an example, where data is being written to the storage device 700 and a user initiates dismounting of the volume from the set of instrumentation 1301 of the DNA storage system 1300 before writing to the flow cell 1322 may be completed, unwritten data may be stored on the electronic memory and will travel with the storage device 700 until such a time that it may be written to the flow cell 1322. As another example, where an index of well contents, file locations, or other similar data is maintained for the storage device 700, it may be useful to maintain that index on an electronic memory that travels with the storage device 700 instead of, or in addition to, storing the index in a cloud storage or on a permanent storage volume of the set of instrumentation 1301 of the DNA storage system 1300. In this manner, if the storage device 700 is transported and mounted with a set of instrumentation 1301 of a different DNA storage system 1300 the well index is immediately available, rather than requiring information be obtained from the cloud storage volume or from a set of instrumentation 1301 of a previously coupled DNA storage system 1300.

Figure 13:
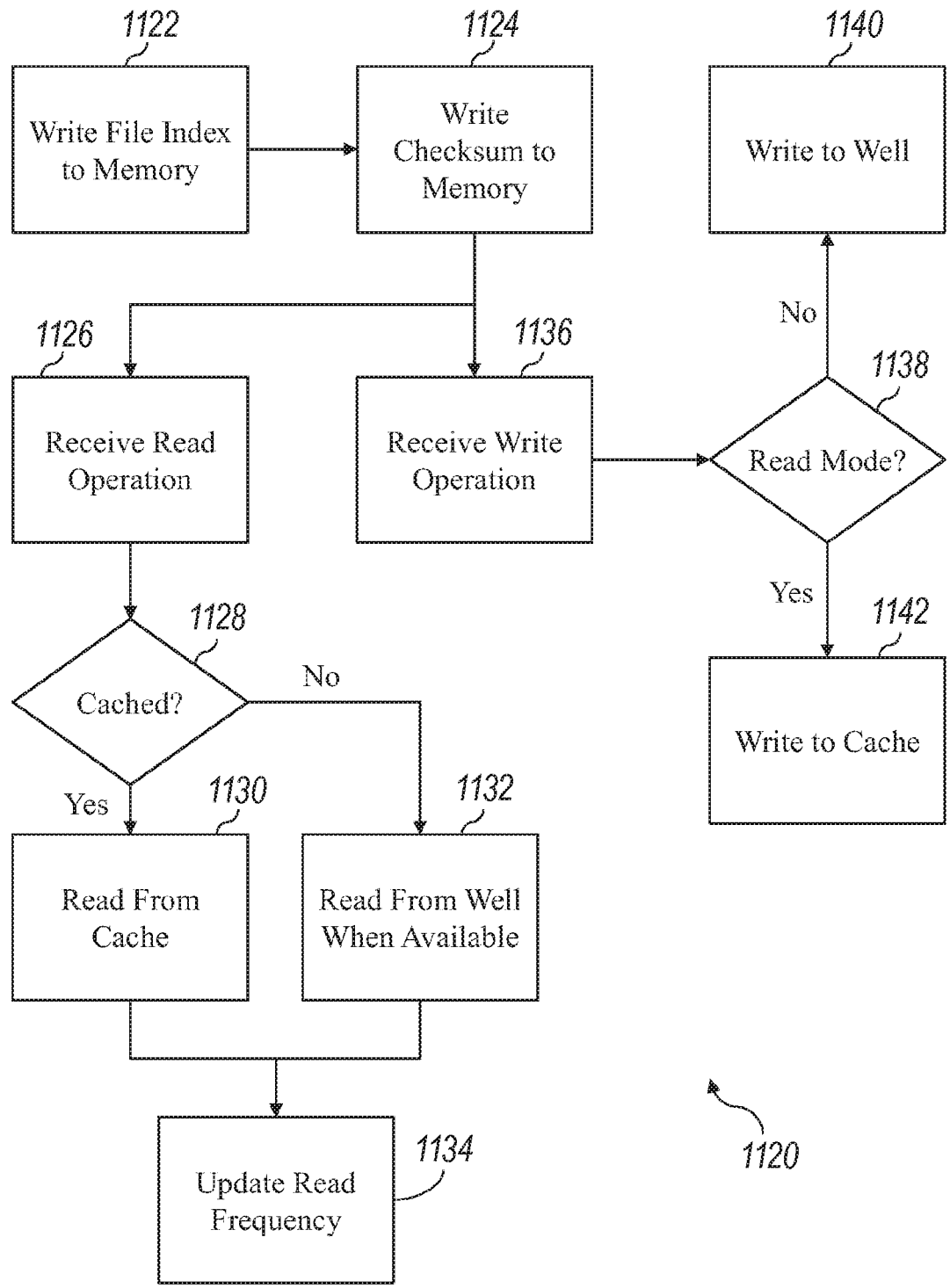
FIG. 13 depicts a flowchart of a process that may be performed to provide caching of read and write operations to the storage device of FIG. 15.

As another example of a caching strategy, FIG. 13 depicts a flowchart of a process 1120 that may be performed to provide caching of read and write operations to the storage device 700, when an electronic memory such as the cache memory 1334 is available. As data is written to the storage device 700 with the DNA storage system 1300, additional data may be written to the cache memory 1334. This may include writing (block 1122) a file index to the cache memory 1334, which may describe the contents of a plurality of wells and locations of particular files or data, whether stored in the plurality of wells, stored on the cache memory 1334, or both. Such information may be used to enable later access to and retrieval of requested data. Checksum data for individual files or bundles of data may also be written (block 1124) to the cache memory 1334 and may be associated with the file index.

Storing an index, a list of checksums, or both for files and data on the cache memory 1334 may enable faster reading and writing of data in the future, as compared to storing such data on the flow cell 1322 and requiring it to be sequenced or storing such data on a cloud storage or server and requiring it to be accessed and retrieved, before the drive contents are accessible. Storing such data on the cache memory 1334 in addition to storing it in other locations (e.g., on the flow cell 1322 itself or on a network accessible volume) provides an additional advantage of redundant storage of such data, as the loss of file tables and indexes may result in either the complete loss of data stored on the flow cell 1322 or a greatly increased cost in time and resources to rebuild the file indexes based upon well-by-well examination.

While the storage device 700 is coupled with the DNA storage system 1300, the system may receive (block 1126) read operations, may receive (block 1136) write operations, or both from users or from systems and devices in communication with the DNA storage system 1300. As has been discussed, in some cases it may not be possible to allow for simultaneous reading and writing of data to separate wells of the flow cell 1322. This may be due to limitations of the DNA storage system 1300 or limitations on the storage device 700. As an example, some implementations of the storage device 700 may be considered to have two mutually exclusive modes: a read mode and a write mode. Due to the distinct fluidics, well conditioning, and other devices that are required for each operation, simultaneous reading and writing may be unreliable or impossible. Further, there may be a cost in time and wasted reagents to switch from read mode to write mode. While such implementations may particularly benefit from the disclosed caching strategies, it should be understood that even implementations that support simultaneous reading and writing may encounter various scenarios where they may benefit from caching strategies.

Where a read operation is received (block 1126), the DNA storage system 1300 may examine the file index to both locate the requested data and determine whether it is currently stored (block 1128) on the cache memory 1334. Requested data may be available on the cache memory 1334 in different scenarios. As an example, where data is written to the storage device 700 and then requested shortly after, it may still be stored in the cache memory 1334. As another example, where data was recently read from the flow cell 1322 based upon a request, it may be stored in the cache memory 1334 until overwritten. As another example, the DNA storage system 1300 may be configured to flag certain data that is stored on the flow cell 1322 to be also maintained in the cache memory 1334 when possible. Such configuration may be a manual configuration provided by a user or may be based upon an automatic determination by the DNA storage system 1300 that itself is based upon the frequency of read requests for such data.

Where the requested data is available from the cache memory 1334, the DNA storage system 1300 will read (block 1130) the data from the cache memory 1334 to service the request, which may allow the storage device 700 to be maintained in a write mode, while simultaneously allowing data to be read (e.g., from the cache memory 1334 and not from the flow cell 1322). Where the requested data is not stored in the cache memory 1334, the DNA storage system may read (block 1132) the data from the flow cell 1322 when such functionality is available (e.g., when the storage device 700 is in read mode or when a read operation is otherwise available). Where the storage device 700 is in write mode and actively writing data to the flow cell 1322, it may not be advantageous to prioritize switching back to read mode, due to the time and reagent cost in switching between modes. However, where data that is queued to be written is of a size that may be stored on the cache memory 1334, it may be advantageous to switch to read mode and allow the requested data to be read (block 1132) from the well, while input data is stored on the cache memory 1334. In such a case, a user or other system or device that has requested data be written and read perceives that such actions are being performed simultaneously, since output data is being read from the flow cell 1322 while input data is being written to the cache memory 1334.

After each read operation, the file index on the cache memory 1334 or another data set may be updated (block 1134) to reflect the read frequency for recently requested data, with such data sets being useful for future determinations for data that should be cycled into the cache memory 1334 due to frequency of use (e.g., data that may be requested every single data) or patterns of use (e.g., data that is requested every Friday may be cycled into the cache memory 1334 on Thursday at a low priority such that it is completed during a period of time where there may be reduced requests for reading and writing of data).

With continued reference to FIG. 13, where a write operation is received (block 1136), the DNA storage system 1300 may determine (block 1138) whether the storage device 700 is currently in read mode. Where the storage device 700 is currently in read mode, the input data associated with the write operation may be written (block 1142) to the cache memory 1334 and flagged for writing to the flow cell 1322 when available. Where the storage device is already in write mode, the input data may be written (block 1140) to one or more wells of the flow cell 1322.

The disclosed caching methods may also be influenced by a caching strategy that gives preference to staying in a current mode (e.g., read mode or write mode) over other considerations, such that all queued read operations may be performed before switching to a write mode, regardless of the order of arrival of the requests, and may even maintain a read mode for a brief period of time past completion of the last read request in order to allow for other read requests to arrive and be serviced before switching modes. In addition to reducing the overall number of mode switches performed in a given period of time, such a strategy reduces the risk of cross contamination of read-specific reagents with write-specific reagents, which may otherwise occur more frequently as a result of more frequent switching of modes.

Figure 14:
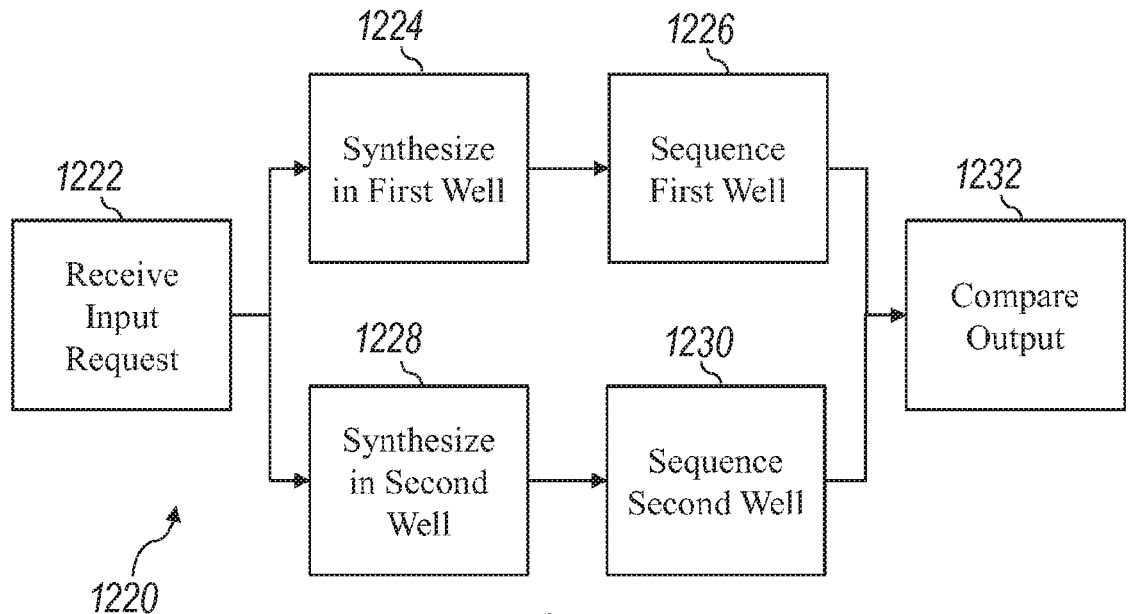
FIG. 14 depicts a flowchart of a process that may be performed to provide redundant data writing and reading with a storage device.

The storage device 700 may also benefit from data cloning and data fragmenting strategies when writing and reading data from the flow cell 1322. As an example, FIG. 14 depicts a flowchart of a process 1220 that may be performed to provide redundant data writing and reading operations with a storage device such as the storage device 700. When an input request is received (block 1222) that provides input data that should be written to wells of a flow cell, the DNA storage system 1300 may, in parallel or in close sequence depending upon its capabilities, synthesize (block 1224) and store the input data in a first well and synthesize (block 1228) and store the input data in a second well. While FIG. 14 describes a first well and a second well, it should be understood that data may advantageously be performed across three or more wells. The redundancy of the first well and second well may be used for error checking, such as by sequencing one or both of the polynucleotides of the first well and/or second well to determine if phasing or pre-phasing occurred during a read and/or write process. Assuming there were no errors in synthesis, identical copies of the machine written polynucleotides corresponding to the input data in the first well and the second well. This provides various advantages, depending upon the nature of the first well and the second well. As an example, with reference to the storage device 700, the first well may be located in a first of the flow cells 1322, while the second well may be located in a second of the flow cells 1322. In such a case, the written data is redundantly stored across two separate flow cells, which is desirable for data integrity and minimizing risk of data loss.

Even where another storage device, such as the storage device 1320, is used and the first well and second well are each located in the flow cell 1322, there are some advantages to cloning data cross individual wells in the same flow cell. In addition to providing data redundancy to reduce the risk of data loss to a well malfunction or unexpected degradation of DNA within one well, cloning the written data may provide additional error checking capabilities, regardless of where the two wells are located. As an example, where the input data is written to separate wells as shown in FIG. 14, it may then be read back from the two separate wells by sequencing (block 1226) and reading the data from the first well, and sequencing (block 1230) and reading the data from the second well. A comparison (block 1232) of the output that is read from each well or a checksum of the output will indicate whether the polynucleotide written to one cell was either erroneously synthesized or has subsequently degraded for some reason.

In some implementations, the synthesizing of a polynucleotide in the second well may be done based on the synthesizing of the polynucleotide in the first well. That is, clonal amplification of the polynucleotide written in the first well may be performed and one or more cloned polynucleotides may be stored in second well and/or in a fluidic storage chamber. Sequencing of the clonally amplified polynucleotides within the first well may be performed to determine the sequence of nucleotides in the first well. The sequence of nucleotides in the first well may be compared to the instructed written polynucleotide to determine if any phasing or pre-phasing errors occurred during the write process. If an error occurred, the one or more cloned polynucleotides stored in second well and/or in a fluidic storage chamber may be discarded as corrupt and the write process may occur again. If no errors occurred, then the one or more cloned polynucleotides stored in second well and/or in a fluidic storage chamber may be cloned and stored in the first well and/or one or more other wells to provide two or more identical polynucleotides described herein.

Figure 15:
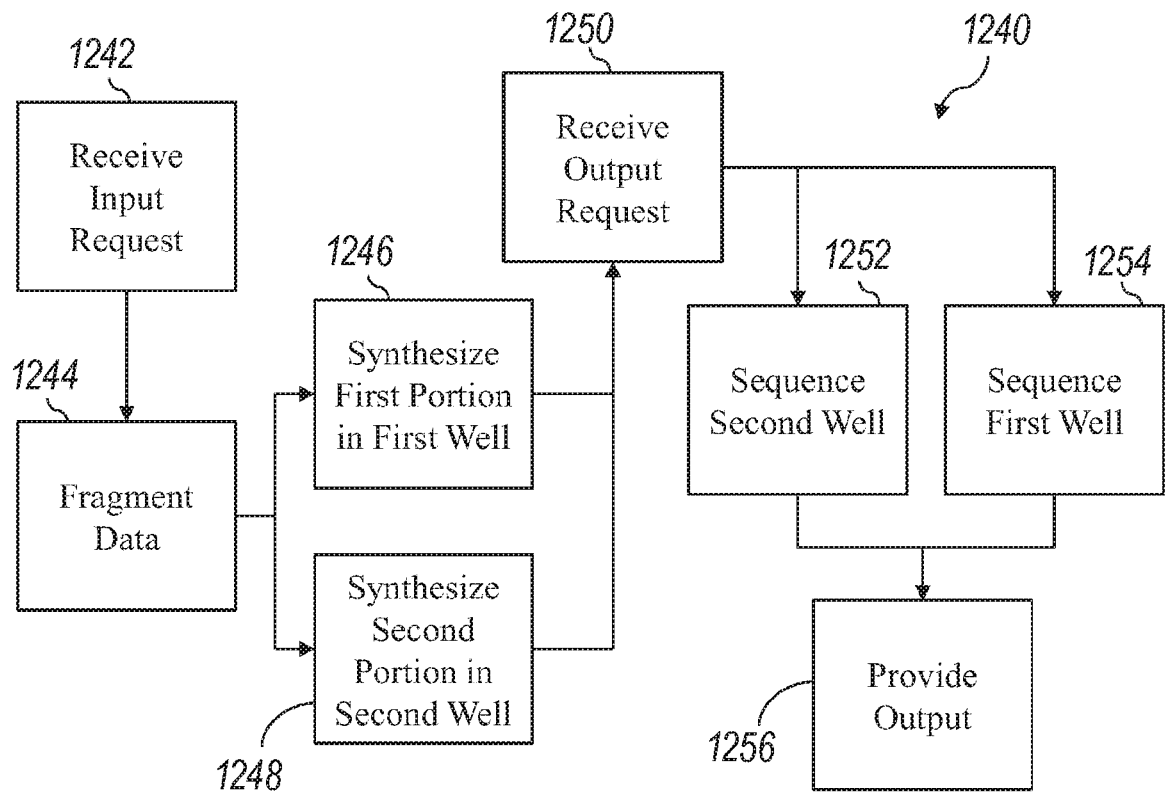
FIG. 15 depicts a flowchart of a process that may be performed to provide high speed data writing and reading with a storage device.

FIG. 15 depicts a flowchart of a process 1240 that may be performed to provide high speed data writing and reading with a storage device. The process of FIG. 15 may be performed using the storage device 700. When an input request is received (block 1242), the DNA storage system 1300 may fragment (block 1244) the data associated with the input request into multiple portions (e.g., two or more). Rather than writing the entire input into a single well, the system may synthesize and write (block 1246) the first portion into a first well and, in parallel, synthesize and write (block 1248) the second portion into a second well. Where the first well and the second well may be separately synthesized in this manner without impacting the write speed of the other, the result is that the input data may be completely written to DNA storage about twice as fast, relative to writing the entire input to a single well. Similarly, when an output request is received (block 1250), the DNA storage system 1300 may sequence (block 1252) and read the second portion from the second well and, in parallel, sequence (block 1254) and read the first portion from the first well. The two portions may then be reassembled, and the complete output may be provided (block 1256). In this case also, the output data may be read from DNA storage at an increased speed, relative to reading the data from a single well.

D. Methods for Mounting and Dismounting DNA Hard Drive

As has been discussed, some implementations of the disclosed DNA hard drives may be temporarily coupled with and removable from the DNA storage system 1300; and may be intended for portability between the DNA storage system 1300 and other systems, devices, or storage locations. In such cases and others where a DNA hard drive, such as the storage device 700 of FIG. 12A, may be coupled with and decoupled from the DNA storage system 1300 for any reason, the DNA storage system 1300, the storage device 700, or both may be configured to perform certain processes during mounting (e.g., coupling) with the DNA storage system 1300 and during dismounting (e.g., decoupling) from the DNA storage system 1300.

Figure 16A:
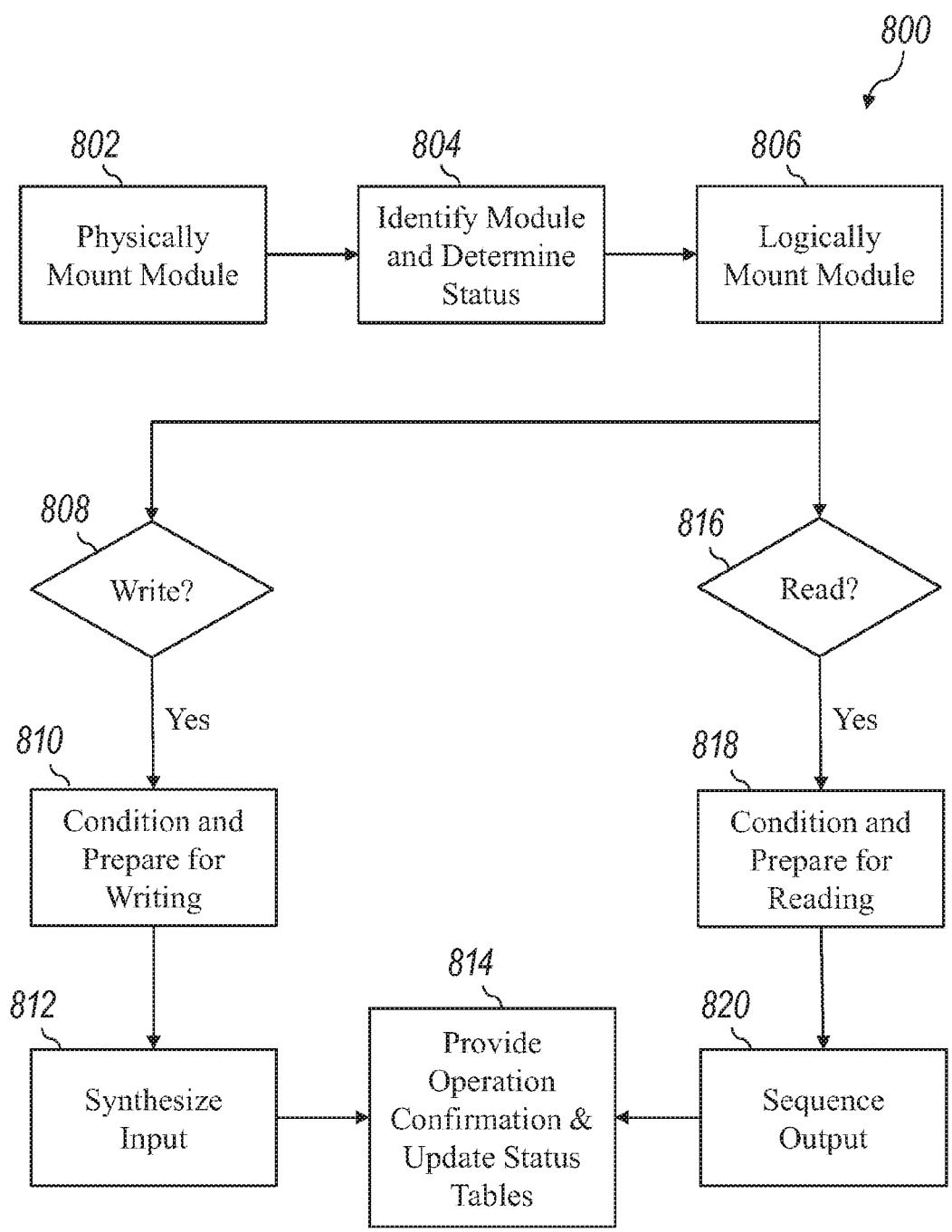
FIG. 16A depicts a flowchart of a process that may be performed with the polynucleotide storage system of FIG. 11 to mount the storage device of any of FIGS. 12A-12C.
Figure 16B:
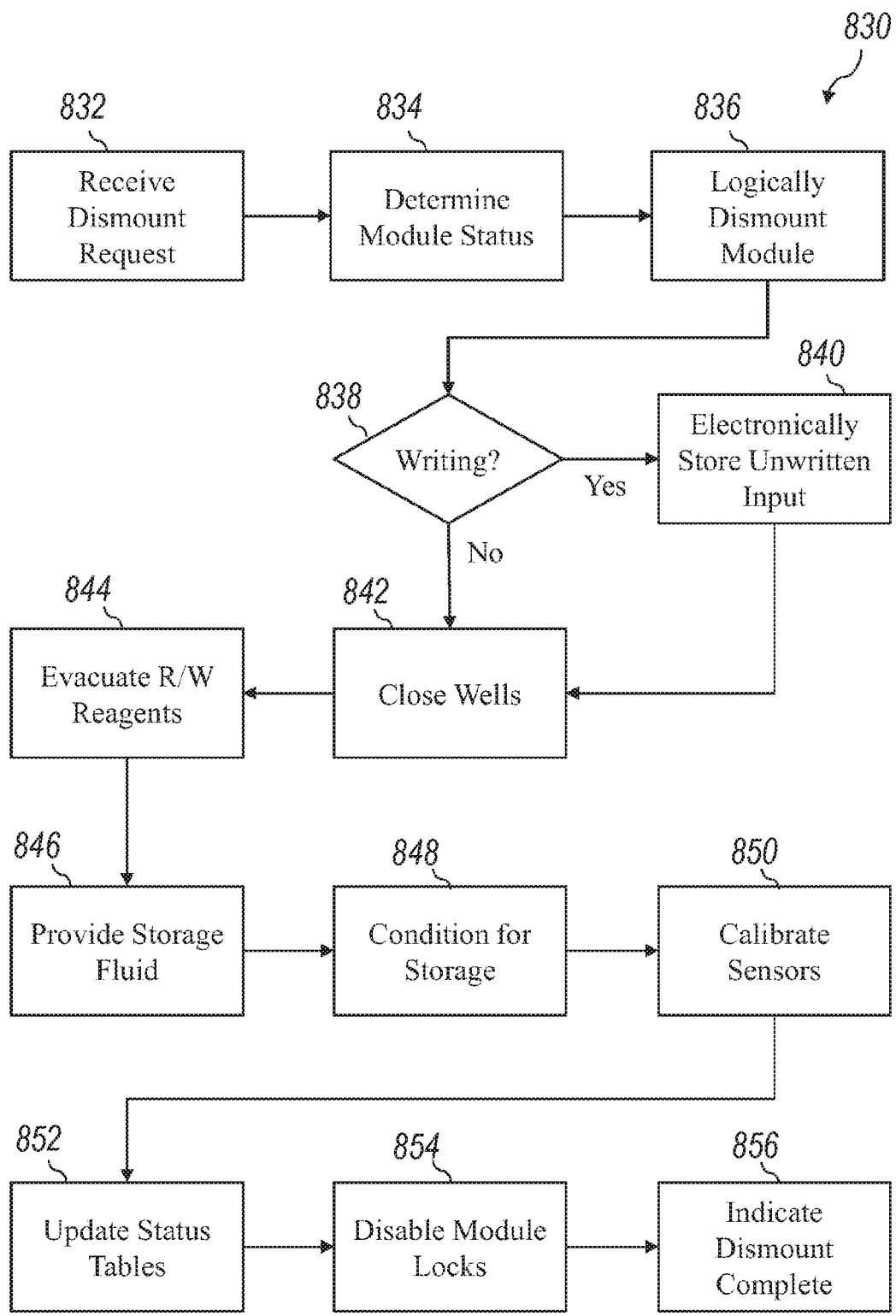
FIG. 16B depicts a flowchart of a process that may be performed with the polynucleotide storage system of FIG. 11 to dismount the storage device of any of FIGS. 12A-12C.

As an example, FIGS. 14A and 14B show processes that may be performed with the systems and storage devices disclosed herein, such as the DNA storage system 1300, when mounting and then dismounting a storage device, such as the storage device 700. FIG. 16A shows a process 800 that may be performed to mount and make a storage device available for reading and writing of data. The storage device 700 may be physically mounted (block 802) to the DNA storage system, such as by inserting the storage device 700 into the module receiver 1321 slot or compartment until fully seated, as may be indicated by physical feedback from one or more mounting guides 708 or an audible response, visible response, or other indication produced by a user interface of the DNA storage system 1300. The DNA storage system 1300 may then identify (block 804) and determine status information for the storage device 700, which may include identifying a type or model number, uniquely identifying that particular storage device 700 based upon an identifier, or identifying well index or file index information associated with the storage device 700, for example.

Identification (block 804) of the storage device 700 may be performed in varying ways, including by way of an optical scanner of the DNA storage system 1300 aligning with and identifying an optical code on the case 706, a wireless transceiver receiving information from an RFID memory or other wireless communication device 1342, or the storage controller 1302 receiving information from the cache memory 1334. Determination (block 804) of well status, file status, and other information may be performed by receiving such information from the cache memory 1342 via a wired or wireless connection. Determination (block 804) may also be performed using the unique identity of the storage device 700 to query another device or component where such information is stored, such as where the storage controller 1302 may access a locally available storage drive or remotely available storage drive to determine such information.

The DNA storage system 1300 may then logically mount (block 806) the storage device 700, which may include reconfiguring its own software, such as an operating system, file system, or software application, to indicate that the storage volume 700 is prepared to be used for reading and writing of data as a storage volume the DNA storage system 1300.

Where a write request is received (block 808) with a set of input data, the DNA storage system 1300 may condition and prepare (block 810) the storage device 700 for writing data to one or more of the storage wells 1348 and then synthesize (block 812) machine-written DNA within those wells corresponding to the received input data. As has been described, this may include activating one or more of the set of instrumentation 1301 to provide reagent fluids, thermal inputs, optical inputs, and others inputs to the storage device 700 in order to create the desired sequence of nucleotides for a machine-written polynucleotide within the well, where the desired sequence of nucleotides is determined by encoding the set of input data into a DNA format based upon an encoding scheme. The desired sequence of nucleotides may also include other information appended to the set of input data, which may include hash or checksum information, markers indicating the end or beginning of a particular file or data set, or other information. The desired sequence of nucleotides may be synthesized within the well as machine-written single strand DNA, machine-written double strand DNA with each individual strand mirroring the other, or both.

After completion of the write operation, the DNA storage system 1300 may provide (block 814) confirmation of the operation and update one or more status tables to reflect the completion of the operation. Confirmation information may include, for example, the time and date of the operation, a checksum or hash value of the input data, the storage wells 1348 affected by the operation, the identity of the storage device 700, and other information, some or all of which may be added to well status tables, file index tables, or other tables.

Where a read request is received (block 816) indicating output data that is desired, the DNA storage system 1300 may condition and prepare (block 818) the storage device for reading of data, as has been described, and then sequence (block 820) the requested output data from one or more of the storage wells 1348. A read request may be received (block 816) as a description of files or datasets, the locations of Which within the storage wells 1348 may be determined by using a well status table, file index table, or other similar directory. Conditioning (block 818) the storage device 700 for the read operation and sequencing (block 820) the data may include providing reagent inputs, thermal inputs, optical inputs, and other inputs to the affected storage wells 1348 and capturing output. As an example, output may include emitted light from an optically labelled nucleotide paired to the machine-written DNA within the storage wells 1348, which may be converted from a sequence indicative of the nucleotides of the machine-written polynucleotide to digital data matching the requested output data. After completion of the read operation, the DNA storage system 1300 may provide (block 814) confirmation of the operation and update one or more status tables. Confirmation of a read operation may include information such as identification of the storage well 1348 read, pre-synthesis checksums, post synthesis checksums, the output data, as an encoded nucleotide sequence or decoded to digital form, and other information.

While mounted, the storage device 700 may perform a number of read and write operations, until a dismount request is received (block 832), A dismount request may be as a result of a manual interaction with the DNA storage system 1300, such as by pressing a button to indicate the storage device 700 needs to be removed or automatically as a result of the storage device 700 being at or near its storage capacity. When received, the DNA storage system 1300 may determine (block 834) a status of the storage device 700, such as whether it is currently being written to or read from. In some implementations, where a current operation is being performed, the DNA storage system 1300 may delay further processes until the read or write operation is complete.

In some implementations, the DNA storage system 1300 may terminate read or write operations before their completion, either in response to any dismount request or in response to a high priority or immediate dismount request. In such cases, the DNA storage system 1300 may immediately logically dismount (block 836) the module, by configuring its operating system, file system, or a software application to reflect that the storage device 700 is no longer available for read or write operations to devices or software applications that interact with the storage device 700. The DNA storage system 1300 may then determine if the storage device 700 is currently in process of writing (block 838) and, if it is, may write the unwritten portion of input data to a location such as the cache memory 1334. In this manner, where a file or dataset is only partially written to the storage wells 1348, the unwritten portions may be stored (block 840) to the cache memory 1334, as it may be advantageous to keep both portions of the file physically grouped together on the same storage device 700.

After storing (block 840) an unwritten portion of input, or when the storage device 700 is unused or involved in a data read process, the DNA storage system 1300 may take any necessary actions to close out (block 842) any wells that are currently or have recently been involved in a read or write operation. After a recent synthesis operation, this may include providing any closing nucleotide sequences or reagents required to safely store the DNA in its current form or protect the DNA from degradation. The DNA storage system 1300 may then evacuate (block 844) any reading or writing reagents or other fluids from the storage device 700 using the fluidics device 1308 and may also provide (block 846) a storage fluid to the storage device 700. The storage fluid may include a preservative or other fluid configured to protect and preserve machine written DNA within the storage well 1348 and may, for example, either fill the individual wells or provide a thin protective coating for each well. Preservative fluids may include, for example, an antioxidant, a desiccant, a polymer coating, or other substances or combinations of substances, such as a liquid polymer coating that carries antioxidant. During future mounting of the storage device 700 the protective coating may be flushed and removed prior to subsequent writing or reading of the storage device 700.

The DNA storage system 1300 may also perform other processes to condition (block 848) the module for storage, which may include lowering the temperature of the storage device 700 (e.g., lowering the temperature of the flow cell 1322, within an insulated case 706) and lowering the humidity of the interior 710, to allow for stable transport of the storage device 700 to a temperature and humidity controlled storage area. As one example of a conditioning (block 848) process, the DNA storage system 1300 may freeze thy the flow cell 1322 by providing thermal inputs and pressure inputs to sublimate liquids within the flow cell 1322 and then evacuate the liquids in gaseous form. Depending upon the amount of time required to safely freeze dry the flow cell 1322, conditioning (block 848) by freeze drying may be performed by a sub-system or separate device of the DNA storage system 1300, such that the storage device 700 may be removed from the DNA storage system's 1300 primary module receiver 1321 and placed in an alternate receiver that is not capable of reading or writing machine written data to the storage well 1348, but is capable of interfacing with the storage device 700 to provide conditioning (block 848), Such a device may be proximate to the DNA storage system 1300 or may be located in an environmentally controlled storage area where the storage device 700 will be archived.

The DNA storage system 1300 may also calibrate (block 850) one or more module sensors 1336, where present. This may include, after conditioning (block 848) the storage device 700, configuring and calibrating the module sensors 1336 to provide accurate sensing of temperature, humidity, light, motion, radiation, or other detectable characteristics, based upon known values for those characteristics at the time of conditioning (block 848) (e.g., temperature and humidity of the flow cell 1322 will be known based upon configured conditioning values for those characteristics, while motion, light, and radiation may be assumed to be near-zero while the storage device 700 is coupled with the DNA storage system 1300 or a sub-system). Calibration (block 850) of sensors may also include calibrating, configuring, or enabling one or more sensors associated with a room where the storage device 700 will be stored or associated with a particular rack, shelf, or storage enclosure in which the storage device 700 will be stored. As another example, one or more storage devices may be optically daisy chained and an optical time-domain reflectometer may be utilized to collectively monitor aspects of the storage devices.

The DNA storage system 1300 may also update (block 852) one or more status tables stored on the cache memory 1334 or another memory, to reflect the time and date of dismounting, the processes performed while dismounting (e.g., indicating whether the storage device 700 was provided (block 846) a preservative fluid or coating and the type, the state that the storage device 700 was conditioned (block 848), whether the storage device 700 contains any unwritten input data stored (block 840) on the cache memory, and other information that may be useful when the storage device 700 is later mounted.

The DNA storage system 1300 may also disable or remove (block 854) one or more module locks that physically immobilize the storage device 700 within the module receiver 1321 or slot of the DNA storage system 1300 with which it is coupled. These may include electronically operated or released latches that grip the mounting guides 708 or other portions of the case 706 and fix the storage device 700 in place after it is physically mounted (block 802). Once the storage device 700 may be safely removed without loss of data or damage to equipment, the DNA storage system 1300 may indicate (block 856) that dismounting of the storage device 700 is complete by providing an audible, visible, or other output via a user interface of the DNA storage system 1300.

As with other examples, it should be understood that the processes shown FIGS. 14A and 14B are examples and that various mounting and dismounting procedures may include fewer processes than shown or additional processes that are not shown, with such variations being apparent to those skilled in the art in light of this disclosure.

VIII. Separation of Dedicated Reading and Writing Locations

Figure 18:
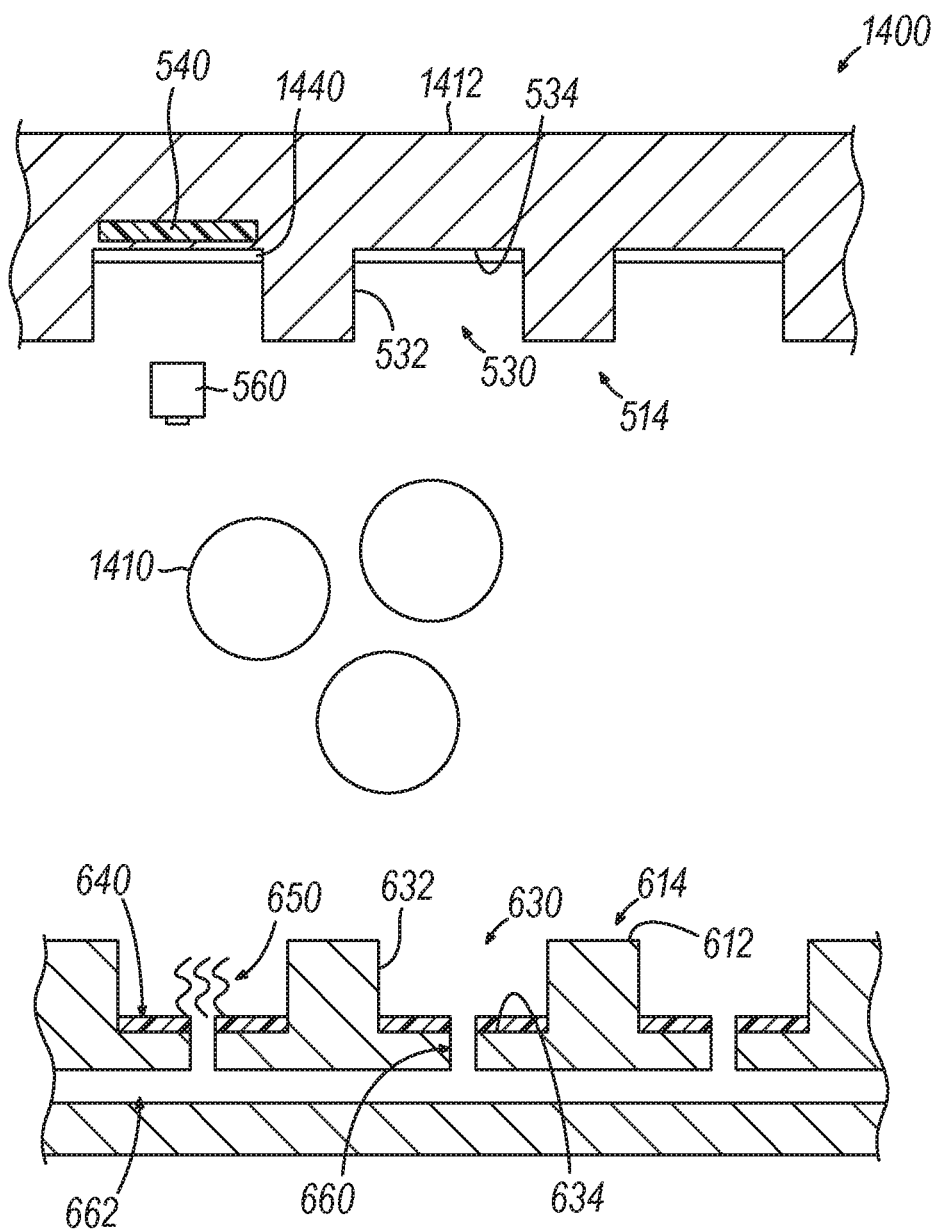
FIG. 18 depicts a block schematic cross-sectional view of another example of wells that may be incorporated into the channel of FIG. 4.

In some implementations, further variations on the reading of data encoded in the form of nucleotide sequences may also be possible. For example, in some implementations, when data is to be read, rather than sequencing the strands used to encode the data, those strands may first be copied (e.g., via PCR) and the data may be read by sequencing the copies, thereby reducing the risk that sequencing may introduce errors into the originals. FIG. 18 provides a not to scale illustration of a portion of a channel within a flow cell 1400 that is an example of a variation of the flow cell 400. In other words, the channel depicted in FIG. 18 is a variation of the flow channel 410 of the flow cell 400. In this example, wells 530 for reading nucleotide sequences such as shown in FIG. 5 are included in the top surface 1412 of the channel, while wells 630 for writing nucleotide sequences such as shown in FIG. 6 are included in the base surface 612. To support this, in some implementations, each of the surfaces of the flow cell 1400 may have dedicated control circuitry, such as a first dedicated CMOS circuit for the writing wells on the base surface 612, and a second dedicated CMOS circuit for the reading wells on the top surface 1412.

In this example, in addition to components described previously in the context of FIG. 5 and FIG. 6 for writing and reading machine-written polynucleotides, the flow cell 1400 also includes a plurality of beads 1410 that may be used to transfer copies of machine-written polynucleotides 650 from the wells 630 in the base surface 612 to the wells 530 in the top surface 1412. In some implementations when a write command was to be executed using a DNA storage device comprising a flow cell 1400 having the configuration of FIG. 18, one or more wells 630 on the write surface (e.g., the base surface 612) may be identified as unused, and polynucleotides encoding the data to be written may be synthesized in those wells 630 in the manner described previously in the context of FIG. 6. Additionally, in some implementations, when machine-written polynucleotides are synthesized on a flow cell 1400 configured as shown in FIG. 18, those strands may be synthesized to include not just the data that was the subject of the write request, but also binding sequences that may match sequences that had previously been fixed to the surface of the beads 1410.

In some implementations, when a read request was received for data that had been stored in a flow cell 1400 configured as shown in FIG. 18, one or more beads 1410 may be moved to the well 630 where the strands 650 had been written. In some implementations, this may be done by using electrode(s) 640 in the well 630 to generate a magnetic field which may attract the bead(s) 1410 (e.g., in an implementation where the beads were paramagnetic) or an electric field to attract the bead(s) 1410 (e.g., in implementations where the beads had a charge and may be attracted by electrophoretic means). In other implementations, such as where the electrode(s) 640 in the well 630 were not strong enough to generate the requisite field, a separate electrode may be used that may attract the beads to, or close to, the well 630 where the strands 650 had been written. Once the beads 1410 had moved, the strands 650 may be copied and the binding sequences on the copies may adhere to the matching sequences that had previously been fixed to the surfaces of the beads 1410. The electrode(s) that had been used to move the bead(s) 1410 to the location where the strands were transferred to it may then be deactivated, and the bead(s) 1410 may be transferred to the location where the copied strands may be read. For example, in some implementations, electrodes 1440 in a corresponding well 530 on the opposite surface (e.g., the top surface 1412) may be activated to transfer the beads 1410 to that corresponding well 530. Alternatively, in some implementations, a magnet or electrode that did not correspond to an individual well (e.g., a magnet moved into physical proximity of the top surface 1412 of the flow cell) may move the bead(s) 1410 to a location where the copied strands may be read, rather than necessarily moving them to a particular reading well corresponding to the well in which the strand(s) were originally written. The copies may then be sequenced as described previously in the context of FIG. 5, thereby allowing the data to be read without the increased risk of data corruption that may be associated with sequencing the original strands.

In some implementations, other relationships between beads and wells may also be possible. For example, in some implementations, rather than using beads 1410 to transport sequences that are originally written into wells 630 in the base surface 612 of the cell 1400, machine-written polynucleotides 650 may be written directly onto beads themselves. For example, in some implementations, when data is to be encoded into machine-written polynucleotides 650, magnetic beads 1410 having primers fixed directly to their surfaces may be transferred to the appropriate well(s), and the machine-written polynucleotides may be built from those primers rather than (or in addition to) primers on the surface(s) of the well(s). In some implementations of this type, when machine-written polynucleotides are synthesized, they may be synthesized to include not only the data being written to the DNA storage device, but also to include a predetermined sequence identifying the well in which it was synthesized, thereby enabling data address information to be maintained even though the sequence may never have been physically fixed to an addressable well.

Figure 19:
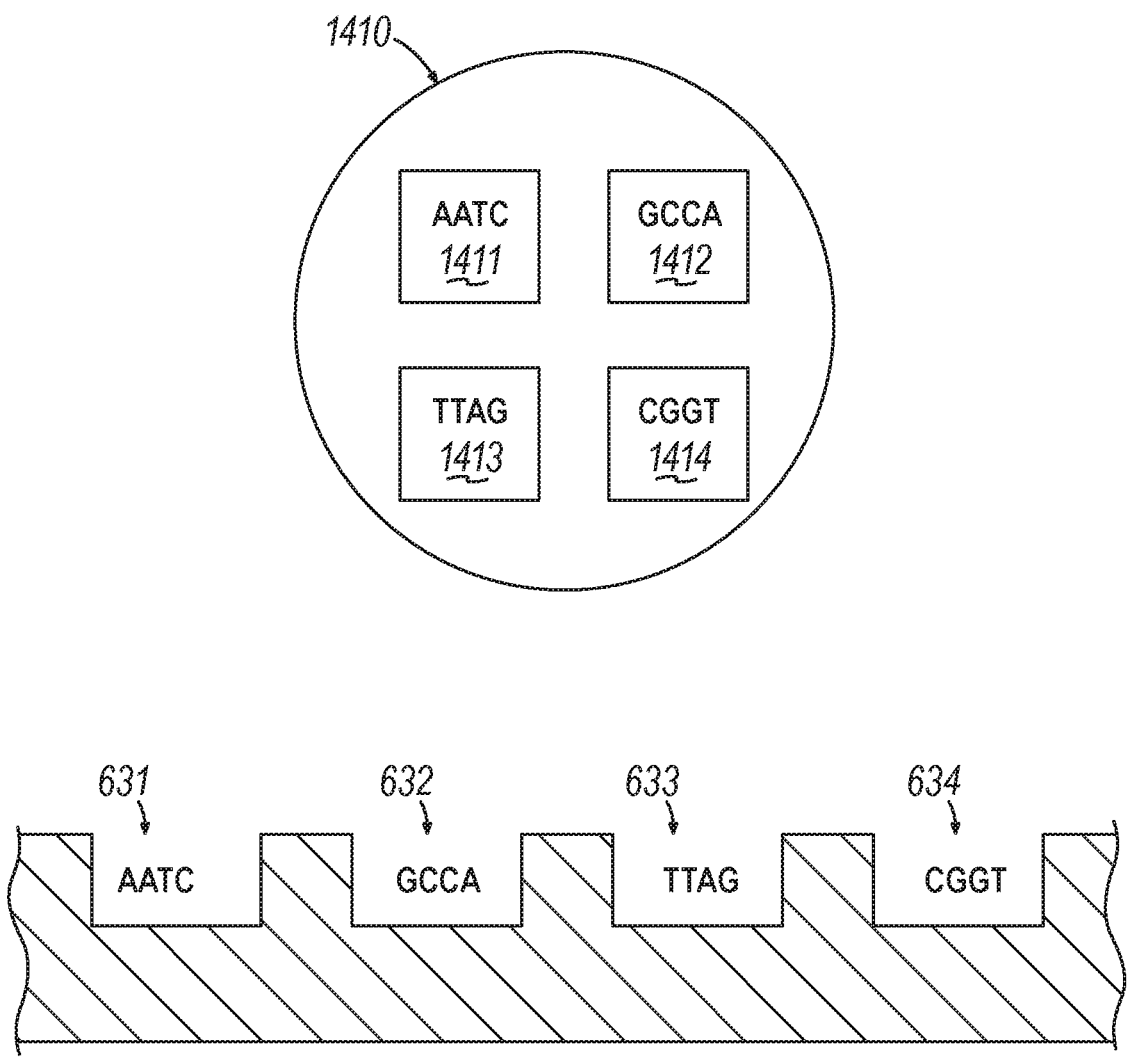
FIG. 19 depicts a block schematic view of an example of a relationship between a bead and a flow cell.

In some implementations, addressing data such as described above may also (or alternatively) be used to support multiplexing data from multiple write wells through beads that may transfer machine written strands from those wells to reading wells in another surface of the flow cell. For example, in some implementations, magnetic beads 1410 may be provided that have oligos matching n different sequences fixed to their surfaces (e.g., x oligos matching sequence 1, x oligos matching sequence 2, . . . , x oligos matching sequence n). These sequences may then be treated as channel identifiers, with the beads functioning as a multiplexed n-channel connection between the write and read surfaces of the flow cell. In some implementations, this may be practiced using beads barcoded with unique sequences corresponding to wells in a write surface of a flow cell. A simplified (e.g., by depicting barcode sequences of length 4, rather than the longer sequences that may preferably be used in practice) of this is illustrated in FIG. 19. In an implementation configured as shown in FIG. 19, when data was to be encoded, it may be written into a machine-written polynucleotide that may include not only the data but also one of the sequences on the surfaces of the beads 1410 corresponding to the well it was written to. For example, when data was to be written to a first well 631 it may be written in a machine-written polynucleotide that may include not only the data but also the sequence corresponding to the first well—i.e., AATC. Similarly, when data was to be written to the second well 632, third well 633, or fourth well 634, it may be written in a machine-written polynucleotide that included not only the data but also the sequence corresponding to the well it was written to—i.e., GCCA (for the second well 632), TTAG (for the third well 633) or CGGT (for the fourth well 634). Subsequently, when the data was to be read, the strands from the first through fourth wells 631, 632, 633, 634 may be copied and the copies bound to oligos in corresponding first through fourth groups of binding sites 1411, 1412, 1413, 1414 on the surfaces of the beads. The bead 1410 with the bound machine-written polynucleotides may then be transported to the read surface of the flow cell, and the oligos they are bound to may be used to determine the well 631, 632, 633, 634 in which they were originally written (i.e., a strand starting with the sequence AATC may be recognized as originating from the first well 631, a strand starting with the sequence GCCA may be recognized as originating from the second well 632, etc.).

It should be understood that variations on the description of multiplexing provided above in the context of FIG. 19 are also possible and may be included in some implementations. For example, in some implementations, rather than each well 631, 632, 633, 634 having an identification sequence uniquely matching one set of binding sites on the surface of a bead 1410, there may be a many: 1 relationship between sequences used to identify wells 631, 632, 633, 634 and binding sites on the surface of a bead 1410. For instance, if each well 631, 632, 633, 634 had an m base address sequence, the first p bases in that sequence may indicate which set of binding sites/which channel on the surface of a bead may be used to transport that well's strands, with the remaining bases being used to distinguish the wells within a channel from each other. Additionally, in some implementations, barcoding on a bead surface may potentially be used to replace spatial barcoding on the flow cell during the transfer process (e.g., when machine written polynucleotide(s) were copied to the bead, they may be copied with the sequence used to bind them to the surface of the bead, rather than the full sequence used to identify individual wells).

As another example of a potential variation, in some cases, rather than having particular wells tied in advance to particular portions of the surface of a bead, when it was time to transport a copy of machine-written polynucleotide from a write position to a read position in a flow cell, the terminal end of the strand may be deprotected and a sequence that may bind to a particular portion of a bead may be added to it. For example, with a bead such as the bead 1410 shown in FIG. 19, in this type of implementation, if strands from four wells were to be transported, then sequences that may bind to the four binding sites 1411, 1412, 1413, 1414 may be added to them so that those strands may be transported simultaneously on the surface of a single bead 1410 regardless of the wells they were originally written to.

It should also be understood that, in implementations where beads are present, variations on their use may extend beyond different approaches to multiplexing. For example, in some implementations, in addition to, or as an alternative to, using beads to transport and/or store data encoded in machine-written polynucleotides, beads may be used to store administrative information, such as an index indicating where various logical data groupings (e.g., files) were stored. In some implementations where this type of administrative information is stored on beads, it may be stored in machine-written polynucleotides that start with specific unique sequences that distinguish those strands from other strands that encode files or similar data. These unique sequences may also be used to capture machine written strands encoding this type of administrative information so that, when data was to be retrieved, those strands may be captured and sequenced to determine where the data to be retrieved was located. In some implementations, administrative information may also, or alternatively, be stored on beads in other ways, such as color coding or some other form of optical coding (e.g., holographic barcoding) Additionally, in some implementations where administrative information is stored on beads, it may also be stored in non-nucleotide memory where it may provide redundancy in the event that the administrative information on the bead is lost or corrupted. Similarly, in some implementations, beads may be contained in a flow cell only temporarily, and may be moved off of the flow cell after data is written to them, such as to store them in a different storage module (e.g., a tube, as described previously), or to dispose of them (e.g., after the data that had been written or bound to them was read and the beads were no longer needed).

Other variations are also possible. For example, in some implementations that use the technique of reading information by copying the machine-written polynucleotide(s) where the information was encoded and then reading the information from the copy(ies) rather than the original copy(ies) may be moved from the location where the original strands were written using techniques other than beads, such as electrophoresis, dielectrophoresis, laminar fluid flow or other transport techniques. It should be noted that these techniques may also be used to transport beads in locations where they are present. As another example, in some implementations where there are dedicated reading and writing locations in a flow cell, there may be one dedicated reading location for each writing location (e.g., one reading well for each writing well, and vice versa). In other implementations, there may be a different relationship, such as that there may be multiple writing locations (e.g., different wells) and only one reading location (e.g., a surface of a flow cell without any wells). As another example, in some implementations, reading and writing location(s) may be disposed in different positional relations to each other. For example, in some implementations, dedicated reading locations and writing locations may be on the same surface of a flow cell channel (e.g., on the base surface of the flow cell channel). Additionally, in some implementations, machine written polynucleotide(s) may be moved from writing to reading locations in entire sections, rather than well by well (e.g., a bead may be moved to an area that included data to be read, and copies of all of the strands in the area may be bound to the bead and transported rather than binding and/or transporting strands on a well by well basis).

IX. Miscellaneous

All of the references, including patents, patent applications, and articles, are explicitly incorporated by reference herein in their entirety.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

As used herein, an element or step recited in the singular and proceeded with the word "a" or "an" should be understood as not excluding plural of said elements or steps, unless such exclusion is explicitly stated. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this Specification are used to describe and account for small fluctuations, such as due to variations in processing. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

There may be many other ways to implement the subject technology. Various functions and elements described herein may be partitioned differently from those shown without departing from the scope of the subject technology. Various modifications to these implementations may be readily apparent to those skilled in the art, and generic principles defined herein may be applied to other implementations. Thus, many changes and modifications may be made to the subject technology, by one having ordinary skill in the art, without departing from the scope of the subject technology. For instance, different numbers of a given module or unit may be employed, a different type or types of a given module or unit may be employed, a given module or unit may be added, or a given module or unit may be omitted.

Underlined and/or italicized headings and subheadings are used for convenience only, do not limit the subject technology, and are not referred to in connection with the interpretation of the description of the subject technology. All structural and functional equivalents to the elements of the various implementations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A method for non-volatile storage comprising:
receiving a signal indicating that a removable storage device has been coupled with a module interface of a storage instrument, the removable storage device comprising a flow cell, wherein the module interface is adapted to fix the removable storage device in a static position;
in response to receiving the signal indicating that the removable storage device has been coupled with the module interface, enabling the flow cell for synthesis and sequencing of polynucleotides;
operating a sequencing device comprising one or more illuminators and one or more optical sensors to perform sequencing-by-synthesis on a polynucleotide within a well of a plurality of wells of the flow cell to determine a set of sequencing data that describes nucleotides of the polynucleotide;
operating a fluidics device to provide fluid to the flow cell for sequencing-by-synthesis with the sequencing device;
determining, using a processor, a set of binary data based upon the set of sequencing data and an encoding scheme, wherein the encoding scheme describes a set of rules to convert information between a binary format and a non-binary format associated with the set of sequencing data;
after operating the sequencing device to perform sequencing-by-synthesis on the polynucleotide within the well of the plurality of wells of the flow cell, receiving a signal indicating that the removable storage device is to be dismounted from the module interface;
in response to receiving the signal indicating that the removable storage device is to be dismounted from the module interface, dispensing a preservative fluid to the flow cell wherein the preservative fluid is adapted provide a preservative coating on the flow cell to preserve and protect polynucleotides in the plurality of wells, and wherein the preservative fluid is selected from a group consisting of a desiccant, an antioxidant, a polymer coating, and combinations of the foregoing; and
after receiving the signal indicating that the removable storage device is to be dismounted from the module interface, removing the removable storage device from the module interface.

2. The method of claim 1, further comprising:
receiving a set of input data in the binary format;
determining a set of input sequencing data in the non-binary format based upon the set of input data and the encoding scheme; and
introducing a nucleotide carrier fluid to the flow cell to create an input polynucleotide in a target well of the plurality of wells based on the set of input sequencing data.

3. The method of claim 1, wherein enabling the flow cell for synthesis and sequencing of polynucleotides comprises operating the fluidics device to provide a preparation fluid to the flow cell, wherein the preparation fluid is adapted to remove a preservative coating on the flow cell.

4. The method of claim 1, wherein enabling the flow cell for synthesis and sequencing of polynucleotides comprises operating a temperature control device, wherein the temperature control device raises a temperature of the flow cell relative to the temperature of the flow cell when the signal indicating that the removable storage device had been coupled with the module interface was received.

5. The method of claim 4, wherein raising the temperature of the flow cell relative to the temperature of the flow cell when the signal indicating that the removable storage device had been coupled with the module interface was received comprises raising the temperature of the flow cell to a predetermined temperature.

6. The method of claim 5, wherein the predetermined temperature is a temperature for sequencing and synthesizing polynucleotides.

7. The method of claim 6, wherein the predetermined temperature is between 59° C. and 95° C.

8. A method for non-volatile storage comprising:
receiving a signal indicating that a removable storage device has been coupled with a module interface of a storage instrument, the removable storage device comprising a flow cell, wherein the module interface is adapted to fix the removable storage device in a static position;
in response to receiving the signal indicating that the removable storage device has been coupled with the module interface, enabling the flow cell for synthesis and sequencing of polynucleotides;
operating a sequencing device comprising one or more illuminators and one or more optical sensors to perform sequencing-by-synthesis on a polynucleotide within a well of a plurality of wells of the flow cell to determine a set of sequencing data that describes nucleotides of the polynucleotide;
operating a fluidics device to provide fluid to the flow cell for sequencing-by-synthesis with the sequencing device;
determining, using a processor, a set of binary data based upon the set of sequencing data and an encoding scheme, wherein the encoding scheme describes a set of rules to convert information between a binary format to and a non-binary format associated with the set of sequencing data;
after operating the sequencing device to perform sequencing-by-synthesis on the polynucleotide within the well of the plurality of wells of the flow cell, receiving a signal indicating that the removable storage device is to be dismounted from the module interface;
in response to receiving the signal indicating that the removable storage device is to be dismounted from the module interface freeze drying the flow cell to preserve polynucleotides in the plurality of wells; and after receiving the signal indicating that the removable storage device is to be dismounted from the module interface, removing the removable storage device from the module interface.

9. The method of claim 8, wherein:

the method comprises removing the removable storage device from the module interface;

receiving the signal indicating that the removable storage device is to be dismounted from the module interface takes place after operating the sequencing device to perform sequencing-by-synthesis on the polynucleotide within the well of the plurality of wells of the flow cell; and removing the removable storage device from the mobile interface takes place after receiving the signal indicating that the removable storage device is to be dismounted from the module interface.

* * * * *